United States Patent
Quellet et al.

(10) Patent No.: US 10,806,683 B2
(45) Date of Patent: Oct. 20, 2020

(54) ENCAPSULATED PERFUME COMPOSITIONS

(71) Applicant: GIVAUDAN SA, Vernier (CH)

(72) Inventors: Christian Quellet, Bienne (CH); Andras Borosy, Duebendorf (CH)

(73) Assignee: GIVAUDAN SA, Vernier (CH)

(*) Notice: Subject to any disclaimer, the term of this patent is extended or adjusted under 35 U.S.C. 154(b) by 98 days.

(21) Appl. No.: 15/739,009

(22) PCT Filed: Jun. 22, 2016

(86) PCT No.: PCT/EP2016/064343
§ 371 (c)(1),
(2) Date: Dec. 21, 2017

(87) PCT Pub. No.: WO2016/207179
PCT Pub. Date: Dec. 29, 2016

(65) Prior Publication Data
US 2018/0177689 A1  Jun. 28, 2018

(30) Foreign Application Priority Data
Jun. 22, 2015 (GB) .................... 1510942.4

(51) Int. Cl.
| | | |
|---|---|---|
| A61K 8/11 | (2006.01) | |
| A61Q 5/02 | (2006.01) | |
| A61Q 5/12 | (2006.01) | |
| C11D 3/50 | (2006.01) | |
| A61Q 13/00 | (2006.01) | |
| A61K 8/84 | (2006.01) | |

(52) U.S. Cl.
CPC .................. *A61K 8/11* (2013.01); *A61K 8/84* (2013.01); *A61Q 5/02* (2013.01); *A61Q 5/12* (2013.01); *A61Q 13/00* (2013.01); *C11D 3/505* (2013.01); *A61K 2800/56* (2013.01)

(58) Field of Classification Search
None
See application file for complete search history.

(56) References Cited

FOREIGN PATENT DOCUMENTS

| | | |
|---|---|---|
| EP | 2860237 A1 | 4/2015 |
| WO | 9955819 A1 | 11/1999 |
| WO | 0231092 A2 | 4/2002 |
| WO | 2007034187 A1 | 3/2007 |
| WO | 2009001320 A1 | 12/2008 |
| WO | 2009153695 A1 | 12/2009 |
| WO | 2011075425 A1 | 6/2011 |
| WO | 2013092375 A1 | 12/2012 |
| WO | 2014109412 A1 | 7/2014 |

OTHER PUBLICATIONS

International Search Report and Written Opinion of the International Searching Authority for corresponding application PCT/EP2016/064343 dated Sep. 29, 2016.

*Primary Examiner* — David J Blanchard
*Assistant Examiner* — Sarah J Chickos
(74) *Attorney, Agent, or Firm* — Norris McLaughlin PA

(57) ABSTRACT

Disclosed are perfume compositions containing perfume ingredients selected on the basis that they are able to be stably incorporated into core-shell microcapsules. Perfume selection rules are based on a molecular descriptor of the electron density distribution within a perfume ingredient—RECON VOLTAE. Perfume ingredients having known RECON_VOLTAE values larger than about 1200 Bohr$^3$, more particularly larger than 1540 Bohr$^3$, and more particularly still larger than about 1750 Bohr$^3$ are particularly suitable for encapsulation.

19 Claims, No Drawings

ENCAPSULATED PERFUME COMPOSITIONS

This is an application filed under 35 USC 371 of PCT/EP2016/064343 filed 22 Jun. 2016 which in turn was based on GB 1510942.4 filed 22 Jun. 2015. The applicant claims all available priority benefit to the foregoing applications, and incorporates the entirety of their disclosures herein.

The invention is concerned with perfume compositions, which are designed to be encapsulated in core-shell microcapsules. The invention also relates to encapsulated perfume compositions containing said core-shell microcapsules and their use in consumer products, such as household, laundry and personal care products.

Consumer products, such as household, laundry and personal care products, typically contain perfumes that are expected to deliver long-lasting and pleasant odours to substrates onto which they are applied. However, it is often not possible to achieve this goal if perfume is incorporated into such products in neat form, as so-called "free-oil". For this reason, it is common to formulate perfume composition in the cores of core-shell microcapsules.

The advantages of encapsulating perfumes in this way are well known in the art. In particular, microcapsules can increase the stability and useful life of the encapsulated perfume ingredients; they can facilitate the manipulation, handling and storage of the encapsulated perfume compositions, and control the emanation of pleasant odours in time and space; and they can also isolate perfume ingredients from chemical attack of aggressive external media in which they are suspended.

However, it remains a matter of considerable difficulty for formulators to design core-shell microcapsules that possess the requisite barrier properties to protect the core contents from external media during manufacture and storage, and yet still permit release of the core contents at a desired time, in response to an external stimulus, such as the action of heat, moisture, chemical reactivity, or in response to mechanical disruption.

Core-shell microcapules, particularly those comprising aminoplast or gelatin shells, are somewhat permeable and allow their core contents to leak when suspended in aqueous media, and particularly aqueous media containing surfactants and/or solvents. Perfume ingredients tend to leak from the cores over time in a process of diffusion. This is particularly a problem in media containing unstructured surfactants, which promote leakage by solubilizing or incorporating perfume ingredients into micelles.

It is obviously not desirable that perfume is extracted prematurely from microcapsules, but at the same time the microcapsules should not be so strong and resistant to disruption that they do not release their contents other than in response to the application of excessively high mechanical forces.

Today's consumers increasingly measure the efficacy of a fragranced consumer product not only in terms of the perfume intensity in response physical force being applied to a treated substrate, such as skin, hair or fabrics (the so-called post-rub intensity), but also the fragrance perception before application of physical force (pre-rub intensity). Post-rub intensity might be desirable for sustained perfumery benefits, but up-front freshness and perfume intensity (pre-rub) is also desirable to ensure perfumery benefits are perceivable at all stages of application of a consumer product.

Improving perfume release from microcapsules has been addressed in the prior art by proposing rules for the selecting the most appropriate perfume ingredients to be encapsulated. For example, improved perfume delivery from capsules has been claimed for perfumes comprising large amounts of ingredients having high clogP values as illustrated in U.S. Pat. No. 5,500,138.

Similarly, WO99/65458 teaches perfume selection criteria based on the clogP values of said ingredients, amongst other parameters.

WO2004016234 suggests perfume ingredients having clog P values of 2.5 or greater should be used in high amounts, i.e. 80-90% by weight, for optimal performance.

In EP1533364 clogP is regarded as a key parameter in encapsulated perfume design. Preferred perfume ingredients should have clogP values of 3.3 or greater, more particularly 4 or greater and these ingredients should be used in high amounts, for example greater than 80%, more particularly greater than 90% by weight.

The applicant has found, however, that selecting perfume ingredients suitable for encapsulation based on a consideration of their clogP values neither accounts adequately for the leakage stability of microcapsules when suspended in media containing high levels of surfactants, nor for pre-rub perfume impact of said encapsulated perfume compositions.

There remains a need to provide encapsulated perfume compositions that can be stably incorporated into consumer products, particularly those containing high levels of unstructured surfactants, which are resistant to leakage during storage, and which can be deposited onto a substrate to provide a long-lasting fragrance impression.

After considerable research effort, the applicant has discovered means for selecting perfume ingredients, such that encapsulated perfume compositions containing said ingredients, when incorporated into consumer products, are resistant to leakage, and furthermore, when deposited onto a substratecan provide both pre-rub and post-rub perfume benefits.

In particular, the applicant has found that by employing perfume selection criteria set forth in this disclosure, it is possible to control both the permeability of perfume compositions through a microcapsule shell and the rate of diffusion of the perfume ingredients through the shell.

More specifically, the applicant has found that a critical parameter of perfume ingredient selection is the electron density distribution within a perfume ingredient, as reflected by the temperature-independent integral of the molecular iso-surface having electron density equal to $$0.002 e/a_0^3$$

wherein e is the dimension-less electron charge and $a_0$ is the Bohr radius of the hydrogen atom ($a_0$=5.2917720859×10$^{-11}$ m).

Employing Molecular Operating Environment chemical computational software (Version 2009, ex Chemical Computing Group, Canada, or later versions thereof, and optionally using the DDASSL RECON software plug-in (Rensselaer Polytechnic Institute, 2001-2003, or later versions thereof)), the value of this integral is given by the so-called RECON_VOLTAE quantum chemically derived descriptor. In particular, it was surprisingly found that the leakage of perfume ingredients through a microcapsule shell is considerably suppressed when the value of the molecular iso-surface integral of ingredients exceeds a certain value, more fully described herein below.

RECON VOLTAE is a parameter describing or expressing the topography of a molecule iso-surface that encloses a molecular space having an electron density that is equal to 0.002 $e/a^3_0$.

Accordingly, the present invention provides in a first aspect a perfume composition adapted to be encapsulated in core-shell microcapsules, wherein said perfume composition contains perfume ingredients having known RECON_VOLTAE values larger than about 1200 Bohr$^3$, more particularly larger than about 1540 Bohr$^3$, and still more particularly larger than about 1750 Bohr$^3$.

In another aspect of the present invention there is provided an encapsulated perfume composition comprising at least one core-shell microcapsule dispersed in a suspending medium, the core comprising perfume ingredients having known RECON_VOLTAE values larger than about 1200 Bohr$^3$, more particularly larger than 1540 Bohr$^3$, and more particularly still larger than about 1750 Bohr$^3$.

In yet another aspect of the invention there is provided a consumer product, such as a household, laundry and personal care products disclosed herein, containing an encapsulated perfume composition as described herein.

Further aspects of the invention include methods of preparing encapsulated perfume compositions, said methods comprising the steps of mixing together perfume ingredients, selected in accordance with the perfume selection criteria set forth herein, and in the amounts and relative proportions set forth herein.

Further aspects of the invention also include encapsulated perfume compositions made according to the methods described herein.

Further aspects of the invention also include methods of forming consumer products, such as household, laundry and personal care products disclosed herein, comprising the step of incorporating into said consumer products encapsulated perfume compositions described herein and made according to methods described herein. Other aspects of the invention include methods of improving the resistance to leakage of encapsulated perfume compositions, said methods comprising the step of encapsulating perfume compositions that contain perfume ingredients selected in accordance with the perfume selection criteria set forth herein, and in the amounts and relative proportions set forth herein.

As used herein, the term "known" as it is used in relation to the RECON_VOLTAE values, or any of the other physico-chemical parameters described herein, means the values are known to a formulator of a perfume composition, or can be calculated in accordance with the teaching of the present invention.

In an embodiment of the present invention more than 70 wt %, in particular more than 80 wt %, and more particularly more than 90 wt % of the perfume ingredients contained the cores of said core-shell microcapsules have known RECON_VOLTAE values larger than about 1200 Bohr$^3$.

In a more particular embodiment of the present invention more than 30 wt %, more particularly more than 35 wt %, and more particularly still, more than 40 wt % of the perfume ingredients contained in the cores of said core-shell microcapsules have known RECON_VOLTAE values larger than about 1540 Bohr$^3$.

Those encapsulated perfume compositions in which more than 30 wt %, more particularly more than 35 wt %, and more particularly still, more than 40 wt % of the perfume ingredients contained in the microcapsule cores have known RECON_VOLTAE values larger than about 1540 Bohr$^3$, are particularly suitable for incorporation in aggressive (extractive) media. These media include fabric softening or conditioning products containing quaternized ester surfactants (so-called "esterquats") and non-ionic surfactants. They are particularly suitable for use in fabric softening or conditioning products containing un-structured surfactants. Un-structured surfactants are relatively free to extract perfume ingredients by forming micelles or vesicles around them, and thereby solubilizing them. They can be contrasted with "structured surfactants", which are essentially immobilized in a structure, such as a liquid crystalline, generally lamellar phase (sometimes called "mesophases") and are thus generally unavailable to form micelles or vesicles, and are far less aggressive or extractive as a result. Unstructured surfactant compositions are generally transparent. This can be contrasted with structure compositions, which generally are turbid, opaque or pearlescent.

Fabric softener or conditioner products are more fully described herein below.

Encapsulated perfume compositions in which more than 70 wt %, more particularly, more than 80 wt %, and more particularly still, more than 90 wt % of perfume ingredients in the microcapsule cores have known RECON_VOLTAE values larger than about 1750 Bohr$^3$ form another embodiment of the present invention.

Encapsulated perfume compositions in which more than 70 wt %, more particularly, more than 80 wt %, and more particularly still, more than 90 wt % of perfume ingredients in the microcapsule cores have known RECON_VOLTAE values larger than about 1750 Bohr$^3$ are particularly suitable for incorporation into very aggressive media, such as those found in shampoos and other personal cleansing compositions comprising high level of anionic, non-ionic and/or zwitterionic surfactants.

In accordance with a particular embodiment of the present invention, the encapsulated perfume compositions described herein are characterised in that they are comprised of at least 3 perfume ingredients, more particularly at least 5, still more particularly at least 7 and more particularly still at least 9 perfume ingredients having RECON_VOLTAE values larger than about 1200 Bohr$^3$, or larger than about 1540 Bohr$^3$ or larger than about 1750 Bohr$^3$.

As used herein in relation to encapsulated perfume ingredients "wt %" refers to the concentration of a perfume ingredient or group of perfume ingredients, relative to the total amount of encapsulated perfume ingredients. Preferably, the microcapsule cores contain only perfume ingredients, however, it is contemplated that in addition to perfume ingredients, the contents of the cores may contain non-perfumery ingredients or excipients such as solvents or diluents. For example, certain perfume ingredients are provided as solutions or are diluted in suitable solvents, such as triethyl citrate "TEC". In such cases, only the amount of perfume would contribute to the wt % calculation and not the solvent used to dissolve or dilute the perfume ingredient.

Such solvents or diluents are hydrophobic materials that are miscible in the perfume ingredients, and which have little or no odour in the quantities employed. Solvents commonly employed have high C log P values, for example greater than 6 and even greater than 10. Solvents include triglyceride oil, mono and diglycerides, mineral oil, silicone oil, diethyl phthalate, poly(alpha-olefins), castor oil and isopropyl myristate.

The microcapsule cores may also contain commonly employed adjuvants. The term "adjuvants" refers to ingredients that may affect the performance of a composition other than its hedonic performance. For example, an adjuvant may be an ingredient that acts as an aid to processing a perfume composition or consumer product containing said composition, or it may improve handling or storage of a perfume composition or consumer product. It might also be an ingredient that provides additional benefits such as imparting colour or texture. It might also be an ingredient that imparts light resistance or chemical stability to one or more ingredients contained in a perfume composition or consumer product. A detailed description of the nature and type of adjuvants commonly used in perfume compositions or consumer products cannot be exhaustive, but it has to be mentioned that said ingredients are well known to a person skilled in the art. Examples of adjuvants include surfactants and emulsifiers; viscosity and rheology modifiers; thickening and gelling agents; preservative materials; pigments, dyestuffs and colouring matters; extenders, fillers and reinforcing agents; stabilisers against the detrimental effects of heat and light, bulking agents, acidulants, buffering agents and antioxidants.

A comprehensive list of perfume ingredients available for selection in accordance with the present invention, as well as exicpients commonly used in perfumery, may be found in the perfumery literature, for example "Perfume & Flavor Chemicals", S. Arctander (Allured Publishing, 1994), as well as later editions of this work, which are herein incorporated by reference.

By formulating perfume compositions in accordance with the known RECON_VOLTAE values set out herein, it is possible to form encapsulated perfume compositions characterized in that the microcapsules have a high resistance to extraction or leakage into external suspending media. Because of the low propensity to leakage, it is possible to form encapsulated perfume compositions that are characterized in that the microcapsules have a very high core to shell weight ratio.

Thus, in another aspect of the present invention, there is provided an encapsulated perfume composition as described herein, wherein the core to shell weight ratio of the microcapsules is about 90:10 at least, or more particularly 95:5 at least.

In yet another aspect of the invention there is provided a method of preparing an encapsulated perfume composition, wherein the core to shell weight ratio of the microcapsules is about 90:10 at least, or more particularly 95:5 at least, said method comprising the step of encapsulating a perfume composition containing perfume ingredients selected in accordance with the perfume selection criteria set forth herein, and in the amounts and relative proportions set forth herein.

Without wishing to be bound by theory, it is believed that the electron density distribution of a perfume ingredient, as reflected by its RECON_VOLTAE value, influences the way it diffuses or leaks through the shell. In particular, the diffusion of ingredients having RECON_VOLTAE values above the threshold values recited hereinabove, e.g. above about 1200, is delayed, or even suppressed, relative to perfume ingredients having RECON_VOLTAE values below the given threshold value. It follows from the above that in order to provide encapsulated perfume compositions having desirable long-term stability in consumer products, particularly those that contain aggressive or extractive media, such as those found in personal cleansing compositions and laundry detergents, while still delivering perfume at a desired release rate after deposition onto a substrate, the encapsulated perfume composition should contain a certain amount of perfume ingredients having known RECON_VOLTAE values below the aforementioned 1200 threshold. These sub-threshold perfume ingredients will diffuse more readily from the microcapsules.

Possessed with the knowledge of the RECON_VOLTAE parameter, and the relationship of RECON_VOLTAE to both performance and stability of encapsulated perfume compositions, the skilled person is able to create suitable encapsulated perfume compositions, by balancing the proportions of both sub- and super-threshold perfume ingredients, which are designed to be both stable and performant when used in consumer products containing more or less extractive media.

Thus, an encapsulated perfume composition as defined hereinabove, additionally comprising encapsulated perfume ingredients having RECON_VOLTAE values below 1200 Bohr$^3$, forms yet another aspect of the present invention.

In a particular embodiment of the present invention, the encapsulated perfume composition is characterized by a distribution of perfume ingredients having known RECON_VOLTAE values, wherein 70 wt % or more, more preferably 80 wt % or more, and most preferably 90 wt % or more of the perfume ingredients have known RECON_VOLTAE values larger than 1200 Bohr$^3$ and 0.1 to 30 wt %, more particularly from 1 to 20 wt % and more particularly still from 1 to 10 wt % of perfume ingredients having known RECON_VOLTAE values below 1200 Bohr$^3$.

In another embodiment of the present invention, the encapsulated perfume composition is characterized by a distribution of perfume ingredients having known RECON_VOLTAE values, wherein:
  30 wt % or more, more particularly 35 wt % or more, and more particularly 40 wt % or more of perfume ingredients have known RECON_VOLTAE values larger than 1540 Bohr$^3$;
  20 to 60 wt %, more particularly 25 to 50 wt % and more particularly still 30 to 40 wt % of the perfume ingredients have known RECON_VOLTAE values from 1200 Bohr$^3$ to 1540 Bohr$^3$; and
  0.1 to 30 wt %, more particularly from 1 to 20 wt % and more particularly still, from 1 to 10 wt % of the perfume ingredients have known RECON_VOLTAE values below 1200 Bohr$^3$.

In yet another embodiment of the present invention, the encapsulated perfume composition is characterized by a distribution of perfume ingredients having known RECON_VOLTAE values, wherein:
  from 0.5 to 30 wt %, more particularly from 1 to 25 wt %, and more particularly still from to 20 wt % of the perfume ingredients have known RECON_VOLTAE values above 1750 Bohr$^3$
  20 to 60 wt %, more particularly 25 to 55 wt % or more, more particularly still from 30 to 50 wt % or more of the perfume ingredients having known RECON_VOLTAE values from 1540 Bohr$^3$ to 1750 Bohr$^3$; and
  5 to 50 wt % or more, more particularly 10 to 40 wt % or more particularly still 15 to 30 wt % or more of the perfume ingredients have known RECON_VOLTAE values from 1200 Bohr$^3$ to 1540 Bohr$^3$; and
  0.1 to 30 wt %, more particularly from 1 to 20 wt % and more particularly still from 1 to 10 wt % of perfume ingredients have known RECON_VOLTAE values below 1200 Bohr$^3$.

In yet another embodiment of the present invention, the encapsulated perfume composition is characterized by a distribution of perfume ingredients having known RECON_VOLTAE values, wherein 70 wt % or more, more preferably 80 wt % or more, and most preferably 90 wt % or more of perfume ingredients have known RECON_VOLTAE values larger than 1750 Bohr$^3$; and 0.1 to 30 wt %, more particularly from 1 to 20 wt % and more particularly still from 1 to 10 wt % of the perfume ingredients have known RECON_VOLTAE values below 1750 Bohr$^3$.

Preferably, the weight average known RECON_VOLTAE values of the perfume ingredients of encapsulated perfume compositions of the present invention should be larger than 1540 Bohr³ and more particularly larger than 1750 Bohr³.

The weight average of known RECON_VOLTAE values is defined here as the weighed algebraic mean of the ingredient known RECON_VOLTAE values divided by the number of ingredients:

$$\langle RECON\_VOLTAE \rangle_{perfume} \equiv 1/n \sum_n (\%_i)(RECON\_VOLTAE_i)$$

wherein n is the number of ingredients i, $\%_i$ the weight percentage of ingredient i and $RECON\_VOLTAE_i$, the RECON_VOLTAE value of ingredient i.

Particularly stable and performant encapsulated perfume compositions can be prepared, when the selection of perfume ingredients is made on the basis of both the RECON_VOLTAE parameter as described hereinabove, and according to a perfume ingredient's equilibrium headspace-capsule partition coefficient "Kcaps" The equilibrium headspace-capsule partition coefficient is defined as the headspace concentration ($HS_i^e$) of a perfume ingredient i in equilibrium with a microcapsule containing an encapsulated perfume composition P comprising perfume ingredient i at a given concentration divided by the headspace concentration ($HS_i^P$) in equilibrium with free perfume P comprising same concentration of ingredient i.

$$Kcaps_i = \frac{HS_i^c}{HS_i^P}$$

The headspace concentration in equilibrium with a microcapsule can be measured using techniques well known to a person skilled in the art. In a typical procedure, an encapsulated perfume composition containing a known concentration of microcapsules is transferred to a vial VC, which is closed with a septum and allowed to equilibrate at 25° C., and a known amount of free perfume is transferred to a vial VP containing a strip of blotter paper on which the perfume is deposited with a syringe. The vial is closed with a septum and allowed to equilibrate at 25° C. Headspace aliquots are then taken from both vials and the headspace concentration profiles are determined quantitatively using methods known in the art, such as headspace capillary gas chromatography, headspace gas chromatography ion mobility spectrometry, gas spectroscopy and the like.

Kcaps may be determined experimentally, or it can be calculated for an ingredient using techniques known in the art. In particular, the effect of perfume ingredients on microcapsule stability can be predicted from QSAR analysis using MOE software.

As the person skilled in the art will appreciate, QSAR methods, in the context of the present invention, assume that performance of a perfume ingredient is correlated with its chemical structure and that as a consequence activity can be modeled as a function of calculable physiochemical attributes. Such a model for performance prediction can then be used to screen the palette of known perfume ingredients, or indeed libraries of other molecules for useful candidate ingredients.

Using QSAR analysis of a representative sample of perfume ingredients in the present invention resulted in the identification of a physicochemical parameter ($\log_{10}$ Kcaps) contributing to the effect of perfume ingredients on the stability of microcapsules.

$\log_{10}$ Kcaps was calculated by constructing a Quantitative Structure Activity Relationship, by performing a linear regression of molecular descriptors available within computational chemistry perfume MOE (Molecular Operation Environment, version 2013.08.01, purchased from Chemical Computing Group, Corporate Headquarters, 1010 Sherbrooke St. W, Suite 910, Montreal, Canada H3A 2R7, optionally using the DDASSL RECON software plug-in (Rensselaer Polytechnic Institute, 2001-2003, or later versions thereof)). QSAR analysis was carried out using a total of 75 perfume ingredients selected for the analysis on the basis of them being a representative set of perfume ingredients that had been used in encapsulated perfume compositions. The resulting QSAR equation is given below:

$\log_{10}$ Kcaps=−0.613884945931533+
0.367145678964078 Average_EO_Neg+
0.154423533060832 E_sol+1.72305610065098
MACCS(136)+0.0650007063247245 PEO-
E_VSA+3−1.6045990231291 PEOE_VSA_F-
POS+12.0572868318683 RA_2D_pEP10−
1082.58386145862 RA_nEP2−
0.0382420195399682 RECON_Del(K)NA3+
53.5822360317755 RECON_FEP9−
2.50813850930136 RECON_FPIP8+
5.73871249195905 RECON_SIKA10+
0.0400054462330909 kS_tsC The definition of the molecular descriptors used in above equation can be found in MOE manual version 2013.08.01 (edited by Molecular Operation Environment, Chemical Computing Group, Corporate Headquarters, 1010 Sherbrooke St. W, Suite 910, Montreal, Canada H3A 2R7); or R. Todeschini and V. Consonni, Handbook of Molecular Descriptors, Wiley, 2000; and DDASSL RECON manual (Rensselaer Polytechnic Institute, 2001-2003, or later versions thereof).

Calculated $\log_{10}$ Kcaps values of some perfume ingredients are provided in the Tables below.

Perfume ingredients that are particularly useful in encapsulated perfume compositions according to the present invention may be grouped according to their respective RECON_VOLTAE values and their calculated $\log_{10}$ Kcaps values.

Thus, GROUP 1 perfume ingredients have RECON_VOLTAE values larger than 1200 Bohr³ and calculated $\log_{10}$ Kcaps which are greater than −3, where the term $\log_{10}$ refers to the decimal logarithm. Perfume ingredients of GROUP 1 include but are not limited to

| Perfumery ingredient | RECON_VOLTAE (Bohr3) | LogKcaps |
| --- | --- | --- |
| HEDIONE (methyl 3-oxo-2-pentylcyclopentaneacetate) | 1784 | −2.4 |
| ALLYL CYCLOHEXYL PROPIONATE (allyl 3-cyclohexylpropanoate) | 1606 | −2.0 |
| AGRUMEX (2-(tert-butyl)cyclohexyl acetate) | 1678 | −1.9 |
| DIMETHYL BENZYL CARBINYL ACETATE (2-methyl-1-phenylpropan-2-yl acetate) | 1506 | −2.4 |

-continued

| Perfumery ingredient | RECON_VOLTAE (Bohr3) | LogKcaps |
|---|---|---|
| IRISONE ALPHA ((E)-4-(2,6,6-trimethylcyclohex-2-en-1-yl)but-3-en-2-one) | 1676 | −1.8 |
| ISO E SUPER (1-(2,3,8,8-tetramethyl-1,2,3,4,5,6,7,8-octahydronaphthalen-2-yl)ethanone) | 2024 | −1.4 |
| ISORALDEINE 70 ((E)-3-methyl-4-(2,6,6-trimethylcyclohex-2-en-1-yl)but-3-en-2-one) | 1806 | −2.0 |
| NECTARYL (2-(2-(4-methylcyclohex-3-en-1-yl)propyl)cyclopentanone) | 1822 | −1.9 |
| BOISAMBRENE FORTE ((ethoxymethoxy)cyclododecane) | 2063 | −2.0 |
| BOISIRIS ((1S,2R,5R)-2-ethoxy-2,6,6-trimethyl-9-methylenebicyclo[3.3.1]nonane) | 1914 | −1.0 |
| JASMACYCLENE ((3aR,6S,7aS)-3a,4,5,6,7,7a-hexahydro-1H-4,7-methanoinden-6-yl acetate) | 1418 | −1.7 |
| FLOROCYCLENE ((3aR,6S,7aS)-3a,4,5,6,7,7a-hexahydro-1H-4,7-methanoinden-6-yl propionate) | 1549 | −1.6 |
| HEXYL SALICYLATE (hexyl 2-hydroxybenzoate) | 1685 | −1.6 |
| DIPENTENE (1-methyl-4-(prop-1-en-2-yl)cyclohex-1-ene) | 1203 | −0.1 |
| TETRAHYDRO LINALOOL (3,7-dimethyloctan-3-ol) | 1449 | −2.2 |
| AMYL SALICYLATE (pentyl 2-hydroxybenzoate) | 1556 | −1.4 |
| ALDEHYDE C 12 MNA PURE (2-methylundecanal) | 1661 | −2.3 |
| BUTYL CYCLOHEXYL ACETATE PARA (4-(tert-butyl)cyclohexyl acetate) | 1682 | −2.7 |
| DAMASCONE DELTA ((E)-1-(2,6,6-trimethylcyclohex-3-en-1-yl)but-2-en-1-one) | 1654 | −1.3 |
| DIMETHYL BENZYL CARBINYL BUTYRATE (2-methyl-1-phenylpropan-2-yl butyrate) | 1767 | −1.6 |
| EUCALYPTOL ((1s,4s)-1,3,3-trimethyl-2-oxabicyclo[2.2.2]octane) | 1278 | −1.0 |
| FRUTONILE (2-methyldecanenitrile) | 1597 | −1.9 |
| HEXYL CINNAMIC ALDEHYDE ((E)-2-benzylideneoctanal) | 1778 | −2.5 |
| IONONE BETA ((E)-4-(2,6,6-trimethylcyclohex-1-en-1-yl)but-3-en-2-one) | 1670 | −1.6 |
| TERPINYL ACETATE (2-(4-methylcyclohex-3-en-1-yl)propan-2-yl acetate) | 1590 | −2.0 |
| UNDECAVERTOL ((E)-4-methyldec-3-en-5-ol) | 1531 | −2.1 |
| LINALOOL (3,7-dimethylocta-1,6-dien-3-ol) | 1367 | −2.3 |
| GARDOCYCLENE ((3aR,6S,7aS)-3a,4,5,6,7,7a-hexahydro-1H-4,7-methanoinden-6-yl isobutyrate) | 1677 | −1.5 |
| IRISONE ((E)-4-(2,6,6-trimethylcyclohex-2-en-1-yl)but-3-en-2-one) | 1676 | −1.8 |
| LILIAL (3-(4-(tert-butyl)phenyl)-2-methylpropanal) | 1738 | −2.0 |
| LINALYL ACETATE (3,7-dimethylocta-1,6-dien-3-yl acetate) | 1653 | −1.5 |
| GERANIOL ((E)-3,7-dimethylocta-2,6-dien-1-ol) | 1357 | −2.0 |
| ALLYL OENANTHATE (allyl heptanoate) | 1436 | −2.5 |
| PETALIA (2-cyclohexylidene-2-(o-tolyl)acetonitrile) | 1753 | −1.4 |
| NEOBERGAMATE FORTE (2-methyl-6-methyleneoct-7-en-2-yl acetate) | 1650 | −1.4 |
| ISONONYL ACETATE (3,5,5-trimethylhexyl acetate) | 1632 | −1.0 |
| FRESKOMENTHE (2-(sec-butyl)cyclohexanone) | 1313 | −1.6 |
| ORIVONE (4-(tert-pentyl)cyclohexanone) | 1474 | −2.1 |
| NONADYL (6,8-dimethylnonan-2-ol) | 1579 | −1.8 |
| METHYL PAMPLEMOUSSE (6,6-dimethoxy-2,5,5-trimethylhex-2-ene) | 1632 | −1.9 |
| ETHYL CAPRYLATE (ethyl octanoate) | 1462 | −1.5 |
| AMBER CORE (1-((2-(tert-butyl)cyclohexyl)oxy)butan-2-ol) | 1972 | −2.3 |

-continued

| Perfumery ingredient | RECON_VOLTAE (Bohr3) | LogKcaps |
|---|---|---|
| CASHMERAN (1,1,2,3,3-pentamethyl-2,3,6,7-tetrahydro-1H-inden-4(5H)-one) | 1772 | −1.9 |
| CITRONELLOL (3,7-dimethyloct-6-en-1-ol) | 1392 | −2.4 |
| DAMASCENONE ((E)-1-(2,6,6-trimethylcyclohexa-1,3-dien-1-yl)but-2-en-1-one) | 1608 | −1.5 |
| ETHYL SAFRANATE (ethyl 2,6,6-trimethylcyclohexa-1,3-diene-1-carboxylate) | 1579 | −2.0 |
| EUCALYPTOL ((1s,4s)-1,3,3-trimethyl-2-oxabicyclo[2.2.2]octane) | 1278 | −1.0 |
| PEONILE (2-cyclohexylidene-2-phenylacetonitrile) | 1633 | −0.9 |
| DELPHONE (2-pentylcyclopentanone) | 1313 | −1.9 |
| SILVIAL (3-(4-isobutylphenyl)-2-methylpropanal) | 1700 | −2.5 |
| TETRAHYDRO MYRCENOL (2,6-dimethyloctan-2-ol) | 1449 | −2.1 |
| CITRONELLYL PROPIONATE (3,7-dimethyloct-6-en-1-yl propionate) | 1808 | −2.0 |
| CYCLOHEXYL SALICYLATE (cyclohexyl 2-hydroxybenzoate) | 1610 | −2.2 |
| ETHYL CAPROATE (ethyl hexanoate) | 1203 | −1.4 |
| CORANOL (4-cyclohexyl-2-methylbutan-2-ol) | 1486 | −2.7 |
| BORNYL ACETATE ((2S,4S)-1,7,7-trimethylbicyclo[2.2.1]heptan-2-yl acetate) | 1631 | −1.8 |
| ALDEHYDE C 10 DECYLIC (decanal) | 1403 | −2.9 |
| ALDEHYDE C 110 UNDECYLIC (undecanal) | 1533 | −2.8 |
| ALDEHYDE MANDARINE 10%/TEC ((E)-dodec-2-enal) | 1615 | −2.7 |
| AMBERMAX (1,3,4,5,6,7-hexahydro-.beta.,1,1,5,5-pentamethyl-2H-2,4a-Methanonaphthalene-8-ethanol) | 2275 | −2.8 |
| BELAMBRE ((1R,2S,4R)-2'-isopropyl-1,7,7-trimethylspiro[bicyclo[2.2.1]heptane-2,4'-[1,3]dioxane]) | 2112 | −1.6 |
| CITRONELLYL NITRILE (3,7-dimethyloct-6-enenitrile) | 1429 | −1.6 |
| FLORHYDRAL (3-(3-isopropylphenyl)butanal) | 1568 | −2.7 |
| GERANYL ACETATE SYNTHETIC ((E)-3,7-dimethylocta-2,6-dien-1-yl acetate) | 1643 | −2.4 |
| HABANOLIDE ((E)-oxacyclohexadec-12-en-2-one) | 1978 | −2.6 |
| HEXYL ISOBUTYRATE (hexyl isobutyrate) | 1460 | −1.0 |
| MYRALDENE (4-(4-methylpent-3-en-1-yl)cyclohex-3-enecarbaldehyde) | 1613 | −2.2 |
| TRIDECENE-2-NITRILE ((E)-tridec-2-enenitrile) | 1818 | −1.5 |
| ROSACETOL (2,2,2-trichloro-1-phenylethyl acetate) | 1731 | −1.5 |
| CITRONELLYL ACETATE (3,7-dimethyloct-6-en-1-yl acetate) | 1678 | −1.7 |
| ETHYL LINALOOL ((E)-3,7-dimethylnona-1,6-dien-3-ol) | 1497 | −2.1 |
| DIPENTENE (1-methyl-4-(prop-1-en-2-yl)cyclohex-1-ene) | 1203 | −0.1 |
| GERANYL ISOBUTYRATE ((E)-3,7-dimethylocta-2,6-dien-1-yl isobutyrate) | 1901 | −1.2 |
| ISOPROPYL METHYL-2-BUTYRATE (isopropyl 2-methyl butanoate) | 1212 | −1.1 |
| RADJANOL SUPER ((E)-2-ethyl-4-(2,2,3-trimethylcyclopent-3-en-1-yl)but-2-en-1-ol) | 1829 | −2.3 |
| TERPINOLENE (1-methyl-4-(propan-2-ylidene)cyclohex-1-ene) | 1204 | −0.1 |
| ETHYL LINALYL ACETATE ((Z)-3,7-dimethylnona-1,6-dien-3-yl acetate) | 1783 | −1.1 |
| SERENOLIDE (2-(1-(3,3-dimethylcyclohexyl)ethoxy)-2-methylpropyl cyclopropanecarboxylate) | 2429 | −2.0 |
| CITRAL ((E)-3,7-dimethylocta-2,6-dienal) | 1311 | −1.8 |
| DIMETHYL OCTENONE (4,7-dimethyloct-6-en-3-one) | 1360 | −0.8 |
| GALBANONE PURE (1-(3,3-dimethylcyclohex-1-en-1-yl)pent-4-en-1-one) | 1663 | −1.9 |
| KOAVONE ((Z)-3,4,5,6,6-pentamethylhept-3-en-2-one) | 1675 | −1.6 |

-continued

| Perfumery ingredient | RECON_VOLTAE (Bohr3) | LogKcaps |
|---|---|---|
| NEROLIDYLE ((Z)-3,7,11-trimethyldodeca-1,6,10-trien-3-yl acetate) | 2257 | −2.3 |
| ADOXAL (2,6,10-trimethylundec-9-enal) | 1878 | −2.5 |
| MENTHOL NATURAL (2-isopropyl-5-methylcyclohexanol) | 1357 | −2.1 |
| ALDEHYDE C 12 LAURIC (dodecanal) | 1662 | −2.9 |
| CITRONELLAL (3,7-dimethyloct-6-enal) | 1363 | −2.4 |
| COSMONE ((Z)-3-methylcyclotetradec-5-enone) | 1924 | −2.5 |
| CYCLAMEN ALDEHYDE (3-(4-isopropylphenyl)-2-methylpropanal) | 1567 | −1.6 |
| DIMETHYL BENZYL CARBINOL (2-methyl-1-phenylpropan-2-ol) | 1223 | −2.4 |
| FLORALOZONE (3-(4-ethylphenyl)-2,2-dimethylpropanal) | 1608 | −1.9 |
| HERBANATE ((2S)-ethyl 3-isopropylbicyclo[2.2.1]hept-5-ene-2-carboxylate) | 1629 | −0.7 |
| LEMONILE ((2E,6Z)-3,7-dimethylnona-2,6-dienenitrile) | 1515 | −1.5 |
| DIMETOL (2,6-dimethylheptan-2-ol) | 1320 | −2.0 |
| PIVAROSE (2,2-dimethyl-2-pheylethyl propanoate) | 1665 | −2.5 |
| PRECYCLEMONE B (1-methyl-4-(4-methylpent-3-en-1-yl)cyclohex-3-enecarbaldehyde) | 1783 | −2.2 |
| CITRONELLYL ACETATE (3,7-dimethyloct-6-en-1-yl acetate) | 1678 | −1.7 |
| ALDEHYDE C 11 UNDECYLENIC (undec-10-enal) | 1498 | −2.9 |
| ETHYL OENANTHATE (ethyl heptanoate) | 1333 | −1.5 |
| KARANAL (5-(sec-butyl)-2-(2,4-dimethylcyclohex-3-en-1-yl)-5-methyl-1,3-dioxane) | 2242 | −1.4 |
| NERYL ACETATE HC ((Z)-3,7-dimethylocta-2,6-dien-1-yl acetate) | 1643 | −2.4 |
| THIBETOLIDE (oxacyclohexadecan-2-one) | 2017 | −2.2 |
| FLOROPAL (2,4,6-trimethyl-4-phenyl-1,3-dioxane) | 1596 | −1.1 |
| GIVESCONE (ethyl 2-ethyl-6,6-dimethylcyclohex-2-enecarboxylate) | 1754 | −1.5 |
| TERPINENE GAMMA (1-methyl-4-propan-2-ylcyclohexa-1,4-diene) | 1205 | −0.4 |
| FIXOLIDE (1-(3,5,5,6,8,8-hexamethyl-5,6,7,8-tetrahydronaphthalen-2-yl)ethanone) | 2207 | −2.2 |
| CITRAL LEMAROME N ((E)-3,7-dimethylocta-2,6-dienal) | 1311 | −2.1 |
| METHYL CEDRYL KETONE (1-((1S,8aS)-1,4,4,6-tetramethyl-2,3,3a,4,5,8-hexahydro-1H-5,8a-methanoazulen-7-yl)ethanone) | 2076 | −1.9 |
| PARADISAMIDE (2-ethyl-N-methyl-N-(m-tolyl)butanamide) | 1790 | −3.0 |
| RASPBERRY KETONE (N112) (4-(4-hydroxyphenyl)butan-2-one) | 1243 | −2.4 |
| ROSYRANE SUPER (4-methylene-2-phenyltetrahydro-2H-pyran) | 1353 | −1.8 |
| NEOFOLIONE ((E)-methyl non-2-enoate) | 1418 | −2.1 |
| APHERMATE (1-(3,3-dimethylcyclohexyl)ethyl formate) | 1549 | −1.9 |
| CARYOPHYLLENE ((Z)-4,11,11-trimethyl-8-methylenebicyclo[7.2.0]undec-4-ene) | 1809 | −1.0 |
| STEMONE ((E)-5-methylheptan-3-one oxime) | 1250 | −1.7 |
| EBANOL ((E)-3-methyl-5-(2,2,3-trimethylcyclopent-3-en-1-yl)pent-4-en-2-ol) | 1832 | −2.5 |
| CYCLOMYRAL (8,8-dimethyl-1,2,3,4,5,6,7,8-octahydronaphthalene-2-carbaldehyde) | 1610 | −2.4 |
| FENCHYL ACETATE ((2S)-1,3,3-trimethylbicyclo[2.2.1]heptan-2-yl acetate) | 1628 | −2.2 |
| JASMONE CIS ((Z)-3-methyl-2-(pent-2-en-1-yl)cyclopent-2-enone) | 1379 | −1.7 |
| METHYL NONYL KETONE EXTRA (undecan-2-one) | 1532 | −1.8 |
| SYLKOLIDE ((E)-2-((3,5-dimethylhex-3-en-2-yl)oxy)-2-methylpropyl cyclopropanecarboxylate) | 2177 | −1.9 |

-continued

| Perfumery ingredient | RECON_VOLTAE (Bohr3) | LogKcaps |
|---|---|---|
| MELONAL (2,6-dimethylhept-5-enal) | 1229 | −2.0 |
| BUTYL BUTYRO LACTATE (1-butoxy-1-oxopropan-2-yl butyrate) | 1680 | −0.1 |
| ALDEHYDE ISO C 11 ((E)-undec-9-enal) | 1491 | −3.0 |
| DAMASCENONE GIV ((E)-1-(2,6,6-trimethylcyclohexa-1,3-dien-1-yl)but-2-en-1-one) | 1608 | −1.5 |
| ROSALVA (dec-9-en-1-ol) | 1397 | −2.6 |
| VIRIDINE ((2,2-dimethoxyethyl)benzene) | 1281 | −2.7 |
| FRUITATE ((3aS,4S,7R,7aS)-ethyl octahydro-1H-4,7-methanoindene-3a-carboxylate) | 1617 | −1.1 |
| CITRONELLYL FORMATE (3,7-dimethyloct-6-en-1-yl formate) | 1544 | −1.9 |
| EUCALYPTOL ((1s,4s)-1,3,3-trimethyl-2-oxabicyclo[2.2.2]octane) | 1278 | −1.0 |
| IRONE ALPHA ((E)-4-(2,5,6,6-tetramethylcyclohex-2-en-1-yl)but-3-en-2-one) | 1800 | −1.5 |
| MENTHONE (2-isopropyl-5-methylcyclohexanone) | 1312 | −1.4 |
| HEXENYL-3-CIS BUTYRATE ((Z)-hex-3-en-1-yl butyrate) | 1421 | −1.2 |
| ALDEHYDE C 11 MOA (2-methyldecanal) | 1530 | −2.6 |
| CLONAL (dodecanenitrile) | 1723 | −1.0 |
| DAMASCONE ALPHA ((E)-1-(2,6,6-trimethylcyclohex-2-en-1-yl)but-2-en-1-one) | 1657 | −1.1 |
| DECENAL-4-TRANS ((E)-dec-4-enal) | 1363 | −2.8 |
| DUPICAL ((E)-4-((3aS,7aS)-hexahydro-1H-4,7-methanoinden-5(6H)-ylidene)butanal) | 1607 | −2.5 |
| FENCHYL ALCOHOL ((1S,2R,4R)-1,3,3-trimethylbicyclo[2.2.1]heptan-2-ol) | 1345 | −2.0 |
| INDOFLOR (4,4a,5,9b-tetrahydroindeno[1,2-d][1,3]dioxine) | 1245 | −2.7 |
| MALTYL ISOBUTYRATE (2-methyl-4-oxo-4H-pyran-3-yl isobutyrate) | 1398 | −0.1 |
| METHYL OCTYNE CARBONATE (methyl non-2-ynoate) | 1376 | −1.8 |
| PELARGENE (2-methyl-4-methylene-6-phenyltetrahydro-2H-pyran) | 1480 | −1.5 |
| PYRALONE (6-(sec-butyl)quinoline) | 1466 | −1.8 |
| SUPER MUGUET ((E)-6-ethyl-3-methyloct-6-en-1-ol) | 1522 | −2.7 |
| VELOUTONE (2,2,5-trimethyl-5-pentylcyclopentanone) | 1778 | −1.9 |
| RHUBAFURANE (2,2,5-trimethyl-5-pentylcyclopentanone) | 1434 | −1.9 |
| SPIROGALBANONE (1-(spiro[4.5]dec-6-en-7-yl)pent-4-en-1-one) | 1850 | −2.0 |
| DIHYDRO ANETHOLE (propanedioic acid 1-(1-(3,3-dimethylcyclohexyl)ethyl) 3-ethyl ester) | 1219 | −1.7 |
| ZINARINE (2-(2,4-dimethylcyclohexyl)pyridine) | 1557 | −2.1 |
| BIGARYL (8-(sec-butyl)-5,6,7,8-tetrahydroquinoline) | 1563 | −2.0 |
| CASSYRANE (5-tert-butyl-2-methyl-5-propyl-2H-furan) | 1624 | −1.6 |
| MANZANATE (ethyl 2-methylpentanoate) | 1202 | −1.4 |
| NONENAL-6-CIS ((Z)-non-6-enal) | 1234 | −2.5 |
| ALLYL AMYL GLYCOLATE (allyl 2-(isopentyloxy)acetate) | 1495 | −2.2 |
| DIHYDRO JASMONE (3-methyl-2-pentylcyclopent-2-enone) | 1409 | −1.7 |
| ISOCYCLOCITRAL (2,4,6-trimethylcyclohex-3-enecarbaldehyde) | 1266 | −1.8 |
| LEAF ACETAL ((Z)-1-(1-ethoxyethoxy)hex-3-ene) | 1457 | −0.7 |
| CYCLOGALBANATE (allyl 2-(cyclohexyloxy)acetate) | 1546 | −2.4 |
| LIFFAROME GIV ((Z)-hex-3-en-1-yl methyl carbonate) | 1218 | −1.5 |
| CITRATHAL R ((Z)-1,1-diethoxy-3,7-dimethylocta-2,6-diene) | 1933 | −1.1 |
| ROSYFOLIA ((1-methyl-2-(5-methylhex-4-en-2-yl)cyclopropyl)-methanol) | 1685 | −1.0 |
| (3-(4-isobutyl-2-methylphenyl)propanal) | 1700 | −2.5 |

When encapsulated in the amounts referred to hereinabove in accordance with the present invention, encapsulated perfume compositions containing perfume ingredients of GROUP 1 exhibit superior resistance to leakage when suspended in mildly extractive media, such as those encountered in fabric softener or conditioning compositions, and particularly those compositions containing structured surfactants.

Those encapsulated perfume compositions described hereinabove containing perfume ingredients characterized by a RECON_VOLTAE value larger than about 1200 Bohr$^3$, wherein those ingredients are additionally characterized by a $\log_{10}$ Kcaps greater than −3 (i.e. GROUP 1 ingredients) form additional embodiments of the present invention.

Furthermore, fabric softener or conditioning compositions, particularly those containing structured surfactants, containing said encapsulated perfume compositions form further embodiments of the present invention.

A second group of perfume ingredients, so called GROUP 2 ingredients, have RECON_VOLTAE values larger than 1540 Bohr$^3$ and $\log_{10}$ Kcaps greater than −3. Perfume ingredients of GROUP 2 include but are not limited to

| Perfumery ingredient | RECON_VOLTAE (Bohr3) | LogKcaps |
|---|---|---|
| HEDIONE (methyl 3-oxo-2-pentylcyclopentaneacetate) | 1784 | −2.4 |
| ALLYL CYCLOHEXYL PROPIONATE (allyl 3-cyclohexylpropanoate) | 1606 | −2.0 |
| AGRUMEX (2-(tert-butyl)cyclohexyl acetate) | 1678 | −1.9 |
| IRISONE ALPHA ((E)-4-(2,6,6-trimethylcyclohex-2-en-1-yl)but-3-en-2-one) | 1676 | −1.8 |
| ISO E SUPER (1-(2,3,8,8-tetramethyl-1,2,3,4,5,6,7,8-octahydronaphthalen-2-yl)ethanone) | 2024 | −1.4 |
| ISORALDEINE 70 ((E)-3-methyl-4-(2,6,6-trimethylcyclohex-2-en-1-yl)but-3-en-2-one) | 1806 | −2.0 |
| NECTARYL (2-(2-(4-methylcyclohex-3-en-1-yl)propyl)cyclopentanone) | 1822 | −1.9 |
| BOISAMBRENE FORTE ((ethoxymethoxy)cyclododecane) | 2063 | −2.0 |
| BOISIRIS ((1S,2R,5R)-2-ethoxy-2,6,6-trimethyl-9-methylenebicyclo[3.3.1]nonane) | 1914 | −1.0 |
| FLOROCYCLENE ((3aR,6S,7aS)-3a,4,5,6,7,7a-hexahydro-1H-4,7-methanoinden-6-yl propionate) | 1549 | −1.6 |
| HEXYL SALICYLATE (hexyl 2-hydroxybenzoate) | 1685 | −1.6 |
| ALDEHYDE C 12 MNA PURE (2-methylundecanal) | 1661 | −2.3 |
| BUTYL CYCLOHEXYL ACETATE PARA (4-(tert-butyl)cyclohexyl acetate) | 1682 | −2.7 |
| DAMASCONE DELTA ((E)-1-(2,6,6-trimethylcyclohex-3-en-1-yl)but-2-en-1-one) | 1654 | −1.3 |
| DIMETHYL BENZYL CARBINYL BUTYRATE (2-methyl-1-phenylpropan-2-yl butyrate) | 1767 | −1.6 |
| HEXYL CINNAMIC ALDEHYDE ((E)-2-benzylideneoctanal) | 1778 | −2.5 |
| IONONE BETA ((E)-4-(2,6,6-trimethylcyclohex-1-en-1-yl)but-3-en-2-one) | 1670 | −1.6 |
| TERPINYL ACETATE (2-(4-methylcyclohex-3-en-1-yl)propan-2-yl acetate) | 1590 | −2.0 |
| GARDOCYCLENE ((3aR,6S,7aS)-3a,4,5,6,7,7a-hexahydro-1H-4,7-methanoinden-6-yl isobutyrate) | 1677 | −1.5 |
| IRISONE PURE ((E)-4-(2,6,6-trimethylcyclohex-2-en-1-yl)but-3-en-2-one) | 1676 | −1.8 |
| LILIAL (3-(4-(tert-butyl)phenyl)-2-methylpropanal) | 1738 | −2.0 |
| LINALYL ACETATE SYNTHETIC (3,7-dimethylocta-1,6-dien-3-yl acetate) | 1653 | −1.5 |
| PETALIA (2-cyclohexylidene-2-(o-tolyl)acetonitrile) | 1753 | −1.4 |
| NEOBERGAMATE FORTE (2-methyl-6-methyleneoct-7-en-2-yl acetate) | 1650 | −1.4 |
| ISONONYL ACETATE PURE (3,5,5-trimethylhexyl acetate) | 1632 | −1.0 |
| NONADYL (6,8-dimethylnonan-2-ol) | 1579 | −1.8 |
| METHYL PAMPLEMOUSSE (6,6-dimethoxy-2,5,5-trimethylhex-2-ene) | 1632 | −1.9 |
| AMBER CORE (1-((2-(tert-butyl)cyclohexyl)oxy)butan-2-ol) | 1972 | −2.3 |
| CASHMERAN (1,1,2,3,3-pentamethyl-2,3,6,7-tetrahydro-1H-inden-4(5H)-one) | 1772 | −1.9 |

| Perfumery ingredient | RECON_VOLTAE (Bohr3) | LogKcaps |
|---|---|---|
| DAMASCENONE ((E)-1-(2,6,6-trimethylcyclohexa-1,3-dien-1-yl)but-2-en-1-one) | 1608 | −1.5 |
| ETHYL SAFRANATE (ethyl 2,6,6-trimethylcyclohexa-1,3-diene-1-carboxylate) | 1579 | −2.0 |
| PEONILE (2-cyclohexylidene-2-phenylacetonitrile) | 1633 | −0.9 |
| SILVIAL (3-(4-isobutylphenyl)-2-methylpropanal) | 1700 | −2.5 |
| CITRONELLYL PROPIONATE (3,7-dimethyloct-6-en-1-yl propionate) | 1808 | −2.0 |
| CYCLOHEXYL SALICYLATE (cyclohexyl 2-hydroxybenzoate) | 1610 | −2.2 |
| BORNYL ACETATE ((2S,4S)-1,7,7-trimethylbicyclo[2.2.1]heptan-2-yl acetate) | 1631 | −1.8 |
| ALDEHYDE MANDARINE ((E)-dodec-2-enal) | 1615 | −2.7 |
| AMBERMAX (1,3,4,5,6,7-hexahydro-.beta.,1,1,5,5-pentamethyl-2H-2,4a-Methanonaphthalene-8-ethanol) | 2275 | −2.8 |
| BELAMBRE 50%/IPM ((1R,2S,4R)-2'-isopropyl-1,7,7-trimethylspiro[bicyclo[2.2.1]heptane-2,4'-[1,3]dioxane]) | 2112 | −1.6 |
| FLORHYDRAL (3-(3-isopropylphenyl)butanal) | 1568 | −2.7 |
| GERANYL ACETATE SYNTHETIC ((E)-3,7-dimethylocta-2,6-dien-1-yl acetate) | 1643 | −2.4 |
| HABANOLIDE ((E)-oxacyclohexadec-12-en-2-one) | 1978 | −2.6 |
| MYRALDENE (4-(4-methylpent-3-en-1-yl)cyclohex-3-enecarbaldehyde) | 1613 | −2.2 |
| TRIDECENE-2-NITRILE ((E)-tridec-2-enenitrile) | 1818 | −1.5 |
| ROSACETOL (2,2,2-trichloro-1-phenylethyl acetate) | 1731 | −1.5 |
| CITRONELLYL ACETATE (3,7-dimethyloct-6-en-1-yl acetate) | 1678 | −1.7 |
| GERANYL ISOBUTYRATE ((E)-3,7-dimethylocta-2,6-dien-1-yl isobutyrate) | 1901 | −1.2 |
| RADJANOL SUPER ((E)-2-ethyl-4-(2,2,3-trimethylcyclopent-3-en-1-yl)but-2-en-1-ol) | 1829 | −2.3 |
| ETHYL LINALYL ACETATE ((Z)-3,7-dimethylnona-1,6-dien-3-yl acetate) | 1783 | −1.1 |
| SERENOLIDE (2-(1-(3,3-dimethylcyclohexyl)ethoxy)-2-methylpropyl cyclopropanecarboxylate) | 2429 | −2.0 |
| GALBANONE PURE (1-(3,3-dimethylcyclohex-1-en-1-yl)pent-4-en-1-one) | 1663 | −1.9 |
| KOAVONE ((Z)-3,4,5,6,6-pentamethylhept-3-en-2-one) | 1675 | −1.6 |
| NEROLIDYLE ((Z)-3,7,11-trimethyldodeca-1,6,10-trien-3-yl acetate) | 2257 | −2.3 |
| ADOXAL (2,6,10-trimethylundec-9-enal) | 1878 | −2.5 |
| ALDEHYDE C 12 LAURIC (dodecanal) | 1662 | −2.9 |
| COSMONE ((Z)-3-methylcyclotetradec-5-enone) | 1924 | −2.5 |
| CYCLAMEN ALDEHYDE (3-(4-isopropylphenyl)-2-methylpropanal) | 1567 | −1.6 |
| FLORALOZONE (3-(4-ethylphenyl)-2,2-dimethylpropanal) | 1608 | −1.9 |
| HERBANATE ((2S)-ethyl 3-isopropylbicyclo[2.2.1]hept-5-ene-2-carboxylate) | 1629 | −0.7 |
| PIVAROSE (2,2-dimethyl-2-pheylethyl propanoate) | 1665 | −2.5 |
| PRECYCLEMONE B (1-methyl-4-(4-methylpent-3-en-1-yl)cyclohex-3-enecarbaldehyde) | 1783 | −2.2 |
| CITRONELLYL ACETATE (3,7-dimethyloct-6-en-1-yl acetate) | 1678 | −1.7 |

-continued

| Perfumery ingredient | RECON_VOLTAE (Bohr3) | LogKcaps |
|---|---|---|
| KARANAL (5-(sec-butyl)-2-(2,4-dimethylcyclohex-3-en-1-yl)-5-methyl-1,3-dioxane) | 2242 | −1.4 |
| NERYL ACETATE HC ((Z)-3,7-dimethylocta-2,6-dien-1-yl acetate) | 1643 | −2.4 |
| THIBETOLIDE (oxacyclohexadecan-2-one) | 2017 | −2.2 |
| FLOROPAL (2,4,6-trimethyl-4-phenyl-1,3-dioxane) | 1596 | −1.1 |
| GIVESCONE (ethyl 2-ethyl-6,6-dimethylcyclohex-2-enecarboxylate) | 1754 | −1.5 |
| FIXOLIDE (1-(3,5,5,6,8,8-hexamethyl-5,6,7,8-tetrahydronaphthalen-2-yl)ethanone) | 2207 | −2.2 |
| METHYL CEDRYL KETONE (1-((1S,8aS)-1,4,4,6-tetramethyl-2,3,3a,4,5,8-hexahydro-1H-5,8a-methanoazulen-7-yl)ethanone) | 2076 | −1.9 |
| PARADISAMIDE (2-ethyl-N-methyl-N-(m-tolyl)butanamide) | 1790 | −3.0 |
| CARYOPHYLLENE ((Z)-4,11,11-trimethyl-8-methylenebicyclo[7.2.0]undec-4-ene) | 1809 | −1.0 |
| EBANOL ((E)-3-methyl-5-(2,2,3-trimethylcyclopent-3-en-1-yl)pent-4-en-2-ol) | 1832 | −2.5 |
| CYCLOMYRAL (8,8-dimethyl-1,2,3,4,5,6,7,8-octahydronaphthalene-2-carbaldehyde) | 1610 | −2.4 |
| FENCHYL ACETATE ((2S)-1,3,3-trimethylbicyclo[2.2.1]heptan-2-yl acetate) | 1628 | −2.2 |
| SYLKOLIDE ((E)-2-((3,5-dimethylhex-3-en-2-yl)oxy)-2-methylpropyl cyclopropanecarboxylate) | 2177 | −1.9 |
| BUTYL BUTYRO LACTATE (1-butoxy-1-oxopropan-2-yl butyrate) | 1680 | −0.1 |
| DAMASCENONE GIV ((E)-1-(2,6,6-trimethylcyclohexa-1,3-dien-1-yl)but-2-en-1-one) | 1608 | −1.5 |
| FRUITATE ((3aS,4S,7R,7aS)-ethyl octahydro-1H-4,7-methanoindene-3a-carboxylate) | 1617 | −1.1 |
| IRONE ALPHA ((E)-4-(2,5,6,6-tetramethylcyclohex-2-en-1-yl)but-3-en-2-one) | 1800 | −1.5 |
| CLONAL (dodecanenitrile) | 1723 | −1.0 |
| DAMASCONE ALPHA ((E)-1-(2,6,6-trimethylcyclohex-2-en-1-yl)but-2-en-1-one) | 1657 | −1.1 |
| DUPICAL ((E)-4-((3aS,7aS)-hexahydro-1H-4,7-methanoinden-5(6H)-ylidene)butanal) | 1607 | −2.5 |
| VELOUTONE (2,2,5-trimethyl-5-pentylcyclopentanone) | 1778 | −1.9 |
| SPIROGALBANONE (1-(spiro[4.5]dec-6-en-7-yl)pent-4-en-1-one) | 1850 | −2.0 |
| ZINARINE (2-(2,4-dimethylcyclohexyl)pyridine) | 1557 | −2.1 |
| BIGARYL (8-(sec-butyl)-5,6,7,8-tetrahydroquinoline) | 1563 | −2.0 |
| CASSYRANE (5-tert-butyl-2-methyl-5-propyl-2H-furan) | 1624 | −1.6 |
| CITRATHAL R ((Z)-1,1-diethoxy-3,7-dimethylocta-2,6-diene) | 1933 | −1.1 |
| ROSYFOLIA ((1-methyl-2-(5-methylhex-4-en-2-yl)cyclopropyl)-methanol) | 1685 | −1.0 |
| (3-(4-isobutyl-2-methylphenyl)propanal) | 1700 | −2.5 |

Encapsulated perfume compositions containing GROUP 2 perfume ingredients in the amounts referred to herein above are resistant to leakage when suspended in harshly extractive media, such as solid and liquid laundry care detergents.

Those encapsulated perfume compositions described hereinabove containing perfume ingredients characterized by a RECON_VOLTAE value larger than about 1540 Bohr$^3$, wherein those ingredients are additionally characterized by having a $\log_{10}$ Kcaps greater than −3 (i.e. GROUP 2 ingredients) form additional embodiments of the present invention.

Furthermore, solid or liquid laundry detergent compositions, and particular those formats designed as unit dosage forms contained in pouches or pods, and often referred to in the art as "liquid tabs", containing said encapsulated perfume compositions form further embodiments of the present invention.

A GROUP 3 of perfume ingredients is characterized by ingredients having RECON_VOLTAE values larger than 1750 Bohr$^3$ and $\log_{10}$ Kcaps greater than −3. Perfume ingredients of GROUP 3 include but are not limited to:

| Perfumery ingredient | RECON_VOLTAE (Bohr3) | LogKcaps |
|---|---|---|
| ADOXAL (2,6,10-trimethylundec-9-enal) | 1878 | −2.5 |
| AMBER CORE (1-((2-(tert-butyl)cyclohexyl)oxy)butan-2-ol) | 1972 | −2.3 |
| AMBERMAX (1,3,4,5,6,7-hexahydro-.beta.,1,1,5,5-pentamethyl-2H-2,4a-Methanonaphthalene-8-ethanol) | 2275 | −2.8 |
| AMBROCENIDE ((4aR,5R,7aS,9R)-Octahydro-2,2,5,8,8,9a-hexamethyl-4H-4a,9-methanoazuleno[5,6-d]-1,3-dioxole) | 2339 | −2.1 |
| BELAMBRE ((1R,2S,4R)-2'-isopropyl-1,7,7-trimethylspiro[bicyclo[2.2.1]heptane-2,4'-[1,3]dioxane]) | 2112 | −1.6 |
| BOISAMBRENE FORTE ((ethoxymethoxy)cyclododecane) | 2063 | −2.0 |
| BOISIRIS ((1S,2R,5R)-2-ethoxy-2,6,6-trimethyl-9-methylenebicyclo[3.3.1]nonane) | 1914 | −1.0 |
| CARYOPHYLLENE ((Z)-4,11,11-trimethyl-8-methylenebicyclo[7.2.0]undec-4-ene) | 1809 | −1.0 |
| CASHMERAN (1,1,2,3,3-pentamethyl-2,3,6,7-tetrahydro-1H-inden-4(5H)-one) | 1772 | −1.9 |
| CITRONELLYL PROPIONATE (3,7-dimethyloct-6-en-1-yl propionate) | 1808 | −2.0 |
| COSMONE ((Z)-3-methylcyclotetradec-5-enone) | 1924 | −2.5 |
| DIMETHYL BENZYL CARBINYL BUTYRATE (2-methyl-1-phenylpropan-2-yl butyrate) | 1767 | −1.6 |
| EBANOL ((E)-3-methyl-5-(2,2,3-trimethylcyclopent-3-en-1-yl)pent-4-en-2-ol) | 1832 | −2.5 |
| ETHYL LINALYL ACETATE ((Z)-3,7-dimethylnona-1,6-dien-3-yl acetate) | 1783 | −1.1 |
| FIXOLIDE (1-(3,5,5,6,8,8-hexamethyl-5,6,7,8-tetrahydronaphthalen-2-yl)ethanone) | 2207 | −2.2 |
| GERANYL ISOBUTYRATE ((E)-3,7-dimethylocta-2,6-dien-1-yl isobutyrate) | 1901 | −1.2 |
| GIVESCONE (ethyl 2-ethyl-6,6-dimethylcyclohex-2-enecarboxylate) | 1754 | −1.5 |
| HABANOLIDE ((E)-oxacyclohexadec-12-en-2-one) | 1978 | −2.6 |
| HEDIONE (methyl 3-oxo-2-pentylcyclopentaneacetate) | 1784 | −2.4 |
| HEXYL CINNAMIC ALDEHYDE ((E)-2-benzylideneoctanal) | 1778 | −2.5 |
| IRONE ALPHA ((E)-4-(2,5,6,6-tetramethylcyclohex-2-en-1-yl)but-3-en-2-one) | 1800 | −1.5 |
| ISO E SUPER (1-(2,3,8,8-tetramethyl-1,2,3,4,5,6,7,8-octahydronaphthalen-2-yl)ethanone) | 2024 | −1.4 |
| ISORALDEINE 70 ((E)-3-methyl-4-(2,6,6-trimethylcyclohex-2-en-1-yl)but-3-en-2-one) | 1806 | −2.0 |
| KARANAL (5-(sec-butyl)-2-(2,4-dimethylcyclohex-3-en-1-yl)-5-methyl-1,3-dioxane) | 2242 | −1.4 |
| METHYL CEDRYL KETONE (1-((1S,8aS)-1,4,4,6-tetramethyl-2,3,3a,4,5,8-hexahydro-1H-5,8a-methanoazulen-7-yl)ethanone) | 2076 | −1.9 |
| NECTARYL (2-(2-(4-methylcyclohex-3-en-1-yl)propyl)cyclopentanone) | 1822 | −1.9 |
| NEROLIDYLE ((Z)-3,7,11-trimethyldodeca-1,6,10-trien-3-yl acetate) | 2257 | −2.3 |
| PARADISAMIDE (2-ethyl-N-methyl-N-(m-tolyl)butanamide) | 1790 | −3.0 |
| PETALIA (2-cyclohexylidene-2-(o-tolyl)acetonitrile) | 1753 | −1.4 |
| PRECYCLEMONE B (1-methyl-4-(4-methylpent-3-en-1-yl)cyclohex-3-enecarbaldehyde) | 1783 | −2.2 |
| RADJANOL SUPER ((E)-2-ethyl-4-(2,2,3-trimethylcyclopent-3-en-1-yl)but-2-en-1-ol) | 1829 | −2.3 |
| SERENOLIDE (2-(1-(3,3-dimethylcyclohexyl)ethoxy)-2-methylpropyl cyclopropanecarboxylate) | 2429 | −2.0 |
| SYLKOLIDE ((E)-2-((3,5-dimethylhex-3-en-2-yl)oxy)-2-methylpropyl cyclopropanecarboxylate) | 2177 | −1.9 |

| Perfumery ingredient | RECON_VOLTAE (Bohr3) | LogKcaps |
| --- | --- | --- |
| THIBETOLIDE (oxacyclohexadecan-2-one) | 2017 | −2.2 |
| TRIDECENE-2-NITRILE ((E)-tridec-2-enenitrile) | 1818 | −2.2 |
| VELOUTONE (2,2,5-trimethyl-5-pentylcyclopentanone) | 1778 | −1.9 |
| SPIROGALBANONE (1-(spiro[4.5]dec-6-en-7-yl)pent-4-en-1-one) | 1850 | −2.0 |
| CITRATHAL R ((Z)-1,1-diethoxy-3,7-dimethylocta-2,6-diene) | 1933 | −1.1 |

Encapsulated perfume compositions containing perfume ingredients of GROUP 3 in amounts referred to hereinabove, are resistant to leakage when suspended in harshly extractive media, such as encountered in shampoos and personal care cleansing compositions.

Those encapsulated perfume compositions described hereinabove containing perfume ingredients characterized by a RECON_VOLTAE value larger than about 1200 Bohr$^3$, wherein those ingredients are additionally characterized by having a $\log_{10}$ Kcaps greater than −3 (i.e. GROUP 3 ingredients) form additional embodiments of the present invention.

Furthermore, personal care cleansing compositions, including shampoos and hair conditioners, containing said encapsulated perfume compositions form still further embodiments of the present invention.

A particular challenge that faces formulators of encapsulated perfume compositions is how to strike an acceptable balance between microcapsule stability (i.e. the resistance to leakage of perfume ingredients from microcapsules dispersed in a suspending medium) and performance, (that is, the ability of a microcapsule to deliver a perfume impression once deposited on a substrate). Typically, if microcapsules are particularly stable during storage in extractive bases, then they tend to be rather robust and will only release perfume, if at all, upon application of high shear forces. When such microcapsules are deposited on substrates, such as fabric, hair or skin, a perfume impression may only be noticeable with vigorous rubbing of the treated substrate. Such microcapsules are said to possess "post-rub" performance, but often their pre-rub odour impression is weak or non-existent.

The provision of stable microcapsules, and particularly microcapsules that are stable in aggressive or extractive media, that exhibit acceptable pre-rub odour impression remains challenging.

The present invention articulates another physicochemical parameter that correlates well with performance, and particularly the pre-rub odour impression of perfume ingredients encapsulated in core shell microcapsules.

The intrinsic Pre-Rub Odour Contribution ("PROC") of a perfume ingredient is given by the concentration (wt %) of a perfume ingredient to be encapsulated, multiplied by its standard Odour Value ($OV_i$), and by its equilibrium headspace-capsule partition coefficient Kcaps. Hence for each perfume ingredient i, a Pre-Rub Odour Contribution is defined by $$PROC_i = OV_i[\log_{10} Kcaps_i + 3]$$

Furthermore, the partial Pre-Rub Odour Contribution (pPROC) of an ingredient is defined as its concentration (wt %) in the perfume multiplied by its standard Odour Value ($OV_i$) and by its equilibrium headspace-capsule partition coefficient Kcaps. Hence for each perfume ingredient i, a partial Pre-Rub Odour Contribution is defined by $$pPROC_i = c_i OV_i[\log_{10} Kcaps_i + 3]$$

Finally, the total Pre-Rub Odour Contribution (tPROC) is the sum of the partial Pre-Rub Odour Contribution (pPROC) over all ingredients in an encapsulated perfume composition.

The standard Odour Value ($OV_i$) is defined as the ratio of the standard equilibrium headspace concentration of the ingredient to the Odour Detection Threshold of this ingredient.

The term "standard equilibrium headspace concentration" used hereinabove refers to the concentration of a perfume ingredient in equilibrium with its condensed form (that is, its solid or liquid form) at a temperature of 25° C. and under a pressure of 1 atmosphere. It can be measured by using any of the quantitative headspace analysis techniques known in the art, see for example Mueller and Lamparsky in Perfumes: Art, Science and Technology, Chapter 6 "The Measurement of Odors" at pages 176-179 (Elsevier 1991).

The term Odour Detection Threshold ($ODT_i$) used herein refers to the average concentration above which a perfume ingredient i can be perceived by a panellist and can be measured by olfactometry, as described, for example in Mueller and Lamparsky (op. cit).

The equilibrium headspace concentration may be measured as follows: 500 mg of the test compound is added to a headspace container which is then sealed. The container is then incubated at constant 25° C. until the compound reached equilibrium between the gas and the liquid phase. A defined volume of this saturated headspace (usually 0.5-1 l) is trapped on a micro filter using a styrene/divinyl benzene porous material, such as Porapak™ Q (available from Sigma-Aldrich) as sorbent. After filter extraction with an appropriate solvent (usually 30-100 ul methyl tert. butyl ether), an aliquot of the extract is analyzed by gas chromatography (GC). Quantification is performed by the external standard calibration method. The concentration in the original headspace can be calculated (in terms of µg/l) from the headspace volume sucked through the micro filter and the aliquot of the filter extract injected into the gas chromatograph. The final headspace concentration value of a given test compound is obtained as the mean value of three independent measurements. Further information of the technique hereinabove described may be found in the article of Etzweiler, F.; Senn E. and Neuner-Jehle N., Ber. Bunsen-Ges. Phys. Chem. 1984, 88, 578-583, which is hereby incorporated by reference.

The Odour Detection Threshold ($ODT_i$) may be measured by using an olfactometer. The following steps can be carried out and the odor thresholds for each compounds listed in Table 1 determined.

The olfactometer functions on the principle of a linear dilution of an odorant in a carrier gas. The quantity of odorant displaced depends on its vapor pressure and the carrier gas flow. A constant flow of nitrogen, regulated by a flow regulator, carries the odorant from a sample container to a mixing chamber. There, the carrier gas-odor mixture is diluted with odourless air. From the mixing chamber one part of the diluted odorous air is allowed to flow via a fused silica capillary to the sniffing funnel. The flow rate through the capillary, which determines the dosage of odorous air from the mixing chamber into the sniffing funnel, depends on the opening the valve which can be regulated via PC from 1 to 256 ml in binary steps. The final dilution of the odorous air sample occurs in the glass funnel by flushing them permanently with odourless air at a flow rate of 8 lt/min. Forced-choice triangle presentation is achieved by a special automated channel setting device where only one position of a switch the odorant delivering capillary enters in the sniffing funnel, whereas in two other positions the capillary is positioned outside the funnel and where the effluent is sucked away. After each trial the channel setting is changed automatically and in a random order. The concentration is calculated from the odorants vapour pressure and from the dilution ratios that were applied in the olfactometer, assuming that vapour pressure saturation is achieved in the sample generator. As a control the concentration is determined analytically by sampling a known volume from the capillary effluent into a headspace filter and by subsequent gas chromatographic quantitation of the odourant in the desorption solution.

Each panellist (panel of 15 persons) starts sniffing at the olfactometer at a concentration level at which he perceives the odorant at medium intensity. After three correct answers in three consecutive trials (or four correct answers of five trials) at the same level, stimulus concentration is decreased by a factor of two to the next lower level, and so on, until the panellist has reached his threshold level. The final threshold value of a given odorant is obtained as the mean value of all individual threshold levels.

Encapsulated perfume compositions of the present invention displaying good pre-rub performance may be prepared by selecting perfume ingredients on the basis of their PROC values, such that the total Pre-Rub Odour Contribution of the perfume ingredients encapsulated in the composition is be between about $0.5 \times 10^8$ and $1.0 \times 10^9$, more particularly between $1 \times 10^8$ and $8 \times 10^8$ and more particularly still between $1.5 \times 10^8$ and $6 \times 10^8$.

Still further, in order to obtain encapsulated perfume compositions comprising core-shell microcapsules having optimal performance in terms of stability with respect to leakage, particularly in highly extractive/aggressive media and performance, in particular pre-rub performance, the perfume ingredients may be selected on the basis of their PROC values, such that the total Pre-Rub Odour Contribution of the perfume ingredients encapsulated in the composition should be between about $0.5 \times 10^8$ and $1 \times 10^9$, more particularly between $1 \times 10^8$ and $8 \times 10^8$ and more particularly still between $1.5 \times 10^8$ and $6 \times 10^8$, and the distribution of perfume ingredient RECON_VOLTAE and $\log_{10}$ Kcaps values are within the ranges as disclosed hereinabove.

A GROUP 4 of perfume ingredients, and their respective PROC values is listed in the Table below. It is preferred that encapsulated perfume compositions having high total PROC values are composed of the GROUP 4 ingredients specified herein below, although having regard to the teaching of the present invention, the skilled person may easily calculate the PROC values of other perfume ingredients not listed, and use them in encapsulated perfume compositions of the present invention.

GROUP 4 perfumery ingredients include but are not limited to:

| Perfumery ingredient | PROC |
| --- | --- |
| MANZANATE (ethyl 2-methylpentanoate) | 99577526 |
| DAMASCONE DELTA ((E)-1-(2,6,6-trimethylcyclohex-3-en-1-yl)but-2-en-1-one) | 65924274 |
| DAMASCENONE ((E)-1-(2,6,6-trimethylcyclohexa-1,3-dien-1-yl)but-2-en-1-one) | 33149935 |
| EUCALYPTOL ((1s,4s)-1,3,3-trimethyl-2-oxabicyclo[2.2.2]octane) | 20085069 |
| ETHYL CAPROATE (ethyl hexanoate) | 16063000 |
| NONENAL-6-CIS ((Z)-non-6-enal) | 14610000 |
| ALDEHYDE C 12 MNA (2-methylundecanal) | 6849504 |
| GALBANONE PURE (1-(3,3-dimethylcyclohex-1-en-1-yl)pent-4-en-1-one) | 4793532 |
| BIGARYL (8-(sec-butyl)-5,6,7,8-tetrahydroquinoline) | 4223123 |
| MELONAL (2,6-dimethylhept-5-enal) | 3633579 |
| DAMASCONE ALPHA ((E)-1-(2,6,6-trimethylcyclohex-2-en-1-yl)but-2-en-1-one) | 1869529 |
| ROSYRANE SUPER (4-methylene-2-phenyltetrahydro-2H-pyran) | 1841920 |
| PELARGENE (2-methyl-4-methylene-6-phenyltetrahydro-2H-pyran) | 1768363 |
| SPIROGALBANONE (1-(spiro[4.5]dec-6-en-7-yl)pent-4-en-1-one) | 1489842 |
| ETHYL SAFRANATE (ethyl 2,6,6-trimethylcyclohexa-1,3-diene-1-carboxylate) | 1446690 |
| DECENAL-4-TRANS ((E)-dec-4-enal) | 1068978 |
| CASSYRANE (5-tert-butyl-2-methyl-5-propyl-2H-furan) | 911423 |
| DELPHONE (2-pentylcyclopentanone) | 771798 |
| TERPINOLENE (1-methyl-4-(propan-2-ylidene)cyclohex-1-ene) | 672048 |
| IONONE BETA ((E)-4-(2,6,6-trimethylcyclohex-1-en-1-yl)but-3-en-2-one) | 668147 |
| ETHYL OENANTHATE (ethyl heptanoate) | 467433 |
| ALLYL AMYL GLYCOLATE (allyl 2-(isopentyloxy)acetate) | 448677 |
| LINALOOL (3,7-dimethylocta-1,6-dien-3-ol) | 405669 |
| ISOCYCLOCITRAL (2,4,6-trimethylcyclohex-3-enecarbaldehyde) | 362665 |
| ISOPROPYL METHYL-2-BUTYRATE (isopropyl 2-methyl butanoate) | 320608 |
| FLORHYDRAL (3-(3-isopropylphenyl)butanal) | 294597 |
| DIMETOL (2,6-dimethylheptan-2-ol) | 294170 |
| ROSYFOLIA (3-(4-isobutyl-2-methylphenyl)propanal) | 279858 |
| 3-(4-isobutyl-2-methylphenyl)propanal (3-(4-isobutyl-2-methylphenyl)propanal) | 279536 |

-continued

| Perfumery ingredient | PROC |
|---|---|
| METHYL OCTYNE CARBONATE (methyl non-2-ynoate) | 270258 |
| JASMACYCLENE ((3aR,6S,7aS)-3a,4,5,6,7,7a-hexahydro-1H-4,7-methanoinden-6-yl acetate) | 259747 |
| CYCLOGALBANATE (allyl 2-(cyclohexyloxy)acetate) | 220660 |
| FLOROPAL (2,4,6-trimethyl-4-phenyl-1,3-dioxane) | 215929 |
| DIPENTENE (1-methyl-4-(prop-1-en-2-yl)cyclohex-1-ene) | 189713 |
| FRUITATE ((3aS,4S,7R,7aS)-ethyl octahydro-1H-4,7-methanoindene-3a-carboxylate) | 176891 |
| METHYL PAMPLEMOUSSE (6,6-dimethoxy-2,5,5-trimethylhex-2-ene) | 151438 |
| IRISONE PURE ((E)-4-(2,6,6-trimethylcyclohex-2-en-1-yl)but-3-en-2-one) | 143717 |
| IRISONE ALPHA ((E)-4-(2,6,6-trimethylcyclohex-2-en-1-yl)but-3-en-2-one) | 143714 |
| LIFFAROME ((Z)-hex-3-en-1-yl methyl carbonate) | 141869 |
| CASHMERAN (1,1,2,3,3-pentamethyl-2,3,6,7-tetrahydro-1H-inden-4(5H)-one) | 141286 |
| TETRAHYDRO LINALOOL (3,7-dimethyloctan-3-ol) | 140812 |
| CITRONELLAL (3,7-dimethyloct-6-enal) | 126286 |
| ETHYL LINALOOL ((E)-3,7-dimethylnona-1,6-dien-3-ol) | 122602 |
| LEMONILE ((2E,6Z)-3,7-dimethylnona-2,6-dienenitrile) | 112447 |
| RHUBAFURAN (2,4-dimethyl-4-phenyltetrahydrofuran) | 109862 |
| FLOROCYCLENE ((3aR,6S,7aS)-3a,4,5,6,7,7a-hexahydro-1H-4,7-methanoinden-6-yl propionate) | 109419 |
| EBANOL ((E)-3-methyl-5-(2,2,3-trimethylcyclopent-3-en-1-yl)pent-4-en-2-ol) | 106853 |
| HEXENYL-3-CIS BUTYRATE ((Z)-hex-3-en-1-yl butyrate) | 97634 |
| ISORALDEINE 70 ((E)-3-methyl-4-(2,6,6-trimethylcyclohex-2-en-1-yl)but-3-en-2-one) | 83954 |
| MENTHONE (2-isopropyl-5-methylcyclohexanone) | 83516 |
| ETHYL CAPRYLATE (ethyl octanoate) | 81140 |
| GIVESCONE (ethyl 2-ethyl-6,6-dimethylcyclohex-2-enecarboxylate) | 76022 |
| CITRONELLYL NITRILE (3,7-dimethyloct-6-enenitrile) | 71124 |
| JASMONE CIS ((Z)-3-methyl-2-(pent-2-en-1-yl)cyclopent-2-enone) | 66032 |
| FENCHYL ALCOHOL ((1S,2R,4R)-1,3,3-trimethylbicyclo[2.2.1]heptan-2-ol) | 65384 |
| RADJANOL SUPER ((E)-2-ethyl-4-(2,2,3-trimethylcyclopent-3-en-1-yl)but-2-en-1-ol) | 64782 |
| UNDECAVERTOL ((E)-4-methyldec-3-en-5-ol) | 61799 |
| DUPICAL ((E)-4-((3aS,7aS)-hexahydro-1H-4,7-methanoinden-5(6H)-ylidene)butanal) | 60602 |
| BOISAMBRENE FORTE ((ethoxymethoxy)cyclododecane) | 59050 |
| ALDEHYDE C 11 MOA (2-methyldecanal) | 58883 |
| ISO E SUPER (1-(2,3,8,8-tetramethyl-1,2,3,4,5,6,7,8-octahydronaphthalen-2-yl)ethanone) | 52929 |
| DIMETHYL OCTENONE (4,7-dimethyloct-6-en-3-one) | 51879 |
| TERPINENE GAMMA (1-methyl-4-propan-2-ylcyclohexa-1,4-diene) | 51728 |
| FRESKOMENTHE (2-(sec-butyl)cyclohexanone) | 49849 |
| HEDIONE (methyl 3-oxo-2-pentylcyclopentaneacetate) | 47438 |
| CLONAL (dodecanenitrile) | 46090 |
| GARDOCYCLENE ((3aR,6S,7aS)-3a,4,5,6,7,7a-hexahydro-1H-4,7-methanoinden-6-yl isobutyrate) | 42816 |
| HERBANATE ((2S)-ethyl 3-isopropylbicyclo[2.2.1]hept-5-ene-2-carboxylate) | 38513 |
| LILIAL (3-(4-(tert-butyl)phenyl)-2-methylpropanal) | 32603 |
| SYLKOLIDE ((E)-2-((3,5-dimethylhex-3-en-2-yl)oxy)-2-methylpropyl cyclopropanecarboxylate) | 32277 |
| GERANIOL ((E)-3,7-dimethylocta-2,6-dien-1-ol) | 32071 |
| KOAVONE ((Z)-3,4,5,6,6-pentamethylhept-3-en-2-one) | 31805 |
| ROSACETOL (2,2,2-trichloro-1-phenylethyl acetate) | 31559 |
| CYCLAMEN ALDEHYDE (3-(4-isopropylphenyl)-2-methylpropanal) | 31268 |
| ALLYL CYCLOHEXYL PROPIONATE (allyl 3-cyclohexylpropanoate) | 29587 |
| BELAMBRE 50%/IPM ((1R,2S,4R)-2'-isopropyl-1,7,7-trimethylspiro[bicyclo[2.2.1]heptane-2,4'-[1,3]dioxane]) | 27187 |
| NONADYL (6,8-dimethylnonan-2-ol) | 26158 |
| FRUTONILE (2-methyldecanenitrile) | 24822 |
| TRIDECENE-2-NITRILE ((E)-tridec-2-enenitrile) | 24181 |
| PYRALONE (6-(sec-butyl)quinoline) | 23864 |
| STEMONE ((E)-5-methylheptan-3-one oxime) | 22947 |
| CITRAL LEMAROME N ((E)-3,7-dimethylocta-2,6-dienal) | 20039 |
| METHYL CEDRYL KETONE (1-((1S,8aS)-1,4,4,6-tetramethyl-2,3,3a,4,5,8-hexahydro-1H-5,8a-methanoazulen-7-yl)ethanone) | 19783 |
| ALDEHYDE C 110 UNDECYLIC (undecanal) | 18200 |
| SILVIAL (3-(4-isobutylphenyl)-2-methylpropanal) | 16666 |
| ALDEHYDE C 11 UNDECYLENIC (undec-10-enal) | 15988 |
| CITRONELLOL (3,7-dimethyloct-6-en-1-ol) | 15832 |
| ROSALVA (dec-9-en-1-ol) | 14982 |
| VELOUTONE (2,2,5-trimethyl-5-pentylcyclopentanone) | 14571 |
| MYRALDENE (4-(4-methylpent-3-en-1-yl)cyclohex-3-enecarbaldehyde) | 13927 |
| AMYL SALICYLATE (pentyl 2-hydroxybenzoate) | 13880 |

-continued

| Perfumery ingredient | PROC |
|---|---|
| TETRAHYDRO MYRCENOL (2,6-dimethyloctan-2-ol) | 13764 |
| BOISIRIS ((1S,2R,5R)-2-ethoxy-2,6,6-trimethyl-9-methylenebicyclo[3.3.1]nonane) | 13558 |
| NECTARYL (2-(2-(4-methylcyclohex-3-en-1-yl)propyl)cyclopentanone) | 13091 |
| METHYL NONYL KETONE EXTRA (undecan-2-one) | 11831 |
| PETALIA (2-cyclohexylidene-2-(o-tolyl)acetonitrile) | 10949 |
| FLORALOZONE (3-(4-ethylphenyl)-2,2-dimethylpropanal) | 10053 |
| PEONILE (2-cyclohexylidene-2-phenylacetonitrile) | 9995 |
| AGRUMEX (2-(tert-butyl)cyclohexyl acetate) | 9864 |
| IRONE ALPHA ((E)-4-(2,5,6,6-tetramethylcyclohex-2-en-1-yl)but-3-en-2-one) | 9686 |
| ORIVONE (4-(tert-pentyl)cyclohexanone) | 9146 |
| NEOBERGAMATE FORTE (2-methyl-6-methyleneoct-7-en-2-yl acetate) | 8351 |
| ISONONYL ACETATE (3,5,5-trimethylhexyl acetate) | 7732 |
| ALLYL OENANTHATE (allyl heptanoate) | 7580 |
| DIMETHYL BENZYL CARBINYL ACETATE (2-methyl-1-phenylpropan-2-yl acetate) | 7061 |
| COSMONE ((Z)-3-methylcyclotetradec-5-enone) | 6460 |
| SERENOLIDE (2-(1-(3,3-dimethylcyclohexyl)ethoxy)-2-methylpropyl cyclopropanecarboxylate) | 5947 |
| RASPBERRY KETONE (N112) (4-(4-hydroxyphenyl)butan-2-one) | 5860 |
| ETHYL LINALYL ACETATE ((Z)-3,7-dimethylnona-1,6-dien-3-yl acetate) | 5526 |
| DIMETHYL BENZYL CARBINYL BUTYRATE (2-methyl-1-phenylpropan-2-yl butyrate) | 5269 |
| MALTYL ISOBUTYRATE (2-methyl-4-oxo-4H-pyran-3-yl isobutyrate) | 5209 |
| HEXYL SALICYLATE (hexyl 2-hydroxybenzoate) | 4862 |
| AMBER CORE (1-((2-(tert-butyl)cyclohexyl)oxy)butan-2-ol) | 4356 |
| PRECYCLEMONE B (1-methyl-4-(4-methylpent-3-en-1-yl)cyclohex-3-enecarbaldehyde) | 4350 |
| HEXYL ISOBUTYRATE (hexyl isobutyrate) | 4190 |
| ADOXAL (2,6,10-trimethylundec-9-enal) | 3827 |
| THIBETOLIDE (oxacyclohexadecan-2-one) | 3525 |
| NEOFOLIONE ((E)-methyl non-2-enoate) | 3459 |
| TERPINYL ACETATE (2-(4-methylcyclohex-3-en-1-yl)propan-2-yl acetate) | 3429 |
| FENCHYL ACETATE ((2S)-1,3,3-trimethylbicyclo[2.2.1]heptan-2-yl acetate) | 3166 |
| SUPER MUGUET ((E)-6-ethyl-3-methyloct-6-en-1-ol) | 2813 |
| KARANAL (5-(sec-butyl)-2-(2,4-dimethylcyclohex-3-en-1-yl)-5-methyl-1,3-dioxane) | 2751 |
| CITRONELLYL PROPIONATE (3,7-dimethyloct-6-en-1-yl propionate) | 2710 |
| LINALYL ACETATE SYNTHETIC (3,7-dimethylocta-1,6-dien-3-yl acetate) | 2676 |
| BUTYL CYCLOHEXYL ACETATE PARA (4-(tert-butyl)cyclohexyl acetate) | 2526 |
| CYCLOHEXYL SALICYLATE (cyclohexyl 2-hydroxybenzoate) | 2454 |
| ALDEHYDE C 12 LAURIC (dodecanal) | 2369 |
| APHERMATE (1-(3,3-dimethylcyclohexyl)ethyl formate) | 2320 |
| GERANYL ISOBUTYRATE ((E)-3,7-dimethylocta-2,6-dien-1-yl isobutyrate) | 1972 |
| CITRONELLYL ACETATE (3,7-dimethyloct-6-en-1-yl acetate) | 1744 |
| ALDEHYDE MANDARINE ((E)-dodec-2-enal) | 1675 |
| BORNYL ACETATE ((2S,4S)-1,7,7-trimethylbicyclo[2.2.1]heptan-2-yl acetate) | 1498 |
| VIRIDINE ((2,2-dimethoxyethyl)benzene) | 1437 |
| CITRONELLYL FORMATE (3,7-dimethyloct-6-en-1-yl formate) | 1414 |
| PIVAROSE (2,2-dimethyl-2-pheylethyl propanoate) | 1206 |
| MENTHOL NATURAL (2-isopropyl-5-methylcyclohexanol) | 1177 |
| AMBERMAX (1,3,4,5,6,7-hexahydro-.beta.,1,1,5,5-pentamethyl-2H-2,4a-Methanonaphthalene-8-ethanol) | 1066 |
| BUTYL BUTYRO LACTATE (1-butoxy-1-oxopropan-2-yl butyrate) | 999 |
| CITRATHAL R ((Z)-1,1-diethoxy-3,7-dimethylocta-2,6-diene) | 995 |
| HABANOLIDE ((E)-oxacyclohexadec-12-en-2-one) | 991 |
| INDOFLOR (4,4a,5,9b-tetrahydroindeno[1,2-d][1,3]dioxine) | 830 |
| CORANOL (4-cyclohexyl-2-methylbutan-2-ol) | 740 |
| CARYOPHYLLENE ((Z)-4,11,11-trimethyl-8-methylenebicyclo[7.2.0]undec-4-ene) | 609 |
| GERANYL ACETATE ((E)-3,7-dimethylocta-2,6-dien-1-yl acetate) | 593 |
| PARADISAMIDE (2-ethyl-N-methyl-N-(m-tolyl)butanamide) | 550 |
| FIXOLIDE (1-(3,5,5,6,8,8-hexamethyl-5,6,7,8-tetrahydronaphthalen-2-yl)ethanone) | 550 |
| NERYL ACETATE HC ((Z)-3,7-dimethylocta-2,6-dien-1-yl acetate) | 472 |
| DIMETHYL BENZYL CARBINOL (2-methyl-1-phenylpropan-2-ol) | 264 |
| HEXYL CINNAMIC ALDEHYDE ((E)-2-benzylideneoctanal) | 192 |
| NEROLIDYLE ((Z)-3,7,11-trimethyldodeca-1,6,10-trien-3-yl acetate) | 175 |

It is preferred that an encapsulated perfume composition of the present invention contains at least 3, more particularly at least 5, still more particularly at least 7, and more particularly still, at least 9 GROUP 4 perfume ingredients.

Those encapsulated perfume compositions described hereinabove additionally comprising GROUP 4 ingredients, and in particular at least 3, more particularly at least 5, still more particularly at least 7, and more particularly still, at least 9 GROUP 4 perfume ingredients represent additional aspects of the present invention.

Furthermore, fabric softener or conditioning compositions, particularly those containing structured surfactants; or solid or liquid laundry detergent compositions, and particularly those formats designed as unit dosage forms contained in pouches or pods, and often referred to in the art as "liquid tabs"; or harshly extractive media, including personal care cleansing compositions, such as shampoos, containing encapsulated perfume compositions described herein comprising GROUP 4 ingredients, form further embodiments of the present invention.

In a particular embodiment of the present invention, an encapsulated perfume composition is characterized in that the total Pre-Rub Odour Contribution of the encapsulated perfume ingredients is between $0.5 \times 10^8$ and $1.0 \times 10^9$, more particularly between $1 \times 10^8$ and $8 \times 10^8$ and more particularly still, between $1.5 \times 10^8$ and $6 \times 10^8$; and the distribution of RECON_VOLTAE values of encapsulated perfume ingredients is such that
- 70 wt % or more, more particularly 80 wt % or more, and more particularly still 90 wt % or more of the perfume ingredients have known RECON_VOLTAE values larger than 1200 Bohr$^3$; and
- 0.1 to 30 wt %, more particularly from 1 to 20 wt % and more particularly still, from 1 to 10 wt % of perfume ingredients having RECON_VOLTAE values below 1200 Bohr$^3$.

In another particular aspect of the present invention, an encapsulated perfume composition is characterized in that the total Pre-Rub Odour Contribution of the encapsulated perfume ingredients is between $0.5 \times 10^8$ and $1.0 \times 10^9$, more particularly between $1 \times 10^8$ and $8 \times 10^8$ and more particularly still between $1.5 \times 10^6$ and $6 \times 10^6$; and the distribution of known RECON_VOLTAE values of encapsulated perfume ingredients is such that
- 30 wt % or more, more particularly 35 wt % or more, and more particularly still 40 wt % or more of the perfume ingredients have known RECON_VOLTAE values larger than 1540 Bohr$^3$; and
- 20 to 60 wt %, more particularly 25 to 50 wt %, and more particularly still 30 to 40 wt % of the perfume ingredients have known RECON_VOLTAE values from 1200 Bohr$^3$ to 1540 Bohr$^3$; and
- 0.1 to 30 wt %, more particularly from 1 to 20 wt % and more particularly still from 1 to 10 wt % of perfume ingredients have known RECON_VOLTAE values below 1200 Bohr$^3$.

In another particular embodiment of the present invention, an encapsulated perfume composition contains encapsulated perfume ingredients characterized by a total Pre-Rub Odour Contribution between $0.5 \times 10^8$ and $1.0 \times 10^9$, more particularly $1 \times 10^8$ and $8 \times 10^8$ and more particularly still $1.5 \times 10^8$ and $6 \times 10^8$; and the distribution of known RECON_VOLTAE values of encapsulated perfume ingredients is such that:
- 0.5 to 30, more particularly from 1 to 25 wt % and more particularly still from 5 to 20 wt % of at least one perfume ingredient have known RECON_VOLTAE values above 1750 Bohr$^3$; and
- 20 to 60 wt % or more, more particularly 25 to 55 wt % or more, and more particularly still 30 to 50 wt % or more of the perfume ingredients have known RECON_VOLTAE values from 1540 Bohr$^3$ to 1750 Bohr$^3$; and
- 5 to 50 wt % or more, particularly 10 to 40 wt % or more, and more particularly still 15 to 30 wt % or more of the perfume ingredients have known RECON_VOLTAE values from 1200 Bohr$^3$ to 1540 Bohr$^3$; and
- 0.1 to 30 wt %, more particularly from 1 to 20 wt % and more particularly still from 1 to 10 wt % of perfume ingredients have known RECON_VOLTAE values below 1200 Bohr$^3$.

In another particular embodiment of the present invention, an encapsulated perfume composition contains encapsulated perfume ingredients characterized by a total Pre-Rub Odour Contribution between $0.5 \times 10^8$ and $1.0 \times 10^9$, more particularly between $1 \times 10^8$ and $8 \times 10^8$ and more particularly still between $1.5 \times 10^8$ and $6 \times 10^8$; and the distribution of known RECON_VOLTAE values of encapsulated perfume ingredients is such that:
- 70 wt % or more, more particularly 80 wt % or more, and more particularly still 90 wt % or more of the perfume ingredients have known RECON_VOLTAE values larger than 1750 Bohr$^3$; and
- 0.1 to 30 wt %, more particularly from 1 to 20 wt % and more particularly still from 1 to 10 wt % of the perfume ingredients have known RECON_VOLTAE values below 1750 Bohr$^3$.

Other perfume ingredients that may be employed in the present invention and their respective RECON VOLTAE and $\log_{in}$ Kcaps values are set forth in the following table. One of more of the following perfume ingredients may be contained in encapsulated perfume compositions according to the present invention.

| Ingredient (NAME (IUPAC name)) | RECON_VOLTAE | Log Kcaps |
|---|---|---|
| ACETAL CD ((2-benzyl-1,3-dioxolan-4-yl)methanol) | 1387 | −4.0 |
| ACETAL E ((2-(1-ethoxyethoxy)ethyl)benzene) | 1531 | −1.1 |
| ACETAL R ((2-(1-propoxyethoxy)ethyl)benzene) | 1661 | −1.2 |
| ACETANISOLE (1-(4-methoxyphenyl)ethanone) | 1114 | −2.3 |
| ACETATE PA (allyl 2-phenoxyacetate) | 1407 | −3.5 |
| ACETOIN (3-hydroxybutan-2-one) | 690 | −1.4 |
| ACETOPHENONE (acetophenone) | 923 | −1.5 |
| ACETYL CARYOPHYLLENE ((Z)-4,11,11-trimethyl-8-methylenebicyclo[7.2.0]undec-4-ene) | 2092 | −1.0 |
| ACETYL ISOEUGENOL CRYSTALS ((E)-2-methoxy-4-(prop-1-en-1-yl)phenyl acetate) | 1526 | −2.8 |
| AGARBOIS (N-ethyl-N-(m-tolyl)propionamide) | 1537 | −3.0 |
| ALCOHOL C 10 DECYLIC (decan-1-ol) | 1432 | −2.7 |
| ALCOHOL C 12 LAURIC (dodecan-1-ol) | 1690 | −2.5 |

-continued

| Ingredient (NAME (IUPAC name)) | RECON_VOLTAE | Log Kcaps |
|---|---|---|
| ALCOHOL C 13 OXO (tridecan-1-ol) | 1819 | −2.4 |
| ALCOHOL C 6 HEXYLIC (hexan-1-ol) | 915 | −2.9 |
| ALCOHOL C 8 OCTYLIC (octan-1-ol) | 1173 | −3.0 |
| ALCOHOL C 9 NONYLIC (nonan-1-ol) | 1302 | −3.0 |
| ALDEHYDE C 6 HEXYLIC FOOD GRADE (hexan-1-ol) | 885 | −2.8 |
| ALDEHYDE C 7 HEPTYLIC (heptanal) | 1016 | −2.7 |
| ALDEHYDE C 8 OCTYLIC FOOD GRADE (octanal) | 1145 | −2.7 |
| ALDEHYDE C 9 ISONONYLIC (3,5,5-trimethylhexanal) | 1317 | −2.5 |
| ALDEHYDE C 9 NONYLIC FOOD GRADE (nonanal) | 1274 | −2.8 |
| ALICATE (2,6-dimethylheptan-4-yl acetate) | 1605 | −1.8 |
| ALLYL CAPROATE (allyl hexanoate) | 1307 | −1.8 |
| AMBERKETAL (3,8,8,11a-tetramethyldodecahydro-1H-3,5a-epoxynaphtho[2,1-c]oxepine) | 2339 | −4.0 |
| AMBRETTOLIDE ((Z)-oxacycloheptadec-10-en-2-one) | 2108 | −5.0 |
| AMBRINOL (2,5,5-trimethyl-1,2,3,4,4a,5,6,7-octahydronaphthalen-2-ol) | 1651 | −2.3 |
| AMBROCENIDE ((4aR,5R,7aS,9R)-Octahydro-2,2,5,8,8,9a-hexamethyl-4H-4a,9-methanoazuleno[5,6-d]-1,3-dioxole) | 2339 | −2.1 |
| AMBROFIX (3a,6,6,9a-tetramethyldodecahydronaphtho[2,1-b]furan) | 2039 | −2.0 |
| AMBROXAN (3a,6,6,9a-tetramethyl-2,4,5,5a,7,8,9,9b-octahydro-1H-benzo[e][1]benzofuran) | 2039 | −2.0 |
| AMYL ACETATE (pentyl acetate) | 1075 | −1.2 |
| AMYL BENZOATE (pentyl benzoate) | 1494 | −1.2 |
| AMYL BUTYRATE (pentyl butanoate) | 1333 | −1.6 |
| AMYL CINNAMIC ALDEHYDE ((Z)-2-benzylideneheptanal) | 1649 | −2.8 |
| AMYL PHENYL ACETATE (pentyl 2-phenylacetate) | 1623 | −2.9 |
| AMYL VINYL CARBINOL (oct-1-en-3-ol) | 1149 | −2.9 |
| ANAPEAR ((E)-methyl octa-4,7-dienoate) | 1257 | −2.8 |
| ANATOLYL (phenethyl 2-methylbutanoate) | 1625 | −2.1 |
| ANETHOLE ((E)-1-methoxy-4-(prop-1-en-1-yl)benzene) | 1175 | −1.7 |
| ANISYL ACETATE (4-methoxybenzyl acetate) | 1309 | −3.6 |
| ANISYL ALCOHOL ((4-methoxyphenyl)methanol) | 1021 | −4.0 |
| ANTHER ((2-(isopentyloxy)ethyl)benzene) | 1597 | −1.3 |
| AUBEPINE PARA CRESOL (4-methoxybenzaldehyde) | 981 | −2.1 |
| AZARBRE (3,5-diethyl-2,5-dimethylcyclohex-2-enone) | 1591 | −1.5 |
| BENZALDEHYDE (benzaldehyde) | 790 | −0.9 |
| BENZOPHENONE (benzophenone) | 1347 | −1.5 |
| BENZYL ACETATE (benzyl acetate) | 1118 | −1.6 |
| BENZYL ACETONE (4-phenylbutan-2-one) | 1180 | −1.8 |
| BENZYL ALCOHOL (phenylmethanol) | 831 | −2.6 |
| BENZYL BENZOATE (benzyl benzoate) | 1539 | −3.6 |
| BENZYL BUTYRATE (benzyl butanoate) | 1378 | −1.7 |
| BENZYL CINNAMATE (benzyl 3-phenylprop-2-enoate) | 1748 | −2.5 |
| BENZYL FORMATE (benzyl formate) | 984 | −2.0 |
| BENZYL ISOBUTYRATE (benzyl isobutanoate) | 1374 | −1.4 |
| BENZYL ISOVALERATE (benzyl 3-methylbutanoate) | 1510 | −1.4 |
| BENZYL METHYL ETHER ((methoxymethyl)benzene) | 960 | −2.2 |
| BENZYL PHENYL ACETATE (benzyl 2-phenylacetate) | 1669 | −5.2 |
| BENZYL PROPIONATE (benzyl propionate) | 1249 | −1.6 |
| BENZYL SALICYLATE (benzyl 2-hydroxybenzoate) | 1601 | −5.0 |
| BICYCLO NONALACTONE (octahydro-2H-chromen-2-one) | 1160 | −2.6 |
| BIGARADE OXIDE ((4aS,6R,7S,8aR)-3,3,6,7-tetramethyl-2,4,4a,5,6,7,8,8a-octahydrochromene) | 1610 | −1.2 |
| BISABOLENE ((E)-1-methyl-4-(6-methylhepta-2,5-dien-2-yl)cyclohex-1-ene) | 1804 | −0.8 |
| BORNEOL CRYSTALS ((1S,2S,4S)-1,7,7-trimethylbicyclo[2.2.1]heptan-2-ol) | 1345 | −2.0 |
| BOURGEONAL (3-(4-(tert-butyl)phenyl)propanal) | 1609 | −3.2 |
| BUCCOXIME ((1R,5S,E)-1,5-dimethylbicyclo[3.2.1]octan-8-one oxime) | 1402 | −2.3 |
| BUTYL ISOBUTYRATE, ISO-(2-methylpropyl 2-methylpropanoate) | 1202 | −1.7 |
| BUTYL QUINOLINE SECONDARY (6-(sec-butyl)quinoline) | 1466 | −1.8 |
| CALMODE (1,2,4-trimethoxy-5-propylbenzene) | 1602 | −3.3 |
| CALONE 1951 (7-methyl-2H-benzo[b][1,4]dioxepin-3(4H)-one) | 1228 | −0.9 |
| CALYPSONE (6-methoxy-2,6-dimethyloctanal) | 1596 | −2.5 |
| CAMPHENE ((1S,4R)-2,2-dimethyl-3-methylenebicyclo[2.2.1]heptane) | 1202 | −0.3 |
| CAMPHOR ((1S,4S)-1,7,7-trimethylbicyclo[2.2.1]heptan-2-one) | 1301 | −1.9 |
| CANTHOXAL (3-(4-methoxyphenyl)-2-methylpropanal) | 1372 | −3.3 |
| CARAMEL LACTONE (3-hydroxy-4,5-dimethylfuran-2(5H)-one) | 885 | −3.5 |
| CARVACROL (5-isopropyl-2-methylphenol) | 1217 | −2.0 |
| CARVONE LAEVO (2-methyl-5-(prop-1-en-2-yl)cyclohex-2-enone) | 1249 | −1.2 |
| CASSIONE (4-(1-3-benzodioxol-5-yl)-2-butanone) | 1360 | −2.8 |
| CELERY KETONE (3-methyl-5-propylcyclohex-2-enone) | 1262 | −1.4 |

-continued

| Ingredient (NAME (IUPAC name)) | RECON_VOLTAE | Log Kcaps |
|---|---|---|
| CENTIFOLYL (2-phenylethyl 2,2-dimethylpropanoate) | 1665 | −2.0 |
| CEPIONATE (methyl 2-(3-oxo-2-pentylcyclopentyl)acetate) | 1784 | −2.4 |
| CETALOX (3a,6,6,9a-tetramethyl-2,4,5,5a,7,8,9,9b-octahydro-1H-benzo[e][1]benzofuran) | 2039 | −2.1 |
| CETONAL (2-methyl-4-(2,6,6-trimethylcyclohex-2-en-1-yl)butanal) | 1825 | −2.6 |
| CETONE ALPHA ((E)-3-methyl-4-(2,6,6-trimethylcyclohex-2-en-1-yl)but-3-en-2-one) | 1782 | −1.6 |
| CETONE V ((E)-1-(2,6,6-trimethylcyclohex-2-en-1-yl)hepta-1,6-dien-3-one) | 2028 | −3.3 |
| CINNAMALVA ((E)-3-phenylprop-2-en-1-yl acetate) | 1075 | −2.0 |
| CINNAMIC ALCOHOL ((E)-3-phenylprop-2-en-1-ol) | 1048 | −2.4 |
| CINNAMIC ALDEHYDE ((2E)-3-phenylprop-2-enal) | 1001 | −2.0 |
| CINNAMYL ACETATE ((E)-3-phenylprop-2-en-1-yl acetate) | 1334 | −1.7 |
| CINNAMYL CINNAMATE (3-phenylprop-2-enyl 3-phenylprop-2-enoate) | 1967 | −3.2 |
| CITRAL DIMETHYL ACETAL ((E)-1,1-dimethoxy-3,7-dimethylocta-2,6-diene) | 1680 | −1.9 |
| CITRONELLYL ISOBUTYRATE (3,7-dimethyloct-6-en-1-yl isobutanoate) | 1936 | −1.3 |
| CITRONELLYL OXYACETALDEHYDE (2-((3,7-dimethyloct-6-en-1-yl)oxy)acetaldehyde) | 1679 | −3.4 |
| CIVETTONE ((Z)-cycloheptadec-9-enone) | 2180 | −2.5 |
| CLARITONE (2,4,4,7-tetramethyloct-6-en-3-one) | 1658 | −0.9 |
| CONIFERAN (2-(tert-pentyl)cyclohexyl acetate) | 1807 | −1.9 |
| CORPS CASSIS (2-(2-mercaptopropan-2-yl)-5-methylcyclohexanone) | 1483 | −2.2 |
| CORPS PAMPLEMOUSSE PURE ((4S)-4,7,7-trimethyl-6-thiabicyclo[3.2.1]octane) | 1374 | 0.1 |
| CORYLONE DRIED (2-hydroxy-3-methylcyclopent-2-enone) | 822 | −2.8 |
| COUMARIN (2H-chromen-2-one) | 985 | −1.9 |
| CREOSOL (2-methoxy-4-methylphenol) | 1021 | −2.6 |
| CRESOL PARA (p-cresol) | 830 | −1.8 |
| CRESYL ACETATE PARA (p-tolyl acetate) | 1115 | −2.2 |
| CRESYL CAPRYLATE PARA (p-tolyl octanoate) | 1892 | −2.6 |
| CRESYL ISOBUTYRATE PARA (p-tolyl isobutanoate) | 1374 | −1.9 |
| CRESYL METHYL ETHER PARA (1-methoxy-4-methylbenzene) | 959 | −1.8 |
| CRESYL PHENYL ACETATE PARA (p-tolyl 2-phenylacetate) | 1666 | −4.9 |
| CUMIN NITRILE (4-isopropylbenzonitrile) | 1246 | −1.2 |
| CUMINIC ALDEHYDE (4-isopropylbenzaldehyde) | 1177 | −1.0 |
| CUMINYL ALCOHOL ((4-isopropylphenyl)methanol) | 1217 | −2.8 |
| CYCLAL C (2,4-dimethylcyclohex-3-enecarbaldehyde) | 1138 | −1.9 |
| CYCLEMONE A (8,8-dimethyl-1,2,3,4,5,6,7,8-octahydronaphthalene-2-carbaldehyde) | 1610 | −2.4 |
| CYCLOHEXAL (4-(4-hydroxy-4-methylpentyl)cyclohex-3-enecarbaldehyde) | 1719 | −3.7 |
| CYCLOHEXYL ETHYL ACETATE (2-cyclohexylethyl acetate) | 1371 | −1.9 |
| CYCLOMETHYLENE CITRONELLOL (3-(4-methylcyclohex-3-en-1-yl)butan-1-ol) | 1425 | −1.9 |
| CYDRANE (hexyl 2-methylbutanoate) | 1588 | −0.5 |
| CYMENE PARA (1-methyl-4-propan-2-ylbenzene) | 1155 | −0.6 |
| CYPRISATE (methyl 1,4-dimethylcyclohexanecarboxylate) | 2826 | −2.0 |
| DAMASCONE BETA ((E)-1-(2,6,6-trimethylcyclohex-1-en-1-yl)but-2-en-1-one) | 1655 | −1.3 |
| DECADIENAL ((2E,4E)-deca-2,4-dienal) | 1309 | −2.2 |
| DECALACTONE DELTA (6-pentyltetrahydro-2H-pyran-2-one) | 1378 | −3.2 |
| DECALACTONE GAMMA (5-hexyloxolan-2-one) | 1386 | −3.7 |
| DECANONITRILE (decanenitrile) | 1464 | −1.5 |
| DECATONE (6-isopropyloctahydronaphthalen-2(1H)-one) | 1610 | −2.2 |
| DECEN-1-AL, CIS-4-((Z)-dec-4-enal) | 1363 | −2.8 |
| DECENAL-2-TRANS ((E)-dec-2-enal) | 1356 | −2.1 |
| DECENAL-9 (9-decenal) | 1369 | −3.3 |
| DELTA-3 CARENE ((1S,6S)-3,7,7-trimethylbicyclo[4.1.0]hept-3-ene) | 1200 | −1.0 |
| DIETHYL MALONATE (diethyl propanedioate) | 1152 | −1.4 |
| DIHEXYL FUMARATE (dihexyl but-2-enedioate) | 2263 | −1.7 |
| DIHYDRO AMBRATE (2-(sec-butyl)-1-vinylcyclohexyl acetate) | 1865 | −2.4 |
| DIHYDRO EUGENOL (2-methoxy-4-propylphenol) | 1281 | −2.5 |
| DIHYDRO FARNESAL ((Z)-3,7,11-trimethyldodeca-6,10-dienal) | 1967 | −4.0 |
| DIHYDRO IONONE BETA (4-(2,6,6-trimethylcyclohex-1-en-1-yl)butan-2-one) | 1695 | −1.5 |
| DIHYDRO LINALOOL (3,7-dimethyloct-6-en-3-ol) | 1403 | −2.0 |
| DIHYDRO MYRCENOL (2,6-dimethyloct-7-en-2-ol) | 1410 | −2.8 |
| DIHYDRO MYRCENYL ACETATE (2,6-dimethyloct-7-en-2-yl acetate) | 1695 | −2.3 |

-continued

| Ingredient (NAME (IUPAC name)) | RECON_VOLTAE | Log Kcaps |
|---|---|---|
| DIHYDRO TERPINEOL (2-(4-methylcyclohexyl)propan-2-ol) | 1356 | −2.0 |
| DIHYDRO TERPINYL ACETATE (2-(4-methylcyclohexyl)propan-2-yl acetate) | 1639 | −1.5 |
| DIMETHYL ANTHRANILATE (methyl 2-(methylamino)benzoate) | 1206 | −3.0 |
| DIMETHYL HYDROQUINONE CRYSTALS (1,4-dimethoxybenzene) | 1022 | −2.9 |
| DIMETHYL PHENYL ETHYL CARBINOL (2-methyl-4-phenylbutan-2-ol) | 1352 | −2.2 |
| DIMYRCETOL (2,6-dimethyloct-7-en-2-ol) | 2969 | −1.9 |
| DIPHENYL METHANE (diphenylmethane) | 1320 | −1.4 |
| DIPHENYL OXIDE (oxydibenzene) | 1260 | −1.2 |
| DISPIRONE (7,9-dimethylspiro[5.5]undecan-3-one) | 1648 | −2.4 |
| DODECALACTONE DELTA (6-heptyltetrahydro-2H-pyran-2-one) | 1636 | −3.4 |
| DODECALACTONE GAMMA (5-octyloxolan-2-one) | 1644 | −3.9 |
| ESTRAGOLE (1-allyl-4-methoxybenzene) | 1180 | −1.7 |
| ETHYL 2,4-DECADIENOATE ((2E,4Z)-ethyl deca-2,4-dienoate) | 1625 | −1.5 |
| ETHYL ACETATE (ethyl acetate) | 685 | −0.7 |
| ETHYL ACETO ACETATE (ethyl 3-oxobutanoate) | 964 | −1.0 |
| ETHYL AMYL KETONE (octan-3-one) | 1146 | −1.3 |
| ETHYL BENZOATE (ethyl benzoate) | 1106 | −1.7 |
| ETHYL BUTYRATE (ethyl butanoate) | 945 | −1.2 |
| ETHYL CINNAMATE (ethyl 3-phenylprop-2-enoate) | 1317 | −1.0 |
| ETHYL ISOAMYL KETONE (6-methylheptan-3-one) | 1149 | −1.2 |
| ETHYL ISOBUTYRATE (ethyl 2-methylpropionate) | 940 | −0.8 |
| ETHYL ISOVALERATE (ethyl 3-methylbutanoate) | 1077 | −1.3 |
| ETHYL LAITONE (8-ethyl-1-oxaspiro[4.5]decan-2-one) | 1429 | −2.2 |
| ETHYL MALTOL (2-ethyl-3-hydroxy-4H-pyran-4-one) | 985 | −3.7 |
| ETHYL METHYL-2-BUTYRATE (ethyl 2-methylbutanoate) | 1069 | −0.6 |
| ETHYL PELARGONATE (ethyl nonanoate) | 1591 | −2.4 |
| ETHYL PHENYL ACETATE (ethyl 2-phenylacetate) | 1236 | −2.6 |
| ETHYL PHENYL GLYCIDATE (ethyl 3-phenyloxirane-2-carboxylate) | 1347 | −1.9 |
| ETHYL PROPIONATE (ethyl propionate) | 816 | −2.0 |
| ETHYL SALICYLATE (ethyl 2-hydroxybenzoate) | 1168 | −1.2 |
| ETHYL VANILLIN (3-ethoxy-4-hydroxybenzaldehyde) | 1168 | −2.2 |
| ETHYL-2 DIMETHYL-3,5 PYRAZINE (2-ethyl-3,5-dimethylpyrazine) | 1100 | −2.4 |
| ETHYLENE BRASSYLATE (1,4-dioxacycloheptadecane-5,17-dione) | 2096 | −3.0 |
| EUGENOL PURE (4-allyl-2-methoxyphenol) | 1242 | −2.8 |
| EUGENYL ACETATE (4-allyl-2-methoxyphenyl acetate) | 1527 | −3.5 |
| EVERNYL (methyl 2,4-dihydroxy-3,6-dimethylbenzoate) | 1362 | −3.6 |
| FARNESENE ((E)-7,11-dimethyl-3-methylenedodeca-1,6,10-triene) | 1863 | −2.2 |
| FARNESOL ((2E,6Z)-3,7,11-trimethyldodeca-2,6,10-trien-1-ol) | 1962 | −4.5 |
| FENCHONE ALPHA (1,3,3-trimethylbicyclo[2.2.1]heptan-2-one) | 1301 | −1.6 |
| FENNALDEHYDE (3-(4-methoxyphenyl)-2-methylpropanal) | 1372 | −3.3 |
| FLEURANIL (3-(4-ethylphenyl)-2,2-dimethylpropanenitrile) | 1674 | −1.7 |
| FLORALYM (2,6-dimethyloct-7-en-2-ol) | 1410 | −2.8 |
| FLORAMAT (2-(tert-butyl)cyclohexyl ethyl carbonate) | 1863 | −0.5 |
| FLORIDILE ((E)-undec-9-enenitrile) | 1560 | −2.8 |
| FLOROL (2-isobutyl-4-methyltetrahydro-2H-pyran-4-ol) | 1432 | −2.5 |
| FLOROSA (tetrahydro-4-methyl-2-(2-methylpropyl)-2H-pyran-4-ol) | 1432 | −2.5 |
| FLORYMOSS ((Z)-1-(cyclooct-3-en-1-yl)propan-1-ol) | 1451 | −2.9 |
| FOLENOX (4,4,8,8-tetramethyloctahydro-4a,7-methanonaphtho[1,8a-b]oxirene) | 1865 | −1.5 |
| FOLIONE (methyl oct-2-ynoate) | 1246 | −1.7 |
| FOLROSIA (4-isopropylcyclohexanol) | 1229 | −2.3 |
| FRAISTONE (ethyl 2-(2,4-dimethyl-1,3-dioxolan-2-yl)acetate) | 1440 | −3.1 |
| FRESCILE (3-methyldodecanenitrile) | 1859 | −1.9 |
| FRUCTONE (ethyl 2-(2-methyl-1,3-dioxolan-2-yl)acetate) | 1307 | −3.3 |
| GALAXOLIDE (4,6,6,7,8,8-hexamethyl-1,3,4,6,7,8-hexahydrocyclopenta[g]isochromene) | 2160 | −4.3 |
| GARDAMIDE (N,2-dimethyl-N-phenylbutanamide) | 1534 | −2.5 |
| GARDENOL (1-phenylethyl acetate) | 1246 | −1.7 |
| GEORGYWOOD (1-(1,2,8,8-tetramethyl-1,2,3,4,5,6,7,8-octahydronaphthalen-2-yl)ethanone) | 2037 | −1.3 |
| GERANODYLE (2-(2-hydroxypropan-2-yl)-5-methylcyclohexanol) | 1420 | −4.0 |
| GERANYL ACETONE ((E)-6,10-dimethylundeca-5,9-dien-2-one) | 1705 | −1.1 |
| GERANYL CROTONATE ((E)-3,7-dimethylocta-2,6-dien-1-yl but-2-enoate) | 1862 | −2.3 |
| GERANYL FORMATE ((E)-3,7-dimethylocta-2,6-dien-1-yl formate) | 1510 | −1.6 |

-continued

| Ingredient (NAME (IUPAC name)) | RECON_VOLTAE | Log Kcaps |
|---|---|---|
| GERANYL PHENYL ACETATE ((E)-3,7-dimethylocta-2,6-dien-1-yl 2-phenylacetate) | 2194 | −3.8 |
| GERANYL PROPIONATE ((E)-3,7-dimethylocta-2,6-dien-1-yl propionate) | 1773 | −1.6 |
| GLYCOLIERRAL (2-(8-isopropyl-6-methylbicyclo[2.2.2]oct-5-en-2-yl)-1,3-dioxolane) | 1854 | −1.6 |
| GRISALVA (3a-ethyl-6,6,9a-trimethyldodecahydronaphtho[1,2-c]furan) | 2203 | −2.6 |
| GRISAMBROL B (ethyl picolinate) | 1076 | −2.4 |
| GUAIACOL (2-methoxyphenol) | 893 | −2.9 |
| GUAIYL ACETATE (2-(3,8-dimethyl-1,2,3,4,5,6,7,8-octahydroazulen-5-yl)propan-2-yl acetate) | 2161 | −1.9 |
| GYRANE (2-butyl-4,6-dimethyl-3,6-dihydro-2H-pyran) | 1446 | −2.1 |
| HELIOTROPINE (benzo[d][1,3]dioxole-5-carbaldehyde) | 971 | −1.4 |
| HELVETOLIDE (2-(1-(3,3-dimethylcyclohexyl)ethoxy)-2-methylpropyl propionate) | 2388 | −3.1 |
| HEPTALACTONE GAMMA (5-propyloxolan-2-one) | 996 | −2.2 |
| HERBAVERT (3-ethoxy-1,1,5-trimethylcyclohexane) | 1520 | −1.4 |
| HERBOXANE (2-butyl-4,4,6-trimethyl-1,3-dioxane) | 1562 | −3.7 |
| HERCOLYN D (methyl 7-isopropyl-1,4a-dimethyl-1,2,3,4,4a,4b,5,6,7,8,10,10a-dodecahydrophenanthrene-1-carboxylate) | 2656 | −5.0 |
| HEXENAL-2-TRANS (E-hex-2-enal) | 841 | −1.7 |
| HEXENOL-2-TRANS ((E)-hex-2-en-1-ol) | 886 | −2.5 |
| HEXENOL-3-CIS ((Z)-hex-3-en-1-ol) | 876 | −2.5 |
| HEXENYL ACETATE CIS (cis-hex-3-enyl acetate) | 1165 | −1.4 |
| HEXENYL HEXENOATE CIS-3 ((Z)-(Z)-hex-3-en-1-yl hex-3-enoate) | 1644 | −3.4 |
| HEXENYL-3-CIS ACETATE ((Z)-hex-3-en-1-yl acetate) | 1162 | −1.4 |
| HEXENYL-3-CIS BENZOATE ((Z)-hex-3-en-1-yl benzoate) | 1584 | −2.4 |
| HEXENYL-3-CIS FORMATE ((Z)-hex-3-en-1-yl formate) | 1029 | −1.9 |
| HEXENYL-3-CIS ISOBUTYRATE ((Z)-hex-3-en-1-yl isobutanoate) | 1420 | −0.7 |
| HEXENYL-3-CIS METHYL-2-BUTYRATE ((Z)-hept-3-en-1-yl 2-methyl butanoate) | 1549 | −1.5 |
| HEXENYL-3-CIS PROPIONATE ((Z)-hex-3-en-1-yl propionate) | 1292 | −1.2 |
| HEXENYL-3-CIS SALICYLATE ((Z)-hex-3-en-1-yl 2-hydroxybenzoate) | 1646 | −3.5 |
| HEXENYL-3-CIS TIGLATE ((E)-(Z)-hex-3-en-1-yl 2-methylbut-2-enoate) | 1505 | −1.8 |
| HEXENYL-3-TRANS ACETATE ((E)-hex-3-enyl] acetate) | 1162 | −1.5 |
| HEXYL ACETATE (hexyl acetate) | 1202 | −1.2 |
| HEXYL BENZOATE (hexyl benzoate) | 1623 | −1.4 |
| HEXYL BUTYRATE (hexyl butanoate) | 1462 | −1.8 |
| HEXYL PROPIONATE (hexyl propionate) | 1333 | −1.5 |
| HOMOFURONOL (2-ethyl-4-hydroxy-5-methylfuran-3(2H)-one) | 1025 | −3.6 |
| HYDRATROPIC ALDEHYDE (2-phenylpropanal) | 1048 | −2.4 |
| HYDROXYCITRONELLAL DIMETHYL ACETAL (8,8-dimethoxy-2,6-dimethyloctan-2-ol) | 1831 | −3.0 |
| HYDROXYCITRONELLAL (7-hydroxy-3,7-dimethyloctanal) | 1472 | −4.2 |
| IRISANTHEME ((E)-3-methyl-4-(2,6,6-trimethylcyclohex-2-en-1-yl)but-3-en-2-one) | 1806 | −1.7 |
| IRIVAL ((E)-non-2-enenitrile) | 1301 | −1.4 |
| ISO CYCLO GERANIOL ((2,4,6-trimethylcyclohex-3-en-1-yl)methanol) | 1295 | −1.6 |
| ISOAMYL ACETATE (isopentyl acetate) | 1075 | −1.2 |
| ISOAMYL BUTYRATE (isopentyl butanoate) | 1335 | −0.5 |
| ISOAMYL PROPIONATE (isopentyl propionate) | 1206 | −1.1 |
| ISOBUTYL BENZOATE (2-methylpropyl benzoate) | 1368 | −1.4 |
| ISOBUTYL ISOBUTYRATE (2-methylpropyl 2-methylpropanoate) | 1202 | −1.7 |
| ISOBUTYL METHOXY PYRAZINE (2-methylpropyl 3-methoxypyrazine) | 1311 | −2.2 |
| ISOBUTYL PHENYLACETATE (2-methylpropyl 2-phenylacetate) | 1497 | −2.0 |
| ISOBUTYL QUINOLINE-2 (6-butan-2-yl-quinoline) | 1473 | −1.6 |
| ISOBUTYL SALICYLATE (isobutyl 2-hydroxybenzoate) | 1430 | −1.6 |
| ISOEUGENOL ((E)-2-methoxy-4-(prop-1-en-1-yl)phenol) | 1238 | −2.5 |
| ISOJASMONE T (2-hexylcyclopent-2-enone) | 1411 | −2.0 |
| ISOLONGIFOLANONE (2,2,7,7-tetramethyltricyclo[6.2.1.01,6]undecan-5-one) | 1900 | −1.5 |
| ISOMENTHONE DL (2-isopropyl-5-methylcyclohexanone) | 1315 | −1.5 |
| ISONONANOL (3,5,5-trimethylhexan-1-ol) | 1345 | −2.4 |
| ISOPENTYRATE (4-methylpent-4-en-2-yl isobutanoate) | 1434 | −1.2 |
| ISOPROPYL QUINOLINE (6-isopropylquinoline) | 1336 | −1.7 |
| ISOPULEGOL (5-methyl-2-(prop-1-en-2-yl)cyclohexanol) | 1315 | −2.3 |
| ISORALDEINE CETONE ALPHA ((E)-3-methyl-4-(2,6,6-trimethylcyclohex-2-en-1-yl)but-3-en-2-one) | 1806 | −1.6 |

| Ingredient (NAME (IUPAC name)) | RECON_VOLTAE | Log Kcaps |
|---|---|---|
| JASMAL (3-pentyltetrahydro-2H-pyran-4-yl acetate) | 1709 | −4.3 |
| JASMATONE (2-hexylcyclopentanone) | 1439 | −2.2 |
| JASMIN LACTONE DELTA ((Z)-6-(pent-2-en-1-yl)tetrahydro-2H-pyran-2-one) | 1343 | −2.4 |
| JASMIN LACTONE GAMMA ((Z)-5-(hex-3-en-1-yl)-5-methyloxolan-2-one) | 1472 | −2.4 |
| JASMOLACTONE ((E)-6-(pent-3-en-1-yl)tetrahydro-2H-pyran-2-one) | 1341 | −2.5 |
| JASMONYL (3-butyl-5-methyltetrahydro-2H-pyran-4-yl acetate) | 1708 | −3.1 |
| JASMOPYRANE (3-pentyltetrahydro-2H-pyran-4-yl acetate) | 1709 | −3.0 |
| JAVANOL ((1-methyl-2-((1,2,2-trimethylbicyclo[3.1.0]hexan-3-yl)methyl)cyclopropyl)methanol) | 1930 | −3.0 |
| KEFARENE (1-(4-methoxy-2,2,6,6-tetramethylcyclohex-3-en-1-yl)ethanone) | 1807 | −2.0 |
| KEPHALIS (4-(1-ethoxyvinyl)-3,3,5,5-tetramethylcyclohexanone) | 1936 | −2.4 |
| KOHINOOL (3,4,5,6,6-pentamethylheptan-2-ol) | 1751 | −2.1 |
| LABIENONE ((E)-2,4,4,7-tetramethylnona-6,8-dien-3-one) | 1748 | −1.4 |
| LABIENOXIME ((3E,6E)-2,4,4,7-tetramethylnona-6,8-dien-3-one oxime) | 1850 | −4.0 |
| LACTOSCATONE (2,8,8-trimethyloctahydro-1H-4a,2-(epoxymethano)naphthalen-10-one) | 1804 | −2.6 |
| LAITONE (8-isopropyl-1-oxaspiro[4.5]decan-2-one) | 1561 | −2.2 |
| LIMETOL (2,2,6-trimethyl-6-vinyltetrahydro-2H-pyran) | 1332 | −1.3 |
| LINALOOL OXIDE (2-(5-methyl-5-vinyltetrahydrofuran-2-yl)propan-2-ol) | 1395 | −2.5 |
| LINALYL CINNAMATE (3,7-dimethylocta-1,6-dien-3-yl 3-phenylprop-2-enoate) | 2286 | −2.2 |
| LINALYL FORMATE (3,7-dimethylocta-1,6-dien-3-yl formate) | 1520 | −2.0 |
| LINALYL ISOBUTYRATE (3,7-dimethylocta-1,6-dien-3-yl isobutanoate) | 1911 | −1.4 |
| LINALYL PROPIONATE (3,7-dimethylocta-1,6-dien-3-yl propionate) | 1783 | −1.9 |
| LINDENOL (2-(4-methylcyclohex-3-en-1-yl)propan-2-ol) | 1307 | −1.7 |
| LONGIFOLENE STD ((3R,3aR,8R,8aS)-4,4,8-trimethyl-9-methylenedecahydro-3,8-methanoazulene) | 1799 | −1.0 |
| MACEAL (bicyclo[2.2.2]oct-5-ene-2-carboxaldehyde) | 1573 | −3.0 |
| MAGNOLAN (2,4-dimethyl-4,4a,5,9b-tetrahydroindeno[1,2-d][1,3]dioxine) | 1509 | −3.0 |
| MAHONIAL ((4E)-9-hydroxy-5,9-dimethyl-4-decenal) | 1685 | −3.5 |
| MAJANTOL (2,2-dimethyl-3-(m-tolyl)propan-1-ol) | 1507 | −2.4 |
| MALTOL (3-hydroxy-2-methyl-4H-pyran-4-one) | 854 | −3.9 |
| MARENIL (2-(4-(tert-butyl)phenyl)acetonitrile) | 1542 | −2.1 |
| MAYOL ((4-isopropylcyclohexyl)methanol) | 1345 | −2.7 |
| MEFRANAL (3-methyl-5-phenylpentanal) | 1443 | −2.7 |
| MEFROSOL (3-methyl-5-phenylpentan-1-ol) | 1471 | −3.5 |
| MELOZONE (tricyclo[5.2.1.02,6]decane-3-carbaldehyde) | 1260 | −1.9 |
| MENTHANYL ACETATE (2-(4-methylcyclohexyl)propan-2-yl acetate) | 1639 | −1.5 |
| METAMBRATE (2-(sec-butyl)-1-methylcyclohexyl acetate) | 1772 | −1.7 |
| METHOXY MELONAL (6-methoxy-2,6-dimethylheptanal) | 1468 | −2.5 |
| METHOXY PHENYL BUTANONE (4-(4-methoxyphenyl)butan-2-one) | 1372 | −2.6 |
| METHYL ACETOPHENONE (1-(p-tolyl)ethanone) | 1051 | −1.4 |
| METHYL AMYL KETONE (heptan-2-one) | 1015 | −1.0 |
| METHYL ANTHRANILATE (methyl 2-aminobenzoate) | 1077 | −4.0 |
| METHYL BENZOATE (methyl benzoate) | 981 | −2.3 |
| METHYL CAMOMILLE (butyl 2-methylpentanoate) | 1460 | −0.2 |
| METHYL CINNAMATE (methyl 3-phenylprop-2-enoate) | 1192 | −1.6 |
| METHYL CINNAMIC ALDEHYDE ((Z)-2-methyl-3-phenylacrylaldehyde) | 1132 | −1.9 |
| METHYL CRESOTATE PARA (methyl 2-hydroxy-5-methylbenzoate) | 1172 | −2.3 |
| METHYL DECALACTONE GAMMA (5-hexyl-5-methyloxolan-2-one) | 1517 | −2.5 |
| METHYL DIANTILIS (2-ethoxy-4-(methoxymethyl)phenol) | 1338 | −3.3 |
| METHYL DIHYDRO ISOJASMONATE (methyl 3-oxo-2-pentylcyclopentaneacetate) | 1784 | −1.8 |
| METHYL DIPHENYL ETHER (2-methoxy-1,1'-biphenyl) | 1386 | −1.9 |
| METHYL EPI JASMONATE ((Z)-methyl 2-(3-oxo-2-(pent-2-en-1-yl)cyclopentyl)acetate) | 1742 | −2.1 |
| METHYL GEOSMIN (4,4,8a-trimethyldecahydronaphthalen-4a-ol) | 1738 | −2.8 |
| METHYL HEPTENONE PURE (6-methylhept-5-en-2-one) | 1101 | −0.6 |

| Ingredient (NAME (IUPAC name)) | RECON_VOLTAE | Log Kcaps |
|---|---|---|
| METHYL HEXYL KETONE (octan-2-one) | 1144 | −1.2 |
| METHYL ISO EUGENOL ((E)-1,2-dimethoxy-4-(prop-1-en-1-yl)benzene) | 1366 | −3.0 |
| METHYL LAITONE (8-methyl-1-oxaspiro[4.5]decan-2-one) | 1299 | −2.0 |
| METHYL LINOLEATE ((9E,12E)-methyl octadeca-9,12-dienoate) | 2546 | −2.9 |
| METHYL METHYL BUTYRATE (methyl 2-methylbutanoate) | 944 | −2.2 |
| METHYL PARA-CRESOL (1-methoxy-4-methylbenzene) | 959 | −2.0 |
| METHYL PHENYL ACETATE (methyl 2-phenylacetate) | 1111 | −2.4 |
| METHYL QUINOLINE PARA (6-methylquinoline) | 1078 | −1.8 |
| METHYL SALICYLATE (methyl 2-hydroxybenzoate) | 1043 | −2.0 |
| METHYL TUBERATE PURE (4-methyl-5-pentyldihydrofuran-2(3H)-one) | 1385 | −2.6 |
| METHYL-2 BUTANOL-1 FR (2-methylbutan-1-ol) | 789 | −1.9 |
| METHYL-2-PENTENOIC ACID, 2-((E)-2-methylpent-2-enoic acid) | 903 | −1.6 |
| METHYL-3 METHOXY-3 BUTANOL (3-methoxy-3-methylbutan-1-ol) | 981 | −3.0 |
| METHYLOCTYLACETALDEHYDE MOA (2-methyl-decanal) | 1530 | −2.6 |
| MOXALONE (1a,3,3,4,6,6-hexamethyl-1a,2,3,4,5,6,7,7a-octahydronaphtho[2,3-b]oxirene) | 1992 | −2.8 |
| MUSCENONE ((Z)-3-methylcyclopentadec-5-enone) | 2053 | −2.5 |
| MUSCONE (3-methylcyclopentadecanone) | 2095 | −2.5 |
| MUSK C14 (1,4-dioxacyclohexadecane-5,16-dione) | 1967 | −3.0 |
| MUSK R1 (1,7-dioxacycloheptadecan-8-one) | 2065 | −2.9 |
| MYRALDYL ACETATE ((4-(4-methylpent-3-en-1-yl)cyclohex-3-en-1-yl)methyl acetate) | 1928 | −1.6 |
| MYRCENE 90 (7-methyl-3-methyleneocta-1,6-diene) | 1259 | −0.4 |
| MYROXIDE (2,2-dimethyl-3-(3-methylpenta-2,4-dienyl)oxirane) | 1282 | −0.9 |
| MYSTIKAL (2-methylundecanoic acid) | 1722 | −5.0 |
| NEOCASPIRENE (10-isopropyl-2,7-dimethyl-1-oxaspiro[4.5]deca-3,6-diene) | 1715 | −1.4 |
| NEROL C (3,7-dimethyl-2,6-octadien-1-ol) | 1363 | −2.1 |
| NEROLEX ((Z)-3,7-dimethylocta-2,6-dien-1-ol) | 1357 | −2.2 |
| NEROLIDOL ((E)-3,7,11-trimethyldodeca-1,6,10-trien-3-ol) | 1971 | −4.5 |
| NEROLINE (2-ethoxynaphthalene) | 1294 | −1.1 |
| NEROLIONE (1-(3-methylbenzofuran-2-yl)ethanone) | 1251 | −1.7 |
| NIRVANOLIDE ((E)-13-methyloxacyclopentadec-10-en-2-one) | 1981 | −1.8 |
| NONADIENAL ((2E,6Z)-nona-2,6-dienal) | 1187 | −1.9 |
| NONADIENOL-2,6 ((2E,6Z)-nona-2,6-dien-1-ol) | 1234 | −2.5 |
| NONADIENYL ACETATE ((2E,6Z)-nona-2,6-dien-1-yl acetate) | 1520 | −2.4 |
| NONANYL ACETATE (nonanyl acetate) | 1632 | −1.7 |
| NONENOL-6-CIS ((Z)-non-6-en-1-ol) | 1263 | −2.8 |
| NOOTKATONE CRYSTALS (4,4a-dimethyl-6-(prop-1-en-2-yl)-4,4a,5,6,7,8-hexahydronaphthalen-2(3H)-one) | 1848 | −2.5 |
| NOPYL ACETATE (2-(6,6-dimethylbicyclo[3.1.1]hept-2-en-2-yl)ethyl acetate) | 1669 | −2.1 |
| OCIMENE ((E)-3,7-dimethylocta-1,3,6-triene) | 1253 | −0.7 |
| OCTALACTONE DELTA (6-propyltetrahydro-2H-pyran-2-one) | 1119 | −2.8 |
| OCTALACTONE GAMMA (5-butyloxolan-2-one) | 1128 | −3.4 |
| OCTENOL (oct-1-en-3-ol) | 1149 | −2.9 |
| OCTENYL ACETATE (oct-1-en-3-yl acetate) | 1436 | −1.8 |
| OKOUMAL (2,4-dimethyl-2-(5,5,8,8-tetramethyl-5,6,7,8-tetrahydronaphthalen-2-yl)-1,3-dioxolane) | 2422 | −2.6 |
| ONCIDAL ((E)-2,6,10-trimethylundeca-5,9-dienal) | 1833 | −2.8 |
| OPALAL (7-isopropyl-8,8-dimethyl-6,10-dioxaspiro[4.5]decane) | 1831 | −3.0 |
| ORANGER CRYSTALS (1-(2-naphtalenyl)-ethanone) | 1262 | −2.0 |
| ORCINYL 3 (3-methoxy-5-methylphenol) | 1021 | −3.0 |
| OSYROL (7-methoxy-3,7-dimethyloctan-2-ol) | 1643 | −3.2 |
| OXANE (2-methyl-4-propyl-1,3-oxathiane) | 1264 | −1.8 |
| OXYOCTALINE FORMATE (2,4a,5,8a-tetramethyl-1,2,3,4,4a,7,8,8a-octahydronaphthalen-1-yl formate) | 1974 | −2.1 |
| PANDANOL ((2-methoxyethyl)benzene) | 1081 | −1.9 |
| PARMAVERT (1,1-dimethoxynon-2-yne) | 1547 | −1.9 |
| PEACH PURE (5-heptyldihydrofuran-2(3H)-one) | 1515 | −3.9 |
| PELARGOL (3,7-dimethyloctan-1-ol) | 1438 | −2.3 |
| PEOMOSA (2-(o-tolyl)ethanol) | 1078 | −2.4 |
| PEPPERWOOD (3,7-dimethylocta-1,6-dien-3-yl dimethylcarbamate) | 1941 | −2.6 |
| PERANAT (2-methylpentyl 2-methylpentanoate) | 1719 | −0.9 |
| PETIOLE ((2-isopropoxyethyl)benzene) | 1347 | −1.5 |
| PHARAONE (2-cyclohexylhepta-1,6-dien-3-one) | 1629 | −2.3 |
| PHENOXANOL (3-methyl-5-phenylpentan-1-ol) | 1471 | −2.5 |
| PHENOXY ACETALDEHYDE (2-phenoxyacetaldehyde) | 987 | −2.9 |

| Ingredient (NAME (IUPAC name)) | RECON_VOLTAE | Log Kcaps |
|---|---|---|
| PHENOXY ETHYL ALCOHOL (2-phenoxyethanol) | 1007 | −2.9 |
| PHENOXY ETHYL ISOBUTYRATE (2-(phenoxy)ethyl 2-methylpropionate) | 1553 | −4.3 |
| PHENYL ACETALDEHYDE (2-phenyl-ethanal) | 919 | −2.5 |
| PHENYL ACETIC ACID PURE (2-phenylacetic acid) | 981 | −2.5 |
| PHENYL ETHYL ACETATE (2-phenethyl acetate) | 1237 | −1.8 |
| PHENYL ETHYL ALCOHOL (2-phenylethanol) | 951 | −2.4 |
| PHENYL ETHYL CINNAMATE (2-phenethyl 3-phenylprop-2-enoate) | 1870 | −2.9 |
| PHENYL ETHYL FORMATE (2-phenethyl formate) | 1105 | −2.1 |
| PHENYL ETHYL ISOBUTYRATE (2-phenethyl isobutanoate) | 1496 | −2.7 |
| PHENYL ETHYL ISOVALERATE (2-phenethyl 3-methylbutanoate) | 1625 | −2.2 |
| PHENYL ETHYL PHENYLACETATE (2-phenethyl 2-phenylacetate) | 1788 | −4.0 |
| PHENYL ETHYL SALICYLATE CRYSTALS (2-phenethyl 2-hydroxybenzoate) | 1721 | −5.0 |
| PHENYL PROPIONIC ALDEHYDE (3-phenylpropanal) | 1052 | −2.6 |
| PHENYL PROPYL ACETATE (3-phenylpropyl acetate) | 1367 | −1.7 |
| PHENYL PROPYL ALCOHOL (3-phenylpropan-1-ol) | 1081 | −2.3 |
| PINENE ALPHA (2,6,6-trimethylbicyclo[3.1.1]hept-2-ene) | 1196 | −0.7 |
| PINENE BETA (6,6-dimethyl-2-methylenebicyclo[3.1.1]heptane) | 1204 | −0.8 |
| PINO ACETALDEHYDE (3-(6,6-dimethylbicyclo[3.1.1]hept-2-en-2-yl)propanal) | 1483 | −4.0 |
| PIVACYCLENE ((3aR,6S,7aS)-3a,4,5,6,7,7a-hexahydro-1H-4,7-methanoinden-6-yl pivalate) | 1851 | −1.8 |
| PLICATONE ((4aS,8aR)-7-methyloctahydro-1,4-methanonaphthalen-6(2H)-one) | 1390 | −1.7 |
| POIRENATE (ethyl 2-cyclohexylpropionate) | 1499 | −1.3 |
| POMAROSE ((2E,5E)-5,6,7-trimethylocta-2,5-dien-4-one) | 1443 | −0.9 |
| PRECARONE ((1S,4R,6S)-4,7,7-trimethyl-4-(3-methylbut-2-en-1-yl)bicyclo[4.1.0]heptan-3-one) | 1887 | −3.3 |
| PRENYL ACETATE (3-methylbut-2-en-1-yl acetate) | 1039 | −2.2 |
| PROPYL DIANTILIS (2-ethoxy-4-(isopropoxymethyl)phenol) | 1606 | −2.0 |
| PRUNOLIDE (5-pentyldihydrofuran-2(3H)-one) | 1257 | −3.7 |
| QUINTONE (2-pentylcyclopentanone) | 1313 | −1.9 |
| RESEDAL (2-(cyclohexylmethyl)-4,4,6-trimethyl-1,3-dioxane) | 1726 | −1.4 |
| RHUBOFIX ((2R,8aS)-3',6-dimethyl-3,4,4a,5,8,8a-hexahydro-1H-spiro[1,4-methanonaphthalene-2,2'-oxirane]) | 1571 | −1.2 |
| RHUBOFLOR ((4aR,8aS,E)-6-ethylideneoctahydro-2H-5,8-methanochromene) | 1400 | −1.7 |
| ROSANTOLENE (1-(ethoxymethyl)-2-methoxybenzene) | 1277 | −2.2 |
| ROSAPHEN (2-methyl-5-phenylpentan-1-ol) | 1471 | −2.5 |
| ROSE OXIDE (4-methyl-2-(2-methylprop-1-en-1-yl)tetrahydro-2H-pyran) | 1320 | −2.4 |
| ROSSITOL (3-isobutyl-1-methylcyclohexanol) | 1489 | −2.3 |
| SAFRALEINE (2,3,3-trimethyl-2,3-dihydro-1H-inden-1-one) | 1390 | −1.8 |
| SAFRANAL (2,6,6-trimethylcyclohexa-1,3-dienecarbaldehyde) | 1263 | −2.4 |
| SANDELA CONCENTRATED (3-((1R,2S,4R,6R)-5,5,6-trimethylbicyclo[2.2.1]heptan-2-yl)cyclohexanol) | 1989 | −2.8 |
| SCENTENAL ((3aR,4R,6S,7R,7aR)-6-methoxyoctahydro-1H-4,7-methanoindene-1-carbaldehyde) | 1453 | −3.2 |
| SCLARENE (4,5,6,7,8,9,10,11,12,13-decahydrocyclododeca[d]oxazole) | 1680 | −1.7 |
| SHISOLIA (4-vinylcyclohex-1-enecarbaldehyde) | 1103 | −1.9 |
| SKATOLE (3-methyl-1H-indole) | 998 | −3.9 |
| SPIRAMBRENE (2',2',3,7,7-pentamethylspiro[bicyclo[4.1.0]heptane-2,5'-[1,3]dioxane]) | 2037 | −2.9 |
| STRAWBERRY PURE (ethyl methyl phenyl glycidate) | 1481 | −2.0 |
| STYRALLYL ACETATE (1-phenylethyl acetate) | 1246 | −2.0 |
| STYRALLYL PROPIONATE (1-phenylethyl propionate) | 1377 | −1.6 |
| SUPERFIX (1,1,3-trimethyl-3-phenyl-2,3-dihydro-1H-indene) | 1959 | −1.9 |
| SYRINGA ALDEHYDE (2-(p-tolyl)acetaldehyde) | 1046 | −3.0 |
| SYVERTAL (2-(heptan-3-yl)-1,3-dioxolane) | 1428 | −3.0 |
| TANAISONE ((Z)-1-(cyclooct-3-en-1-yl)ethanone) | 1275 | −1.4 |
| TANGERINOL ((E)-6,10-dimethylundeca-5,9-dien-2-yl acetate) | 2033 | −1.8 |
| TERPINENE ALPHA (1-methyl-4-propan-2-ylcyclohexa-1,3-diene) | 1194 | −0.5 |
| TERPINEOL PURE (2-(4-methylcyclohex-3-en-1-yl)propan-2-ol) | 1307 | −2.0 |
| TETRAHYDRO CITRAL (3,7-dimethyloctanal) | 1409 | −2.4 |
| TETRAHYDRO LINALYL ACETATE (3,7-dimethyloctan-3-yl acetate) | 1733 | −1.9 |
| THIOGERANIOL ((E)-3,7-dimethylocta-2,6-diene-1-thiol) | 1458 | −1.1 |
| THYMOL CRYSTALS (2-isopropyl-5-methylphenol) | 1217 | −1.8 |
| TIMBEROL (1-(2,2,6-trimethylcyclohexyl)hexan-3-ol) | 2040 | −2.1 |
| TOLYL ALDEHYDE PARA (4-methylbenzaldehyde) | 918 | −0.7 |

-continued

| Ingredient (NAME (IUPAC name)) | RECON_VOLTAE | Log Kcaps |
|---|---|---|
| TOSCANOL (1-(cyclopropylmethyl)-4-methoxybenzene) | 1261 | −1.9 |
| TRICYCLAL (2,4-dimethylcyclohex-3-enecarbaldehyde) | 1138 | −1.7 |
| TRIDECENAL-2-TRANS ((E)-tridec-2-enal) | 1744 | −2.5 |
| TRIFERNAL (3-phenylbutanal) | 1178 | −2.2 |
| TRIMOFIX O (1-((2E,5Z,9Z)-2,7,8-trimethylcyclododeca-2,5,9-trien-1-yl)ethanone) | 2093 | −3.0 |
| TROPIONAL (3-(benzo[d][1,3]dioxol-5-yl)-2-methylpropanal) | 1361 | −2.6 |
| ULTRAVANIL (2-ethoxy-4-methylphenol) | 1146 | −2.3 |
| UNDECALACTONE DELTA (6-hexyltetrahydro-2H-pyran-2-one) | 1507 | −3.3 |
| UNDECATRIENE ((3E,5Z)-undeca-1,3,5-triene) | 1379 | −0.8 |
| UNDECENE 2 NITRILE ((E)-undec-2-enenitrile) | 1559 | −1.5 |
| VALEROLACTONE GAMMA (5-methyloxolan-2-one) | 740 | −2.3 |
| VANILLIN (4-hydroxy-3-methoxybenzaldehyde) | 1043 | −3.1 |
| VANITROPE ((E)-2-ethoxy-5-(prop-1-en-1-yl)phenol) | 1363 | −1.9 |
| VELVIONE ((Z)-cyclohexadec-5-enone) | 2050 | −1.7 |
| VERDALIA ((3aS,4R,6S,7R,7aR)-6-methoxy-3a,4,5,6,7,7a-hexahydro-1H-4,7-methanoindene) | 1267 | −2.1 |
| VERDOL (2-(tert-butyl)cyclohexanol) | 1395 | −2.5 |
| VERNALDEHYDE (1-methyl-4-(4-methylpentyl)cyclohex-3-enecarbaldehyde) | 1826 | −2.3 |
| VERTOFIX COEUR (1-((1S,8aS)-1,4,4,6-tetramethyl-2,3,3a,4,5,8-hexahydro-1H-5,8a-methanoazulen-7-yl)ethanone) | 2094 | −1.9 |
| VETIKOL ACETATE/CORPS RHUBARB (4-methyl-4-phenylpentan-2-yl acetate) | 1803 | −2.4 |
| VETYNAL ((2R,5R,8S)-4,4,8-trimethyltricyclo[6.3.1.02,5]dodecan-1-yl acetate) | 2192 | −3.7 |
| VIOLET NITRILE ((2E,6Z)-nona-2,6-dienenitrile) | 1261 | −1.6 |
| VIOLIFF (undec-10-enenitrile) | 1400 | −1.5 |
| YARA YARA (2-methoxynaphthalene) | 1169 | −1.8 |

The encapsulated perfume compositions of the present invention may be presented in the form of at least one microcapsule dispersed in a suitable suspending medium.

Many different types of microcapsule compositions have been proposed in the art for encapsulating perfume compositions. The microcapsules of the present invention may be prepared using a range of conventional methods and materials known to those skilled in the art.

For example, microcapsules can be formed by physico-chemical means, such as internal phase separation, layer-by-layer poly-electrolyte deposition, sol-gel processes or coacervation; or by chemical means such as interfacial polymerisation, in-situ polymerisation and polycondensation.

The process of coacervation typically involves encapsulation of a generally water-insoluble material by the precipitation of colloidal material(s) onto the surface of droplets of perfume composition. Coacervation may be simple e.g. using one colloid such as gelatine, or complex where two or possibly more colloids of opposite charge, such as gelatine and gum arabic or gelatine and carboxymethylcellulose, are used under carefully controlled conditions of pH, temperature and concentration. Coacervation techniques are described, e.g. in U.S. Pat. Nos. 2,800,458, 2,800,457, GB929403, EP385534 and EP376385, which are herein incorporated by reference.

In a process of interfacial polymerization, two reactants that react by polycondensation meet at an oil-water interface to produce shells from the reaction of at least one oil-soluble wall forming material present in an internal oil phase with at least one water-soluble wall forming material present in an aqueous external phase. A polymerisation reaction between the two wall-forming materials occurs resulting in the formation of covalent bonds at the interface of the oil and aqueous phases to form a microcapsule wall. Examples of microcapsules produced by this method are polyamide and polyurethane microcapsules.

Polycondensation involves forming a dispersion or emulsion of perfume droplets in an aqueous continuous phase containing a pre-condensate of polymeric materials under appropriate conditions of agitation to produce microcapsules of a desired size, and adjusting the reaction conditions to cause condensation of the pre-condensate by acid catalysis, resulting in the condensate separating from solution and surrounding the dispersed perfume droplets to produce a coherent film and the desired microcapsules. Polycondensation techniques are described, e.g. in U.S. Pat. Nos. 3,516,941, 4,520,142, 4,528,226, 4,681,806, 4,145,184 and GB2073132, which are herein incorporated by reference.

A preferred method for forming microcapsules useful herein is polycondensation, typically to produce aminoplast and poylurea microcapsules.

Aminoplast resins are the reaction products of one or more amines with one or more aldehydes, typically formaldehyde. Non-limiting examples of suitable amines include urea, thiourea, melamine and its derivates, benzoguanamine and acetoguanamine and combinations of amines. For example, good results have been obtained with aminoplast capsules of mixed resins of urea/formaldehyde and melamine/formaldehyde, stabilized with maleic anhydride copolymers, as well as with aminoplast terpolymers, comprising polyamines, polyols and methylene oxide moieties, stabilized with acrlymidosulfonates copolymers, as described in WO 2008/098387.

The aminoplast microcapsules described in WO 2008/098387, which is incorporated herein in its entirety, are preferred encapsulating media for the encapsulated perfume compositions of the present invention.

Alternatively, microcapsules can be obtained by oil-mediated radical polymerization—phase separation, as described in U.S. Pat. No. 6,951,836 B2, or by interfacial radical polymerization.

An encapsulated perfume composition of the present invention may be prepared and presented in the form of a slurry, in which the microcapsules are dispered in an aqueous suspending medium. If it is intended to present the encapsulated perfume composition in this form, the pH of the slurry may be adjusted to about 3 to 8 by the addition of a suitable acid, such as citric acid or formic acid and a preservative added.

Slurries of microcapsules will typically contain a suspending aid to ensure the microcapsules remain stably suspended and do not cream, form a sediment or otherwise agglomerate during storage. Suitable dispersing aids include pectin, alginate, arabinogalactan, carageenan, gellan gum, xanthan gum, guar gum, acrylates/acrylic polymers, water-swellable clays, fumed silicas, acrylate/aminoacrylate copolymers, and mixtures thereof. Preferred dispersants herein include those selected from the group consisting of acrylate/acrylic polymers, gellan gum, fumed silicas, acrylate/aminoacrylate copolymers, water-swellable clays, and mixtures thereof.

In order to prevent microbial contamination it is desirable that the microcapsule composition contains a preservative. The preservative may be contained in the core material and/or in the aqueous carrier. Suitable preservatives include quaternary compounds, biguanide compounds, and mixtures thereof.

In addition to any perfume composition that may be contained within the microcapsules, a slurry of microcapsules of the present invention may also contain free perfume in the suspending medium.

Alternatively, the encapsulated perfume composition, initially presented in the form of a slurry, may be dried to provide an encapsulated perfume composition in powder form. Drying may be carried out directly by spray drying or by fluid bed drying. Alternatively, the encapsulated perfume composition can be dried by decanting off the liquid from the slurry and drying the solids in an oven to produce a cake, which can then be rendered in powder form by a subsequent comminution step.

Whatever means are employed to dry the encapsulated perfume composition, in order to prevent aggregation and improve the bulk flow properties of the microcapsules, it may be desirable to add a flow aid to the slurry before or after the drying process. Suitable flow aids will be known to the skilled person in the art and will include, without limitation silica, starch, calcium carbonate and sodium sulphate.

The size of the microcapsules employed in encapsulated perfume compositions according to the present invention can be adjusted as desired for use in any particular application. Microcapsules can be prepared having a mean diameter of from about 0.001 to about 1,000 microns, preferably from about 1 to about 500 microns, more preferably from about 10 to about 100 microns, and even more preferably from about 10 to about 70 microns.

The mean particle size can be determined in a manner known in the art. A particular method of measuring particle size is light scattering. Light scattering measurements can be made using a Malvern Mastersizer.

Encapsulated perfume compositions according to the present invention may be incorporated into all manner of consumer products, including those used in household, laundry and personal care products, including cosmetic products. Such consumer products are well known in the art and reference may be made to the following works which are incorporated herein by reference:

Formulating Detergents and Personal Care Products A guide to Product Development by L Ho Tan Tai, ISBN 1-893997-10-3 published by the AOCS Press. Also to Volume 67 of the Surfactant Science Series Liquid Detergents ISBN 0-8247-9391-9 (Marcel Dekker Inc).

The encapsulated perfume compositions may be incorporated into consumer products at levels that provide the consumer product with about 0.03 wt % to 1 wt % of encapsulated perfume composition based on the weight of the consumer product. The amount of encapsulated perfume composition that should be added to a consumer product base in order to arrive at this level of fragrance will depend on a number of factors, including the amount of perfume ingredients loaded into microcapsules, and the form in which the encapsulated perfume composition is incorporated into the base. Typically, the encapsulated perfume composition is incorporated in the form of a slurry containing about 20 to 50 wt %, and more particularly 30 to 45 wt % of microcapsules, wherein the microcapsules contain only perfume ingredients and no other diluents or solvents. In such a case, in order to provide the consumer product with the levels of perfume described above, one would typically incorporate between about 0.1 wt % to about 3 wt % of slurry into a consumer product base.

In a particular embodiment of the present invention, the consumer product is a fabric treatment product, such as a fabric conditioner or softener.

Fabric softener and conditioner ingredients and formulations are disclosed in U.S. Pat. Nos. 6,335,315; 5,674,832; 5,759,990; 5,877,145; and 5,574,179, which are hereby incorporated by reference.

Fabric conditioners or softeners typically comprise nitrogen-containing cationic surfactants having one or two alkyl chain comprising 16 to 22 carbon atoms, and optionally hydroxyl groups. The cationic group is preferably a quarternary ammonium, imidazolium group, and amido amine acid salts. The quaternary ammonium group has additionally two to three alkyl groups having 1 to 4 carbon or hydroxyalkyl or hydroxyl groups, or alkoxy groups, having typically about 1 to about 10 ethylene oxide moieties, and an anion selected from the group of halides, hydroxides, acetates and methylsulfate. The long alkyl chain is preferably bound to the cationic group by a ester group. Typical examples of such fabric conditioning actives include esterquat (N-methyl-N, N,bis[2-(C16-C18-acetoxy)ethyl)]-N-(2-hydroxyethyl) ammonium methosulfate), diesterquat (N,N,N-trimethyl-N-[1,2-di-(C16-C18-acyloxy)propyl ammonium salts), DEEDMAC (N,N-dimethyl-N,N-bis([2-(-[(1-oxooctadecyl)oxy] ethyl) ammonium chloride, HEQ (N,N,N-trimethyl-N—[(Z)-2-hydroxy-3-[(1-oxo-octadec-9-enyl)oxy]] ammonium chloride, TEAQ (diquaternized methylsulfate salt of the reaction product between C10-C20 staturated and unsaturated fatty acids and triethanoloamine), glycerine-based polyol esterquats, ethyl-tallowalkyl imidazolinium methyl sulphate, ditallowalkyl dimethylammonium methyl sulfate, methyl tallowalkyl amido ethyl tallowalkyl imidazolinium methyl sulfate, b-hydroxyethyl ethylenediamine erivatives, polyammonium and the like, and mixture thereof.

Further fabric softening actives are disclosed, for example, in Ajad Farooq and Charles J. Schramm, Handbook of Detergents—Part E: Applications, Surfactant Science Series 141, p. 181-200, CRC-Press, Broken Sound Parway, 2009.

Typical non-ionic surfactants that may be present in fabric conditioners or softeners include, but are not limited to alkyl and alkylbenzyl alcohol alkoxylates or polyalkoxylated carboxylic acids, polyalkoxylated amines, polyalkoxylated glycol or glycerol esters, polyalkoxylated sorbitan esters or alkanoamides.

In another embodiment of the invention, the consumer product may be a laundry detergent composition.

Laundry detergent ingredients and formulations are disclosed in U.S. Pat. Nos. 5,929,022; 5,916,862; 5,731,278; 5,470,507; 5,466,802; 5,460,752; and 5,458,810, which are hereby incorporated by reference.

Powdered or liquid detergents typically comprise anionic, zwitterionic and/or non-ionic surfactants, and mixtures thereof.

Typical anionic surfactants include sodium lauryl sulfate, sodium laureth sulfate, sodium trideceth sulfate, ammonium lauryl sulfate, ammonium laureth sulfate, potassium laureth sulfate, linear alkyl benzene sulfonates, sodium tridecyl benzene sulfonate, sodium dodecyl benzene sulfonate, sodium xylene sulfonate, monoethanolamine lauryl sulfate, monoethanolamine laureth sulfate, triethanolamine lauryl sulfate, triethanolamine laureth sulfate, lauryl sarcosine, cocoyl sarcosine, sodium lauryl sarcosinate, sodium lauroyl sarcosinate, triethylamine lauryl sulfate, triethylamine laureth sulfate, diethanolamine lauryl sulfate, diethanolamine laureth sulfate, lauric monoglyceride sodium sulfate, ammonium cocoyl sulfate, ammonium lauroyl sulfate, sodium cocoyl sulfate, sodium lauroyl sulfate, sodium cocoyl isethionate, potassium cocoyl sulfate, potassium lauryl sulfate, monoethanolamine cocoyl sulfate, monoethanolamine lauryl sulfate, triethanolamine lauryl sulfate, C5-C17 acyl-N—(C1-C4 alkyl) glucamine sulfate, C5-C17 acyl-N—(C1-C4 hydroxyalkyl) glucamine sulfate, sodium hydroxyethyl-2-decyl ether sulfates, sodium methyl-2-hydroxydecyl ether sulfates, sodium hydroxyethyl-2-dodecyl ether sulfates, sodium monoethoxylated lauryl alkyl sulfates, C12-C18 alkyl sulfonates, ethoxylated or native linear and ramified C12-C18 alcohol sulfates, ethoxylated or native linear and ramified C12-C18 alcohol sulfates, and mixtures thereof. Above anionic surfactants may also be used in their un-neutralized, acid form.

Typical non-ionic surfactants include C6-C24 alkyl ethoxylates with about 1-12 ethylene oxide units. The alkyl chain of the aliphatic alcohol can either be straight or branched, primary or secondary, and generally contains from about 6 to about 22 carbon atoms. Further examples of non-ionic surfactants include the condensation products of fatty acids with glucamines, such as C12-C16 akyl N-methyl glucamide, and/or the condensation product of fatty acids with eth-oxylated amines; C10-C20 alkyl mono- or di-alkanolamides, where the alkyloxy group has 1 to 3 carbon atoms, C10-C20 alkyl mono- or di-alknolamide having an intermediate polyoxyalkylene moiety having 2 to 20 alkyleneoxide groups between the alkyl moiety and the alkanolamide moiety; alkyl amidopropyl dimethylamine; fatty acid alkyl esters, such as sorbitol esters with oleic, myristic, stearic, palmitic acid, and the like, also known under the trade name Tween, such as Tween 20, Tween 40, and Tween 60; alkyl polyglycosides including, for example, C8-C10 alkyl polyglycosides, C12-C16 alkyl polyglycosides, C5 Amyl. Further non-ionic surfactants include glycerol-based surfactants, such as fatty acid polyglyceryl esters like octanoic acid hexaglyceryl ester, decanoic acid tetraglyceryl ester, riccinoleic acid hexaglyceryl ester and cocoic acids tetraglyceryl esters and their mixtures. The term "alkyl" as used hereinabove for the non-ionic sugar-based surfactant refers to saturated linear alkyl residues having 3 to 21 carbon atoms, including hexyl, octyl, decanyl, dodecanyl, tetradecanyl, hexa-decanyl, and octadecanyl.

Typical zwitterionic surfactants include but are not limited to derivatives of aliphatic quaternary ammonium, phosphonium, and sulfonium compounds having linear or ramified alkyl, or alkenyl, or hydroxyl alkyl or alkoxy radicals, one of which having from about 8 to about 18 carbon atoms and another of which containing an anionic group selected from carboxyl, sulfonate, sulfate, succinate, phosphate or phosphonate groups. The alkoxy radicals include typically about 1 to about 10 ethylene oxide moieties or about 1 to about 3 glyceryl moieties. The hydroxyl alkyl radicals comprise typically alkylol moieties having 1 to 3 carbon atoms. A particular class of zwitterionic surfactants includes betaines comprising a quaternized cationic ammonium group and an anionic carboxylate group, separated by at least one methylene group, such as coco dimethylcarboxymethyl betaine, lauryl dimethyl carboxymethyl betaine, lauryl dimethyl alphacarboxyethyl betaine, cetyl dimethyl carboxymethyl betaine, oleyl dimethyl gammacarboxypropyl betaine, lauryl and stearyl bis-(2-hydroxyethyl) carboxymethyl betaine, oleyl dimethyl gammacarboxypropyl betaine, and lauryl bis-(2-hydroxypropyl)alphacarboxyethyl betaine. Other betaines include amidoalkyl, sulfoalkyl and alkyl amidosufo beta-ines, wherein the alkyl moiety is typically an ethyl or a propyl moiety, such as cocoamidopropyl betaine, cocodimethylsulfopropyl betaine, lauryl dimethyl sulfoethyl betaine, lauryl bis-(2-hydroxyethyl) sulfopropyl betaine and the like. Another particular class of zwitterionic surfactants includes sultaines, hydroxysultaines and amidopropyl hydroxysultaines.

Typical Zwitterionic and semi-polar surfactants include water-soluble amine oxides, such as C10-C18 alkyl dimethyl amine oxides and C8-C12 alkoxy ethyl dihydroxy ethyl amine oxides, such as NN-dihydroxyethyl-N-stearamine oxide, ethoxylated lauramide and lauryldimethylamine oxide, also known under the name Lauramine oxide ("LO"), and alkyl amphocarboxylic acids, such as disodium cocoamphodiacetate.

Liquid or solid laundry detergent compositions may be provided in the form of single unit doses contained, for example, in water-dissolvable packaging, such as pouches or pods. Because these products are single dose and of relatively small size (typically about 10 to 20 ml volume), they are provided with a relatively low dose of detergent composition, and furthermore, because the packaging enclosing the detergent is water-soluble, or at least disintegrates readily in water, the composition necessarily contains a small volume of highly concentrated surfactant, and therefore represents a very aggressive medium in which to incorporate microcapsules.

In pouches comprising laundry, laundry additive and/or fabric conditioning compositions, the compositions may comprise one or more of the following non-limiting list of ingredients: fabric care benefit agent; detersive enzyme; deposition aid; rheology modifier; builder; bleach; bleaching agent; bleach precursor; bleach booster; bleach catalyst; polyglycerol esters; whitening agent; pearlescent agent; enzyme stabilizing systems; scavenging agents including fixing agents for anionic dyes, complexing agents for anionic surfactants, and mixtures thereof; optical brighteners or fluorescers; polymer including but not limited to soil release polymer and/or soil suspension polymer; dispersants; antifoam agents; non-aqueous solvent; fatty acid; suds suppressors, e.g., silicone suds suppressors (see: U.S. Publication No. 2003/0060390 A1, ¶ 165-77); cationic starches (see: US 2004/0204337 A1 and US 2007/0219111 A1); scum dispersants (see: US 2003/0126282 A1); substantive dyes; hueing dyes (see: US 2014/0162929A1); colorants; opacifier; antioxidant; hydrotropes such as toluenesulfonates, cumenesulfonates and naphthalenesulfonates; color speckles; colored beads, spheres or extrudates; clay softening agents; anti-bacterial agents. Additionally or alternatively, the compositions may comprise surfactants, quaternary ammonium compounds, and/or solvent systems.

The detergent compositions can comprise from about 1 wt % to 80 wt % by weight of a surfactant. Detersive surfactants utilized can be of the anionic, nonionic, zwitterionic or cationic type or can comprise compatible mixtures of these types. More preferably surfactants are selected from the group consisting of anionic, nonionic, cationic surfactants and mixtures thereof. Detergent surfactants useful herein are described in U.S. Pat. Nos. 3,664,961; 3,919,678; 4,222,905; and 4,239,659. Anionic and nonionic surfactants are preferred. Useful anionic, nonionic, zwitterionic or cationic type surfactants are those described above.

Laundry detergent compositions may have a pH of about 6 to about 10, about 6.5 to about 8.5, about 7 to about 7.5, or about 8 to about 10, wherein the pH of the detergent is defined as the pH of an aqueous 10% (weight/volume) solution of the detergent at 20±2° C.

In yet another embodiment of the present invention the consumer product is a personal care product, such as shampoos, hair conditioners and personal cleansing compositions. Examples of shampoos and hair conditioner formulations and ingredients are described in U.S. Pat. Nos. 6,162,423; 5,968,286; 5,935,561; 5,932,203; 5,837,661; 5,776,443; 5,756,436; 5,661,118; and 5,618,523.

Hair cleansing compositions—shampoos—comprise at least one surfactant selected from anionic, non-ionic and/or zwitterionic surfactants, typically at a concentration range of 2 to 60 wt %, more particularly 5 to 50 wt % and more particularly 5 to 40 wt % based on the total weight of the composition.

Any of the anionic, non-ionic and/or zwitterionic surfactants referred to above may be employed in hair cleansing compositions.

Anionic surfactants may be present in an amount from 1 to about 30 wt %, particularly 2 to 25 wt % and most particularly 2-20 wt %.

Non-ionic surfactants may be employed in an amount from about 0.25 wt % to about 5 wt %, particularly about 0.5 wt % to about 3.5 wt % based on the total composition.

Zwitterionic surfactants may be employed in an amount of about 0.5 wt % to about 10 wt %, more particularly from about 1 wt % to about 7.5 wt % by weight based on the total weight of the composition.

Hair conditioning compositions of the present invention can be in the form of either leave in or rinse off compositions.

Preferred surfactants are non-ionic and cationic types and they may be employed in the amounts referred to above in relation to the hair cleaning compositions.

Suitable cationic surfactants and or conditioning agents are, for example, long-chain quaternary ammonium compounds which can be used alone or in admixture with one another, such as cetyl trimethyl ammonium chloride, myristoyl trimethyl ammonium chloride, trimethyl cetyl ammonium bromide, stearyl trimethyl ammonium chloride, dimethyl stearyl ammonium chloride, dimethyl dihydrogenated tallow ammonium chloride, stear trimonium chloride, dipalmitoyl dimonium chloride, distearyl dimethyl ammonium chloride, stearamidopropyl trimonuim chloride, and dioleoylethyl dimethyl ammonium methosulfate.

Particularly useful are so-called esterquats, which are well known commercial ingredients, such as those available under the trade names "Schercoquat™", "Dehyquart™ F30" and "Tetranyl™". Use of the esterquats in hair care compositions is described, for example, in WO-A 93/107 48, WO-A 92/068 99 and WO-A 94/166 77.

Hair conditioning compositions may contain cationic polymers as conditioning agents. Cationic conditioning agents include but are not limited to cellulose type polymers, such as Polyquaternium 10 or cationic guar gum, such as Guar hydroxypropyl trimonium chloride. Other cationic conditioning agents include natural cationic polymers, such as chitosan and chitin. Other polymers include Polyquaternium 6, Polyquaternium 7, Polyquaternium 10, Polyquaternium 11, Polyquaternium 16, Polyquaternium 22 and Polyquaternium 28, Polyquaternium 30, Polyquaternium 37, Polyquaternium 36, and Polyquaternium 46. Still further, Quaternium-8, Quaternium-14, Quaternium-15, Quaternium-18, Quaternium-22, Quatemium-24, Quaternium-26, Quaternium-27, Quatemium-30, Quatemium-33, Quaternium-53, Quatemium-60, Quaternium-61, Quaternium-72, Quatemium-78, Quaternium-80, Quaternium-81, Quaternium-81, Quaternium-82, Quaternium-83 and Quatemium-84. It is also possible to use mixtures of various cationic polymers.

The cationic polymers may also include the quatemized products of graft polymers from organopolysiloxanes and polyethyl oxazolines, as described, for example in EP-A 524 612 and EP-A 640 643.

Typically, a hair conditioning composition might contain between 0.01 wt % to 7.5 wt %, preferably 0.05 wt % to 5 wt % of said conditioning agents based on the total weight of the composition.

Other conditioning agents might include volatile or non-volatile silicone oils, including dimethicone, dimethiconol, polydimethylsiloxane, such as the DC fluid ranges available from Dow Corning. Also suitable are natural oils, such as olive oil, almond oil, avocado oil, ricinus oil, coconut oil, palm oil, sesame oil, peanut oil, whale oil, sunflower oil, peach kernel oil, wheat germ oil, macadamia nut oil, night primrose oil, jojoba oil, castor oil, or soya oil, lanolin and the derivatives thereof, as well as mineral oils such as paraffin oil and petrolatum.

Non-ionic conditioning agents may be polyols such as glycerin, glycol and derivatives, polyethyleneglycoles known with trade names Carbowax PEG from Union Carbide and Polyox WSR range from Amerchol, polyglycerin, polyethyleneglycol mono or di fatty acid esters.

Typical concentration range for any of the additional non-cationic conditioning agents mentioned above can be 0.01 wt % to 15 wt % based on the total weight of the composition. They may additionally contain at least one saturated or unsaturated fatty alcohol. Fatty alcohols include but are not limited to myristyl alcohol, palmityl alcohol, cetyl alcohol, stearyl alcohol, behenyl alcohol and their mixtures. The concentration of the fatty alcohol may be less than 20 wt % based on the total weight of the composition.

Conditioner compositions are disclosed in US 2015/0157550, which is hereby incorporated by reference.

EXAMPLE 1

Encapsulated Perfume Compositions for use in Fabric Care Conditioners

Microcapsules were prepared according to the method set forth in WO/2008/098387, example 1.3, sample P5.2, using different perfumes having variable RECON_VOLTAE, $\log_{10}$ Kcaps and PROC values. The solid content of the capsule slurries was 40±2 wt %, wherein "solid content" refers to the percentage by weight of perfume-containing microcapsules in the slurry. In each case, an amount of slurry equivalent to 0.2 wt % of microcapsules was added to a fabric care softener composition having the formula described in Table 1.2. The perfume compositions are reported in Tables 1.1.1 through 1.1.4.

TABLE 1.1.1

| | | Perfume composition 1.A | | | |
|---|---|---|---|---|---|
| RECON_VOLTAE Distribution | C [%] | Average RECON_VOLTAE [Bohr$^3$] | Average LogKcaps | Average Odour Value | Sum pPROC |
| RECON_VOLTAE > 1750 | 0.7 | 1832 | −2.5 | 212968 | 7.48E+04 |
| 1540 < RECON_VOLTAE > 1750 | 8.7 | 1717 | −1.8 | 365443 | 5.10E+06 |
| 1200 < RECON_VOLTAE < 1540 | 63.1 | 1381 | −1.8 | 685319 | 7.31E+07 |
| < RECON_VOLTAE 1200 | 27.5 | 1174 | −0.7 | 5129911 | 2.50E+08 |

Perfume 1.A had 27.5 wt % of encapsulated perfume ingredients having RECON_VOLTAE lower than 1200; 72.5 wt % of ingredients having RECON_VOLTAE higher than 1200; 9.4 wt % of ingredients having RECON_VOLTAE higher than 1540; and 0.7 wt % of ingredients having RECON_VOLTAE higher than 1750. The total pre-rub odour contribution (tPROC) was 3.3×10$^8$. In table 1.1.1, all averages are weighted averages. RECON_VOLTAE<1200 means that RECON_VOLTAE can have any value between from 1 to 1199; 1200<RECON_VOLTAE<1540 means that RECON_VOLTAE can have any value between 1200 and 1539. RECON_VOLTAE>1750 means that RECON_VOLTAE can have any value between from 1750 upwards.

Perfume 1.0 had 4.0 wt % of ingredients having RECON_VOLTAE lower than 1200; 96 wt % of ingredients having RECON_VOLTAE higher than 1200; 69.6 wt % of ingredients having RECON_VOLTAE higher than 1540; and 22.0 wt % of ingredients having RECON_VOLTAE higher than 1750. The total pre-rub odour contribution (tPROC) was 2.1×10$^8$. In table 1.1.3, all averages are weighted averages. RECON_VOLTAE<1200 means that RECON_VOLTAE can have any value between from 1 to 1199; 1200<RECON_VOLTAE<1540 means that RECON_VOLTAE can have any value between 1200 and 1539. RECON_VOLTAE>1750 means that RECON_VOLTAE can have any value between from 1750 upwards.

TABLE 1.1.2

| | | Perfume composition 1.B | | | |
|---|---|---|---|---|---|
| RECON_VOLTAE Distribution | C [%] | Average RECON_VOLTAE [Bohr$^3$] | Average LogKcaps | Average Odour Value | Sum pPROC |
| RECON_VOLTAE > 1540 | 41.1 | 1661 | −1.9 | 1384185 | 5.58E+07 |
| 1200 < RECON_VOLTAE < 1540 | 53.1 | 1397 | −2.0 | 2555236 | 2.66E+08 |
| RECON_VOLTAE < 1200 | 5.8 | 1139 | −1.8 | 2095237 | 2.21E+07 |

Perfume 1.B had 5.8 wt % of ingredients having RECON_VOLTAE lower than 1200; 94.2 weight percent wt % of ingredients having RECON_VOLTAE higher than 1200; 41.1 wt % of ingredients having RECON_VOLTAE higher than 1540; and 0 wt % of ingredients having RECON_VOLTAE higher than 1750. All ingredients had log$_{10}$ Kcaps higher than −3, except the ALDEHYDE ISO C 11 and PEACH PURE. The total pre-rub odour contribution (tPROC) was 3.3×10$^8$. In table 1.1.2, all averages are weighted averages. RECON_VOLTAE<1200 means that RECON_VOLTAE can have any value between from 1 to 1199; 1200<RECON_VOLTAE<1540 means that RECON_VOLTAE can have any value between 1200 and 1539. RECON_VOLTAE>1540 means that RECON_VOLTAE can have any value between from 1750 upwards.

TABLE 1.1.3

| | | Perfume composition 1.C | | | |
|---|---|---|---|---|---|
| RECON_VOLTAE Distribution | C [%] | Average RECON_VOLTAE [Bohr$^3$] | Average LogKcaps | Average Odour Value | Sum pPROC |
| FATTY ESTER | 10.4 | 2379 | −1.3 | 0 | 0.00E+00 |
| RECON_VOLTAE > 1750 | 11.6 | 2085 | −2.8 | 7258 | 6.97E+04 |
| 1540 < RECON_VOLTAE < 1750 | 47.6 | 1665 | −1.9 | 8152 | 4.00E+05 |
| 1200 < RECON_VOLTAE < 1540 | 26.4 | 1346 | −2.0 | 3965938 | 2.05E+08 |
| RECON_VOLTAE < 1200 | 4.0 | 1155 | −2.5 | 166482 | 4.61E+05 |

TABLE 1.1.4

| | | Perfume composition 1.D | | | |
|---|---|---|---|---|---|
| RECON_VOLTAE Distribution | C [%] | Average RECON_VOLTAE [Bohr$^3$] | Average LogKcaps | Average Odour Value | Sum pPROC |
| RECON_VOLTAE > 1750 | 4.1 | 2003 | −2.0 | 32323 | 1.10E+05 |
| 1540 < RECON_VOLTAE < 1750 | 60.1 | 1662 | −2.2 | 844432 | 7.54E+07 |
| <1200 RECON_VOLTAE < 1540 | 35.0 | 1371 | −1.4 | 1573063 | 1.08E+08 |
| RECON_VOLTAE < 1200 | 0.8 | 1138 | −1.9 | 811379 | 7.55E+05 |

Perfume 1.D had 0.8 wt % of ingredients having RECON_VOLTAE lower than 1200; 99.2 wt 15% of ingredients having RECON_VOLTAE higher than 1200; 64.2 wt % of ingredients having RECON_VOLTAE higher than 1540; and 4.1 wt % of ingredients having RECON_VOLTAE higher than 1750. The total pre-rub odour contribution (tPROC) was 1.64×10$^8$. In table 1.1.4, all averages are weighted averages. RECON_VOLTAE<1200 means that RECON_VOLTAE can have any value between from 1 to 1199; 1200<RECON_VOLTAE<1540 means that RECON_VOLTAE can have any value between 1200 and 1539. RECON_VOLTAE>1750 means that RECON_VOLTAE can have any value between from 1750 upwards.

TABLE 1.2

| | Fabric care softener composition | |
|---|---|---|
| Ingredient | Chemical nature | Percentage |
| Magnesium chloride | | 1 wt % |
| REWOQUAT WE 18 (ex REWO) | Di-(tallow-carboxyethyl)-hydroxyethyl methylammonium methosulfate | 12 wt % |
| GENAPOL O 100 (ex HOECHST) | Ethoxylated fatty alcohol (C16-18; 10 EO) | 2 wt % |
| ANTIFOAM 110A (EU) (ex DOW CORNING) | Polydimethylsiloxane emulsion stabilized with hydroxyethyl cellulose | 1 wt % |
| MYACIDE BT 30 (ex BOOTS) | 2-bromo-2-nitropropane-1,3-diol | 0.03 wt % |
| PROXEL GXL (ex ICI) | Benzisothiazolinone | 0.02 wt % |
| DEIONIZED WATER | | sq. 100 wt % |

The fabric care softener compositions containing the perfume compositions set forth in Tables 1.1.1 through 1.1.4 were put in a cupboard maintained at 37° C. with a thermostat for one month and the amount of free perfume having leached from the capsules was determined using the method described in Example 5, below.

EXAMPLE 2

Encapsulated Perfume Compositions for use in Liquid Detergent Tabs

Aminoplast microcapsules were prepared according to the following method:
1. Adding and dissolving a polymer stabilizer (Lupasol PA 140, ex BASF) in water under moderate shear mixing.
2. Adjusting the temperature to 35±2° C., the pH to 4.6±2 with NaOH, then adding an an alkylolated triamine pre-condensate (Luracoll SD, ex BASF), urea and perfume composition.
3. Emulsifying the system under moderate to high shear mixing, wherein the stirring speed and the geometry of the mixer is defined as a function of the desired average microcapsule size range and microcapsule size distribution.
4. Increasing the temperature to 88° C.±1° C. over a period of 75 min, then leaving the reaction at 88 C±2° C. during 2 h15.
5. Increasing the temperature to 88° C.±1° C. over a period of 75 min, then leaving the reaction at 88 C±2° C. during 35 min. Adding a second portion of the alkylolated triamine or triamine pre-condensates and formic acid.
6. Adding ethylene urea as formaldehyde scavenger while the slurry is still hot (88° C.) for 10 min
7. Cooling the system to room temperature.
8. Adding Carbopol under solution and leave the agitation constant 1 h, at 129 rpm, then adding NaOH and optionally adjusting pH within the range from 6 to 6.6 with formic acid The perfume compositions employed in the process described above are reported in Tables 2.1.A and 2.1.B. The solid content of the capsule slurries was 30±2 wt %, whereas the solid content refers to weight of perfume-containing capsules (wt %). In each case, an amount of slurry equivalent to 0.2 wt % of perfume-containing capsules was added to a liquid detergent tab base composition having the formula described in Table 2.2.

TABLE 2.1.1

| | | Perfume composition 2.A | | | |
|---|---|---|---|---|---|
| RECON_VOLTAE Distribution | C [%] | Average RECON_VOLTAE [Bohr$^3$] | Average LogKcaps | Average Odour Value | Sum pPROC |
| RECON_VOLTAE > 1750 | 18.6 | 1845 | −2.3 | 69384 | 8.35E+05 |
| 1540 < RECON_VOLTAE < 1750 | 22.3 | 1666 | −2.0 | 12520902 | 2.79E+08 |
| 1200 < RECON_VOLTAE < 1750 | 53.7 | 1386 | −2.0 | 1387064 | 1.09E+08 |
| RECON_VOLTAE < 1200 | 5.5 | 1100 | −1.8 | 69302 | 4.57E+05 |

Perfume 2.A had 5.5 wt % of ingredients having RECON_VOLTAE lower than 1200; 94.5 wt % of ingredients having RECON_VOLTAE higher than 1200; 40.9 wt % of ingredients having RECON_VOLTAE higher than 1540; and 18.6 wt % of ingredients having RECON_VOLTAE higher than 1750. The total pre-rub odour contribution (tPROC) was $3.9 \times 10^8$. In table 2.1.1, all averages are weighted averages. RECON_VOLTAE<1200 means that RECON_VOLTAE can have any value between from 1 to 1199; 1200<RECON_VOLTAE<1540 means that RECON_VOLTAE can have any value between 1200 and 1539. RECON_VOLTAE>1750 means that RECON_VOLTAE can have any value between from 1750 upwards.

TABLE 2.1.2

Perfume composition 2.B

| RECON_VOLTAE Distribution | C [%] | Average RECON_VOLTAE [Bohr³] | Average LogKcaps | Average Odour Value | Sum pPROC |
|---|---|---|---|---|---|
| RECON_VOLTAE > 1750 | 6.6 | 1966 | −1.5 | 54255 | 5.42E+05 |
| 1540 < RECON_VOLTAE < 1750 | 59.9 | 1677 | −2.3 | 50774 | 2.26E+06 |
| 1200 < RECON_VOLTAE < 1540 | 26.4 | 1374 | −1.7 | 4034852 | 1.39E+08 |
| RECON_VOLTAE < 1200 | 7.1 | 1155 | −1 | 361183 | 4.45E+06 |

Perfume 2.B had 7.1 wt % of ingredients having RECON_VOLTAE lower than 1200; 92.9 wt % of ingredients having RECON_VOLTAE higher than 1200; 66.5 wt % of ingredients having RECON_VOLTAE higher than 1540; and 6.6 wt % of ingredients having RECON_VOLTAE higher than 1750. The total pre-rub odour contribution (tPROC) was $1.5 \times 10^8$. In table 2.1.2, all averages are weighted averages. RECON_VOLTAE<1200 means that RECON_VOLTAE can have any value between from 1 to 1199; 1200<RECON_VOLTAE<1540 means that RECON_VOLTAE can have any value between 1200 and 1539. RECON_VOLTAE>1750 means that RECON_VOLTAE can have any value between from 1750 upwards.

TABLE 2.2

Liquid detergent tab base composition

| Ingredient | Chemical nature | Percentage |
|---|---|---|
| DEIONIZED WATER | | 10 wt % |
| PROPYLENE GLYCOL (ex MERCK) | | 20 wt % |
| GLYCEROL (ex Merck) | Propan-1,2,3 triol | 18.5 wt % |
| TEXAPON N 70 (ex COGNIS) | Sodium Lauryl Ether Sulfate + 2EO | 16.33 wt % |
| BIO SOFT LA ACID (ex STEPAN) | Acid benzenesulfonic | 5 wt % |
| LASACID FC 12 (ex LASCARAY SA) | Lauric acid 99% | 5 wt % |
| M.E.A (ex BASF) | Monoethanolamine | 10 wt % |
| NEODOL 25-7 (ex CALDIC) | Ethoxylated Alcohol C12-C15 | 15 wt % |
| BRONIDOX L (ex COGNIS) | 2-bromo-2-nitropropane | 0.03 wt % |

The liquid detergent base containing above perfume compositions were put in a thermostated cupboard at 37° C. for one month and the amount of free perfume having leached from the capsules was determined using the method described in Example 5.

EXAMPLE 3

Perfume Compositions for use in Hair Care Conditioners

Polyurea core-shell capsules were prepared by polycondensation of polyisocyanates and polyamines, according to the procedure disclosed WO 2011/160733 A1. The perfume compositions are reported in Table 3.1. The solid content of the capsule slurries was 40±2 wt %.

TABLE 3.1

Perfume 3 A composition

| RECON_VOLTAE Distribution | C [%] | Average RECON_VOLTAE [Bohr³] | Average LogKcaps | Average Odour Value | Average pPROC |
|---|---|---|---|---|---|
| RECON_VOLTAE > 1750 | 4.6 | 1822 | −1.9 | 11675 | 5.96E+04 |
| 1540 < RECON_VOLTAE < 1750 | 41.4 | 1679 | −2.0 | 210856 | 1.15E+07 |
| 1200 < RECON_VOLTAE < 1540 | 43.2 | 1415 | −2.5 | 188189 | 4.91E+06 |
| RECON_VOLTAE < 1200 | 11.0 | 1032 | −1.9 | 3559766 | 4.25E+07 |

Perfume 3 A had 11.0 wt % of ingredients having RECON_VOLTAE lower than 1200; 89.0 wt % of ingredients having RECON_VOLTAE higher than 1200; 45.8 wt % of ingredients having RECON_VOLTAE higher than 1540; and 4.6 wt % of ingredients having RECON_VOLTAE higher than 1750. The total pre-rub odour contribution (tPROC) was $5.9 \times 10^7$. In table 3.1, all averages are weighted averages. RECON_VOLTAE<1200 means that RECON_VOLTAE can have any value between from 1 to 1199; 1200<RECON_VOLTAE<1540 means that RECON_VOLTAE can have any value between 1200 and 1539. RECON_VOLTAE>1750 means that RECON_VOLTAE can have any value between from 1750 upwards.

TABLE 4.2

Hair conditioner composition

| Ingredient | Chemical nature | Percentage |
|---|---|---|
| PHENONIP (ex CLARIANT) | Phenoxyethanol and Butyl and Ethyl and Propyl parabens | 0.7 wt % |
| LANETTE 16 (ex COGNIS) | Cetyl alcohol | 1.0 wt % |
| BRIJ 721 (ex UNIQEMA/MASSO) | Steareth 21 | 2.0 wt % |
| STEARAFINE PURE (ex LASERSON) | Stearyl alcohol | 1.0 wt % |
| PROPYLENE GLYCOL (ex PRODH'YG) | | 4.0 wt % |
| NATROSOL 250H (ex AQUALON) | Hydroxyethyl cellulose | 0.9 wt % |
| INCROQUAT CTC 30 (ex CRODA) | Cetrimonium chloride | 2.00 wt % |
| DEIONISED WATER | | q.s.p. 100 wt % |

The hair conditioner base containing above perfume compositions were put in a thermostated cupboard at 37° C. for one month and the amount of free perfume having leached from the capsules was determined using the method described in Example 5.

EXAMPLE 4

Perfume Compositions for use in Shampoo

Polyurea core-shell capsules were prepared by polycondensation of polyisocyanates and polyamines, according to the procedure disclosed WO 2011/160733 A1. The perfume composition is reported in Table 4.1. The solid content of the capsule slurries was 40±2 wt %.

TABLE 4.1

Perfume composition 4 A

| RECON_VOLTAE Distribution | C [%] | Average RECON_VOLTAE [Bohr³] | Average LogKcaps | Average Odour Value | Sum pPROC |
|---|---|---|---|---|---|
| RECON_VOLTAE > 1750 | 89.1 | 2226 | −1.8 | 9253 | 1.23E+06 |
| 1450 < RECON < 1750 | 5.9 | 1573 | −2.2 | 355731 | 1.68E+06 |
| 1200 < RECON VOLTAE < 1540 | 4 | 1417.698 | −1.747203 | 207333 | 1.04E+06 |
| RECON VOLTAE < 1200 | 1 | 885.487 | −2.7870302 | 10337115 | 1.95E+07 |

Perfume 4 A had 1 wt % of ingredients having RECON_VOLTAE lower than 1200; 95% of ingredients having RECON_VOLTAE higher than 1540 and 89.1 wt % of ingredients having RECON_VOLTAE higher than 1750. The total pre-rub odour contribution (tPROC) was $2.3 \times 10^7$. In table 4.1, all averages are weighted averages. RECON_VOLTAE<1750 means that RECON_VOLTAE can be any value between from 1 to 1749. RECON_VOLTAE>1750 means that RECON_VOLTAE can be any value between from 1750 upwards.

TABLE 4.2

Shampoo base composition

| Ingredient | Chemical nature | Percentage |
|---|---|---|
| DEIONIZED WATER | | 67.00 wt % |
| PROPYLENE GLYCOL (ex MERCK) | | 0.67 wt % |
| JR-125 (ex RHODIA) | Polyquaternium-10 | 0.17 wt % |
| GENAPOL LRO LIQ (ex CLARIANT) | Sodium Laureth Sulfate | 20.09 wt % |
| DEHYTON AB 30 (ex COGNIS) | Coco Betaine | 4.02 wt % |
| GLYDANT PLUS LIQ (ex LONZA) | DMDM Hydantoin | 0.33 wt % |
| TRILON B (ex BASF) | Tetrasodium EDTA | 0.03 wt % |
| SODIUM CHLORIDE (ex MERCK) | | 1.00 wt % |

The shampoo base containing above perfume compositions were put in a thermostated cupboard at 37° C. for one month and the amount of free perfume having leached from the capsules was determined using the method described in Example 5.

EXAMPLE 5

Determination of Capsule Leakage in Consumer Product Bases 1 g of consumer product base sample, previously filtered through a 5 micrometre syringe filter was accurately weighed in a 30 ml flask. 1 g of Celite 545 was added and admixed with the sample. 10 ml of pentane was then added together with 0.5 mg of internal standard (Methyl decanoate 99% Aldrich ref 299030) to the sample. The whole was stirred for 30 minutes using a magnetic stirrer. The pentane phase was then removed and an aliquot of 2 microlitre was injected in a gas chromatograph (GC) equipped with a splitless injector and a flame ionization detector. The initial temperature of the GC oven was 70° C., the final temperature, 240° C. and the rate of hating was set to 2° C./min. The temperature of the injector was 250° C. A RTX1 GC column with dimensions 60 m*0.25 µm*0.25 µm was used.

Table 3.1 summarizes the results from capsule leakage analysis, along with RECON_VOLTAE and PROC values.

TABLE 3.1

| Perfume Composition/ Application Capsules | Ingredients with RV > 1200 (wt %) | Ingredients with 1200 < RV < 1540 (wt %) | Ingredients with RV > 1540 (wt %) | Ingredients with RV > 1750 (wt %) | Total PROC | LEAKAGE 1 month 37° C. (wt %) |
|---|---|---|---|---|---|---|
| 1.A/Fabric care softener Aminoplast | 72.5 | 63.1 | 9.4 | 0.7 | $3.4 \times 10^8$ | 72.6 |
| 1.B/Fabirc care softener; Aminoplast | 94.2 | 53.1 | 41.1 | 0.0 | $3.5 \times 10^8$ | 47.0 |
| 1.C/Fabric care softener; Aminoplast | 96.0 | 26.4 | 69.6 | 22.0 | $2.1 \times 10^8$ | 20.2 |
| 1.D/Fabric care softener; Aminoplast | 99.2 | 35 | 64.2 | 4.1 | $1.7 \times 10^8$ | 14.6 |
| 2 A/liquid detergent tabs Aminoplast | 94.5 | 53.7 | 40.9 | 18.6 | $3.9 \times 10^8$ | 50 |
| 2 B/liquid detergent tabs Aminoplast | 92.9 | 26.4 | 66.5 | 6.6 | $1.5 \times 10^8$ | 15 |
| 3 A/Shampoo PU(*) | 89.0 | 43.2 | 45.8 | 4.6 | $5.9 \times 10^7$ | 60 |
| 4 A/Shampoo PU(*) | 99 | 4 | 95 | 89.1 | $2.3 \times 10^7$ | <10 |

(*)The Capsules PU were obtained as described in WO 2011/0058929 A1, example 2.

The results show a clear correlation between the RECON_ VOLTAE value distribution and the leakage. Furthermore, the results show also that it is possible to obtain perfume compositions that not only are stable under various storage conditions, while still being diffusive, as illustrated by the high tPROC values. Conversely, it is possible to obtain very stable perfume compositions, using high level of high RECON_VOLTAE materials, but then the pre-rub impact may then decrease below an acceptable value (see for example, the case of perfume 4 A in shampoos).

EXAMPLE 6

A series of perfumes were encapsulated by using the process described in Example 2. In these cases, both the distribution of RECON_VOLTAE values and the total Pre-Rub Odour Contribution (tPROC) was varied. The capsule were dispersed in the liquid detergent base for liquid tabs described in Example 2. Wash tests were performed after one month storage in thermostated hood at 37° C., using standard front-loaded wash machine and terry towelling as standard substrate. The pre-rub performance was evaluated by smelling the towel on dry towel, taking care not to break the capsules. A panel of 10 trained panellists was used. Both evaluation scores and characteristics of the encapsulated perfumes are reported in Table 6. The following relative scale was used: 1: barely noticeable odour, 2: medium odour strength, 3: strong odour and 4: very strong odour.

TABLE 6

Perfume features and capsule pre-rub performance in liquid detergent tabs after storage (RV means RECON_VOLTAE and the total Pre Rub Odour Contribution (tPROC) has been divided by $10^8$ for clarity)

| RV > 1200 | RV > 1540 | RV > 1750 | tPROC/$10^8$ | SCORE |
|---|---|---|---|---|
| 90.95 | 31.00 | 8.50 | 3.3 | 4 |
| 93.50 | 75.30 | 2.50 | 2.5 | 4 |
| 90.00 | 33.00 | 2.00 | 6.7 | 4 |

TABLE 6-continued

Perfume features and capsule pre-rub performance in liquid detergent tabs after storage (RV means RECON_VOLTAE and the total Pre Rub Odour Contribution (tPROC) has been divided by $10^8$ for clarity)

| RV > 1200 | RV > 1540 | RV > 1750 | tPROC/$10^8$ | SCORE |
|---|---|---|---|---|
| 96.90 | 84.30 | 2.50 | 3.6 | 4 |
| 93.00 | 66.80 | 8.00 | 2.1 | 3 |
| 100.00 | 50.00 | 2.00 | 1.1 | 3 |
| 97.00 | 53.00 | 0.00 | 2 | 3 |
| 97.00 | 55.50 | 9.00 | 2.7 | 3 |
| 100.00 | 42.50 | 7.00 | 1.1 | 3 |
| 97.00 | 35.00 | 14.00 | 4.4 | 3 |
| 100.00 | 55.40 | 15.00 | 0.6 | 3 |
| 91.65 | 39.45 | 18.00 | 2 | 3 |
| 92.85 | 52.60 | 25.50 | 1 | 3 |
| 96.00 | 51.50 | 51.50 | 1.6 | 1 |
| 93.00 | 55.78 | 28.49 | 1.4 | 1 |
| 100.00 | 85.00 | 35.00 | 0.2 | 1 |

As apparent from the results in Table 6, there is a clear optimum in terms of both RECON_VOLTAE distribution and tPROC distribution. The relevance of the pPROC parameter is also demonstrated. As mentioned in Example 5, high levels of ingredients having RECON_VOLTAE values higher than 1750 are beneficial to capsule resistance against leakage during storage, but is deleterious to pre-rub impact. The present example teaches that it is advantageous not to use RV>1750 ingredients at levels higher than 20 to 25 wt % in the encapsulated perfume composition of the present invention.

The invention claimed is:

1. A method of selecting perfume ingredients for an encapsulated perfume composition, the method comprising:
    (i) determining the RECON_VOLTAE values of the perfume ingredients, wherein the RECON_VOLTAE value is the integral of the molecular iso-surface having an electron density equal to $$0.002 e/a_0^3$$

wherein e is the dimension-less electron charge and $a_0$ is the Bohr radius of the hydrogen atom;

(ii) selecting the ingredients such that more than 70 wt % of the perfume ingredients have known RECON_VOLTAE values larger than about 1200 Bohr$^3$; and (iii) at least one selected from:
mixing the selected ingredients together; and
forming microcapsules comprising the selected ingredients.

2. The method of claim 1, wherein more than 80 wt % of the selected ingredients have known RECON_VOLTAE values larger than about 1200 Bohr$^3$.

3. The method of claim 1, wherein more than 30 wt % of the selected ingredients have known RECON_VOLTAE values larger than about 1540 Bohr$^3$.

4. The method of claim 1, wherein more than 70 wt % of the selected ingredients have known RECON_VOLTAE values larger than about 1750 Bohr$^3$.

5. The method of claim 1, wherein at least three selected ingredients have RECON_VOLTAE values larger than about 1200 Bohr$^3$.

6. The method of claim 1, wherein
30 wt % or more of the selected ingredients have known RECON_VOLTAE values larger than 1540 Bohr$^3$;
20 to 60 wt % of the selected ingredients have known RECON_VOLTAE values from 1200 Bohr$^3$ to 1540 Bohr$^3$; and
0.1 to 30 wt % of the selected ingredients have known RECON_VOLTAE values below 1200 Bohr$^3$.

7. The method of claim 1, wherein
from 0.5 to 30 wt % of the selected ingredients have known RECON_VOLTAE values above 1750 Bohr$^3$;
20 to 60 wt % of the selected ingredients have known RECON_VOLTAE values from 1540 Bohr$^3$ to 1750 Bohr$^3$; and
5 to 50 wt % or more of the selected ingredients have known RECON_VOLTAE values from 1200 Bohr$^3$ to 1540 Bohr$^3$; and
0.1 to 30 wt % of the selected ingredients have known RECON_VOLTAE values below 1200 Bohr$^3$.

8. The method of claim 1, wherein the selected ingredients have a $\log_{10}$ Kcaps value greater than −3.

9. The method of claim 1, wherein the total Pre-Rub Odour Contribution of the selected ingredients is between about $0.5 \times 10^8$ and $1.0 \times 10^9$.

10. A method of preparing an encapsulated perfume composition comprising at least one microcapsule dispersed in a suspending medium, the method comprising (a) mixing together the selected ingredients according to claim 1 to form perfume droplets; and (b) forming a dispersion or emulsion of the perfume droplets in an aqueous phase to produce the at least one microcapsule.

11. The method of claim 10, wherein a core to shell weight ratio of the at least one microcapsule is about 90:10.

12. A method of forming a consumer product comprising:
incorporating the encapsulated perfume composition according to claim 10 into said consumer product.

13. The method of claim 2, wherein more than 90 wt % of the selected ingredients have known RECON_VOLTAE values larger than about 1200 Bohr$^3$.

14. The method of claim 3, wherein more than 40 wt % of the selected ingredients have known RECON_VOLTAE values larger than about 1540 Bohr$^3$.

15. The method of claim 4, wherein more than 90 wt % of selected ingredients have known RECON_VOLTAE values larger than about 1750 Bohr$^3$.

16. The method of claim 5, wherein at least five selected ingredients have RECON_VOLTAE values larger than about 1200 Bohr$^3$.

17. The method according to claim 6, wherein
40 wt % or more of the selected ingredients have known RECON_VOLTAE values larger than 1540 Bohr$^3$;
30 to 40 wt % of the selected ingredients have known RECON_VOLTAE values from 1200 Bohr$^3$ to 1540 Bohr$^3$; and
from 1 to 10 wt % of the selected ingredients have known RECON_VOLTAE values below 1200 Bohr$^3$.

18. The method of claim 7, wherein
from 5 to 20 wt % of the selected ingredients have known RECON_VOLTAE values above 1750 Bohr$^3$;
from 30 to 50 wt % of the selected ingredients have known RECON_VOLTAE values from 1540 Bohr$^3$ to 1750 Bohr$^3$;
15 to 30 wt % of the selected ingredients have known RECON_VOLTAE values from 1200 Bohr$^3$ to 1540 Bohr$^3$; and
from 1 to 10 wt % of the selected ingredients have known RECON_VOLTAE values below 1200 Bohr$^3$.

19. The method of claim 9, wherein the total Pre-Rub Odour Contribution of the selected ingredients is between $1.5 \times 10^8$ and $6 \times 10^8$.

* * * * *